(12) United States Patent
Li et al.

(10) Patent No.: US 10,959,810 B2
(45) Date of Patent: Mar. 30, 2021

(54) DIRECT FABRICATION OF ALIGNERS FOR PALATE EXPANSION AND OTHER APPLICATIONS

(71) Applicant: ALIGN TECHNOLOGY, INC., San Jose, CA (US)

(72) Inventors: Chunhua Li, Cupertino, CA (US); Avi Kopelman, Palo Alto, CA (US); Srinivas Kaza, San Francisco, CA (US); Ryan Kimura, San Jose, CA (US); Yaser Shanjani, Sunnyvale, CA (US)

(73) Assignee: ALIGN TECHNOLOGY, INC., San Jose, CA (US)

( * ) Notice: Subject to any disclaimer, the term of this patent is extended or adjusted under 35 U.S.C. 154(b) by 0 days.

(21) Appl. No.: 15/202,467

(22) Filed: Jul. 5, 2016

(65) Prior Publication Data

US 2017/0007367 A1   Jan. 12, 2017

Related U.S. Application Data

(60) Provisional application No. 62/189,301, filed on Jul. 7, 2015, provisional application No. 62/189,271, filed on Jul. 7, 2015.

(51) Int. Cl.
*A61C 7/00* (2006.01)
*A61C 7/08* (2006.01)
(Continued)

(52) U.S. Cl.
CPC ............ *A61C 7/002* (2013.01); *A44C 15/007* (2013.01); *A61C 7/08* (2013.01); *A61C 7/10* (2013.01);
(Continued)

(58) Field of Classification Search
CPC ...... A61C 19/066; A61C 19/063; A61C 7/002; A61C 7/10; A61C 7/08; A61C 13/0019;
(Continued)

(56) References Cited

U.S. PATENT DOCUMENTS 2,467,432 A   4/1949  Kesling
3,407,500 A   10/1968 Kesling
(Continued)

FOREIGN PATENT DOCUMENTS

AU   3031677 A   5/1979
AU   517102 B2   7/1981
(Continued)

OTHER PUBLICATIONS

AADR. American Association for Dental Research, Summary of Activities, Mar. 20-23, 1980, Los Angeles, CA, p. 195.
(Continued)

*Primary Examiner* — Edward Moran
*Assistant Examiner* — Matthew P Saunders
(74) *Attorney, Agent, or Firm* — Wilson Sonsini Goodrich & Rosati

(57) ABSTRACT

Systems, methods, and devices for producing appliances for expansion of the palate of a patient are provided. A palate expanding orthodontic appliance comprises a teeth engagement portion comprising a plurality of teeth engagement structures and a force generating portion coupled to the teeth engagement portion and configured to apply force to cause the patient's palate to expand. The orthodontic appliances can be designed according to the specifications provided herein and manufactured using direct fabrication methods.

6 Claims, 29 Drawing Sheets

(51) Int. Cl.
| | |
|---|---|
| *A61C 7/10* | (2006.01) |
| *A61C 19/06* | (2006.01) |
| *A61C 13/00* | (2006.01) |
| *B29C 64/386* | (2017.01) |
| *G16H 20/40* | (2018.01) |
| *A44C 15/00* | (2006.01) |
| *B23K 26/362* | (2014.01) |
| *B44C 1/22* | (2006.01) |
| *G06Q 30/06* | (2012.01) |
| *B33Y 30/00* | (2015.01) |
| *B33Y 50/00* | (2015.01) |
| *B33Y 10/00* | (2015.01) |
| *B33Y 80/00* | (2015.01) |

(52) U.S. Cl.
CPC ........ *A61C 13/0019* (2013.01); *A61C 19/066* (2013.01); *B23K 26/362* (2013.01); *B29C 64/386* (2017.08); *B44C 1/227* (2013.01); *B44C 1/228* (2013.01); *G06Q 30/0621* (2013.01); *G06Q 30/0643* (2013.01); *G16H 20/40* (2018.01); *A61C 13/0013* (2013.01); *A61C 2201/007* (2013.01); *B33Y 10/00* (2014.12); *B33Y 30/00* (2014.12); *B33Y 50/00* (2014.12); *B33Y 80/00* (2014.12)

(58) Field of Classification Search
CPC ... A61C 13/0013; A61C 8/0096; A61C 19/63; A61C 19/66; A61C 7/008
USPC .............................. 433/6, 8, 24, 37; 128/861
See application file for complete search history.

(56) References Cited

U.S. PATENT DOCUMENTS

| | | |
|---|---|---|
| 3,600,808 A | 8/1971 | Reeve |
| 3,660,900 A | 5/1972 | Andrews |
| 3,683,502 A | 8/1972 | Wallshein |
| 3,738,005 A | 6/1973 | Cohen et al. |
| 3,860,803 A | 1/1975 | Levine |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,195,046 A | 3/1980 | Kesling |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,433,956 A | 2/1984 | Witzig |
| 4,478,580 A | 10/1984 | Barrut |
| 4,500,294 A | 2/1985 | Lewis |
| 4,504,225 A | 3/1985 | Yoshii |
| 4,505,673 A | 3/1985 | Yoshii |
| 4,526,540 A | 7/1985 | Dellinger |
| 4,573,914 A | 3/1986 | Nord |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | Van Der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell |
| 5,002,485 A | 3/1991 | Aagesen |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,382,164 A | 1/1995 | Stern |
| 5,395,238 A | 3/1995 | Andreiko et al. |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,562,448 A | 10/1996 | Mushabac |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre, Sr. |
| 5,621,648 A | 4/1997 | Crump |
| 5,645,420 A | 7/1997 | Bergersen |
| 5,645,421 A | 7/1997 | Slootsky |
| 5,655,653 A | 8/1997 | Chester |
| 5,683,243 A | 11/1997 | Andreiko et al. |
| 5,692,894 A | 12/1997 | Schwartz et al. |
| 5,725,376 A | 3/1998 | Poirier |
| 5,725,378 A | 3/1998 | Wang |
| 5,733,126 A | 3/1998 | Andersson et al. |
| 5,740,267 A | 4/1998 | Echerer et al. |
| 5,742,700 A | 4/1998 | Yoon et al. |
| 5,769,631 A | 6/1998 | Williams |
| 5,799,100 A | 8/1998 | Clarke et al. |
| 5,800,174 A | 9/1998 | Andersson |
| 5,823,778 A | 10/1998 | Schmitt et al. |
| 5,848,115 A | 12/1998 | Little et al. |
| 5,857,853 A | 1/1999 | Van Nifterick et al. |

(56) References Cited

U.S. PATENT DOCUMENTS

| | | |
|---|---|---|
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 6,015,289 A | 1/2000 | Andreiko et al. |
| 6,044,309 A | 3/2000 | Honda |
| 6,049,743 A | 4/2000 | Baba |
| 6,062,861 A | 5/2000 | Andersson |
| 6,068,482 A | 5/2000 | Snow |
| 6,099,314 A | 8/2000 | Kopelman et al. |
| 6,123,544 A | 9/2000 | Cleary |
| 6,152,731 A | 11/2000 | Jordan et al. |
| 6,183,248 B1 | 2/2001 | Chishti et al. |
| 6,190,165 B1 | 2/2001 | Andreiko et al. |
| 6,217,325 B1 | 4/2001 | Chishti et al. |
| 6,217,334 B1 | 4/2001 | Hultgren |
| 6,244,861 B1 | 6/2001 | Andreiko et al. |
| 6,309,215 B1 | 10/2001 | Phan et al. |
| 6,315,553 B1 | 11/2001 | Sachdeva et al. |
| 6,322,359 B1 | 11/2001 | Jordan et al. |
| 6,350,120 B1 | 2/2002 | Sachdeva et al. |
| 6,382,975 B1 | 5/2002 | Poirier |
| 6,398,548 B1 | 6/2002 | Muhammad et al. |
| 6,402,707 B1 | 6/2002 | Ernst |
| 6,450,807 B1 | 9/2002 | Chishti et al. |
| 6,471,511 B1 | 10/2002 | Chishti et al. |
| 6,482,298 B1 | 11/2002 | Bhatnagar |
| 6,499,995 B1 | 12/2002 | Schwartz |
| 6,524,101 B1 | 2/2003 | Phan et al. |
| 6,554,611 B2 | 4/2003 | Shishti et al. |
| 6,572,372 B1* | 6/2003 | Phan ................. A61C 7/00 433/18 |
| 6,626,180 B1 | 9/2003 | Kittelsen et al. |
| 6,629,840 B2 | 10/2003 | Chishti et al. |
| 6,691,710 B2* | 2/2004 | Kittelsen ............ A63B 71/085 128/859 |
| 6,705,863 B2 | 3/2004 | Phan et al. |
| 6,722,880 B2 | 4/2004 | Chishti et al. |
| 6,749,414 B1 | 6/2004 | Hanson et al. |
| 6,830,450 B2 | 12/2004 | Knopp et al. |
| 7,500,851 B2 | 3/2009 | Williams |
| 7,553,157 B2 | 6/2009 | Abolfathi et al. |
| 7,559,328 B2* | 7/2009 | Eubank ............... A61C 7/08 128/848 |
| 7,874,836 B2* | 1/2011 | McSurdy, Jr. ....... A61C 7/10 433/6 |
| 7,878,801 B2 | 2/2011 | Abolfathi et al. |
| 7,892,474 B2 | 2/2011 | Shkolnik et al. |
| 8,017,891 B2 | 9/2011 | Nevin |
| 8,439,672 B2 | 5/2013 | Matov et al. |
| 8,439,674 B2 | 5/2013 | Li et al. |
| 8,444,412 B2* | 5/2013 | Baughman .......... A61C 7/08 433/24 |
| 8,567,408 B2* | 10/2013 | Roettger ............. A61C 5/90 128/861 |
| 8,758,009 B2 | 6/2014 | Chen et al. |
| 8,899,976 B2 | 12/2014 | Chen et al. |
| 9,108,338 B2 | 8/2015 | Sirovskiy et al. |
| 1,055,579 A1 | 2/2020 | Kopelman et al. |
| 2002/0006597 A1 | 1/2002 | Andreiko et al. |
| 2003/0009252 A1 | 1/2003 | Pavlovskaia et al. |
| 2003/0049581 A1* | 3/2003 | DeLuke ............... A61C 7/10 433/7 |
| 2003/0139834 A1 | 7/2003 | Nikolskiy et al. |
| 2003/0157454 A1 | 8/2003 | Hansen et al. |
| 2003/0190576 A1 | 10/2003 | Phan et al. |
| 2003/0224311 A1 | 12/2003 | Cronauer |
| 2004/0009449 A1* | 1/2004 | Mah .................... A61C 7/08 433/7 |
| 2004/0128010 A1 | 7/2004 | Pavlovskaia et al. |
| 2004/0209218 A1 | 10/2004 | Chishti et al. |
| 2005/0037312 A1 | 2/2005 | Uchida |
| 2005/0055118 A1 | 3/2005 | Nikolskiy et al. |
| 2005/0072435 A1* | 4/2005 | Eubank ............... A61C 7/08 128/861 |
| 2005/0186524 A1* | 8/2005 | Abolfathi ............ A61C 7/10 433/7 |
| 2006/0099546 A1 | 5/2006 | Bergersen |
| 2007/0231765 A1 | 10/2007 | Phan et al. |
| 2008/0003535 A1* | 1/2008 | Williams ............ A61C 7/10 433/7 |
| 2008/0268400 A1* | 10/2008 | Moss .................. A61C 7/00 433/24 |
| 2009/0246724 A1* | 10/2009 | Chen .................. A61C 7/08 433/6 |
| 2010/0092905 A1 | 4/2010 | Martin |
| 2010/0138025 A1 | 6/2010 | Morton et al. |
| 2010/0239993 A1* | 9/2010 | Baughman .......... A61C 7/08 433/6 |
| 2010/0279245 A1 | 11/2010 | Navarro |
| 2011/0281229 A1 | 11/2011 | Abolfathi |
| 2011/0287377 A1* | 11/2011 | Hang .................. A61C 7/00 433/7 |
| 2012/0037168 A1* | 2/2012 | Jackson .............. A61F 5/0006 128/861 |
| 2012/0129117 A1* | 5/2012 | McCance ............ A61C 7/10 433/7 |
| 2013/0095446 A1 | 4/2013 | Andreiko et al. |
| 2014/0061974 A1 | 3/2014 | Tyler et al. |
| 2014/0265034 A1 | 9/2014 | Dudley |
| 2014/0363778 A1 | 12/2014 | Parker |
| 2015/0097315 A1 | 4/2015 | Desimone et al. |
| 2015/0097316 A1 | 4/2015 | Desimone et al. |
| 2015/0102532 A1 | 4/2015 | Desimone et al. |
| 2015/0245887 A1* | 9/2015 | Izugami ............. A61C 7/08 433/6 |
| 2016/0081767 A1* | 3/2016 | Metcalf .............. A61C 7/10 433/6 |
| 2016/0081768 A1 | 3/2016 | Kopelman et al. |
| 2016/0081769 A1* | 3/2016 | Kimura .............. A61C 7/10 433/6 |
| 2016/0128803 A1 | 5/2016 | Webber et al. |
| 2017/0007359 A1 | 1/2017 | Kopelman et al. |
| 2017/0007360 A1 | 1/2017 | Kopelman et al. |
| 2017/0007361 A1 | 1/2017 | Boronkay et al. |
| 2017/0007362 A1 | 1/2017 | Chen et al. |
| 2017/0007363 A1 | 1/2017 | Boronkay |
| 2017/0007365 A1 | 1/2017 | Kopelman et al. |
| 2017/0007366 A1 | 1/2017 | Kopelman et al. |
| 2017/0007368 A1 | 1/2017 | Boronkay |
| 2017/0007386 A1 | 1/2017 | Mason et al. |
| 2017/0008333 A1 | 1/2017 | Mason et al. |
| 2017/0079747 A1* | 3/2017 | Graf .................. A61C 7/002 |
| 2017/0135850 A1* | 5/2017 | Veis ................... A61F 5/566 |

FOREIGN PATENT DOCUMENTS

| | | |
|---|---|---|
| AU | 5598894 A | 6/1994 |
| CA | 1121955 A | 4/1982 |
| CN | 1407881 A | 4/2003 |
| DE | 2749802 A1 | 5/1978 |
| DE | 69327661 T2 | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 1/2000 |
| EP | 0774933 B1 | 12/2000 |
| EP | 0731673 B1 | 5/2001 |
| EP | 2866290 A1 | 5/2015 |
| ES | 463897 A1 | 1/1980 |
| FR | 2369828 A1 | 6/1978 |
| FR | 2652256 A1 | 3/1991 |
| GB | 15500777 | 8/1979 |
| JP | S5358191 A | 5/1978 |
| JP | H0428359 A | 1/1992 |

(56) References Cited

FOREIGN PATENT DOCUMENTS

| | | |
|---|---|---|
| JP | 08508174 | 9/1996 |
| JP | 2007260158 A | 10/2007 |
| JP | 2010240030 A | 10/2010 |
| WO | WO-9008512 A1 | 8/1990 |
| WO | WO-9104713 A1 | 4/1991 |
| WO | WO-9410935 A1 | 5/1994 |
| WO | WO-9832394 A1 | 7/1998 |
| WO | WO-9844865 A1 | 10/1998 |
| WO | WO-9858596 A1 | 12/1998 |
| WO | WO-0180762 A2 | 11/2001 |

OTHER PUBLICATIONS

Alcaniz, et al, "An Advanced System for the Simulation and Planning of Orthodontic Treatments," Karl Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.

Alexander et al., "The DigiGraph Work Station Part 2 Clinical Management," JCO, pp. 402-407 (Jul. 1990).

Altschuler, "3D Mapping of Maxillo-Facial Prosthesis," AADR Abstract #607, 2 pages total, (1980).

Altschuler et al., "Analysis of 3-D Data for Comparative 3-D Serial Growth Pattern Studies of Oral-Facial Structures," AADR Abstracts, Program and Abstracts of Papers, 57th General Session, IADR HP Annual Session, Mar. 29, 1979-Apr. 1, 1979, New Orleans Marriot, Journal of Dental Research, vol. 58, Jan. 1979, Special Issue A, p. 221.

Altschuler et al., "Laser Electro-Optic System for Rapid Three-Dimensional (3D) Topographic Mapping of Surfaces," Optical Engineering, 20(6):953-961 (1981).

Altschuler et al., "Measuring Surfaces Space-Coded by a Laser-Projected Dot Matrix," SPIE Imaging Applications for Automated Industrial Inspection and Assembly, vol. 182, p. 187-191 (1979).

Andersson et al., "Clinical Results with Titanium Crowns Fabricated with Machine Duplication and Spark Erosion," Acta. Odontol. Scand., 47:279-286 (1989).

Andrews, The Six Keys to Optimal Occlusion Straight Wire, Chapter 3, pp. 13-24 (1989).

Bartels, et al., An Introduction to Splines for Use in Computer Graphics and Geometric Modeling, Morgan Kaufmann Publishers, pp. 422-425 (1987).

Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.

Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.

Baumrind et al., "Mapping the Skull in 3-D," reprinted from J. Calif. Dent. Assoc., 48(2), 11 pages total, (1972 Fall Issue).

Baumrind, "Integrated Three-Dimensional Craniofacial Mapping: Background, Principles, and Perspectives," Semin. in Orthod., 7(4):223-232 (Dec. 2001).

Begole et al., "A Computer System for the Analysis of Dental Casts," The Angle Orthod., 51(3):253-259 (Jul. 1981).

Bernard et al.,"Computerized Diagnosis in Orthodontics for Epidemiological Studies: A Progress Report," Abstract, J. Dental Res. Special Issue, vol. 67, p. 169, paper presented at International Association for Dental Research 66th General Session, Mar. 9-13, 1988, Montreal, Canada.

Bhatia et al., "A Computer-Aided Design for Orthognathic Surgery," Br. J. Oral Maxillofac. Surg., 22:237-253 (1984).

Biggerstaff, "Computerized Diagnostic Setups and Simulations," Angle Orthod., 40(1):28-36 (Jan. 1970).

Carbon3D. CLIP Technology. A new approach to 3D printing. 2015. http://carbon3d.com/ Accessed Jul. 1, 2015.

Cardinal Industrial Finishes, Powder Coatings information posted at< http://www.cardinalpaint.com>on Aug. 25, 2000, 2 pages.

Carnaghan, "An Alternative to Holograms for the Portrayal of Human Teeth," 4th Int'l Conf. on Holographic Systems, Components and Applications, Sep. 15, 1993, pp. 228-231.

Chaconas et al., "The DigiGraph Work Station, Part 1, Basic Concepts," JCO, pp. 360-367 (Jun. 1990).

Chafetz et al., "Subsidence of the Femoral Prosthesis, a Stereophotogrammetric Evaluation," Clin. Orthop. Relat. Res., No. 201, pp. 60-67 (Dec. 1985).

Chiappone, (1980). Constructing the Gnathologic Setup and Positioner, J. Clin. Orthod, vol. 14, pp. 121-133.

Composite material. Wikipedia. Last modified Jun. 22, 2015. https://en.wikipedia.org/wiki/Composite_material.

Cottingham, (1969). Gnathologic Clear Plastic Positioner, Am. J. Orthod, vol. 55, pp. 23-31.

Crawford, "CAD/CAM in the Dental Office: Does It Work?", Canadian Dental Journal, vol. 57, No. 2, pp. 121-123 (Feb. 1991).

Crawford, "Computers in Dentistry: Part 1 CAD/CAM: The Computer Moves Chairside," Part 2 F. Duret—A Man with a Vision,"Part 3 The Computer Gives New Vision—Literally, Part 4 Bytes 'N Bites—The Computer Moves from the Front Desk to the Operatory," Canadian Dental Journal, vol. 54 (9), pp. 661-666 (1988).

Biggerstaff et al., "Computerized Analysis of Occlusion in the Postcanine Dentition," Am. J. Orthod., 61(3): 245-254 (Mar. 1972).

Biostar Opeation & Training Manual. Great Lakes Orthodontics, Ltd. 199 Fire Tower Drive, Tonawanda, New York. 14150-5890, 20 pages total (1990).

Blu, et al., "Linear interpolation revitalized", IEEE Trans. Image Proc., 13(5):710-719 (May 2004).

Bourke, "Coordinate System Transformation," (Jun. 1996), p. 1, retrieved from the Internet Nov. 5, 2004, URL< http://astronomy.swin.edu.au/-pbourke/prolection/coords>.

Boyd et al., "Three Dimensional Diagnosis and Orthodontic Treatment of Complex Malocclusions With the Invisalipn Appliance," Semin. Orthod., 7(4):274-293 (Dec. 2001).

Brandestini et al., "Computer Machined Ceramic Inlays: In Vitro Marginal Adaptation," J. Dent. Res. Special Issue, Abstract 305, vol. 64, p. 208 (1985).

Brook et al., "An Image Analysis System for the Determination of Tooth Dimensions from Study Casts: Comparison with Manual Measurements of Mesio-distal Diameter," J. Dent. Res., 65(3):428-431 (Mar. 1986).

Burstone et al., Precision Adjustment of the Transpalatal Lingual Arch: Computer Arch Form In Predetermination, Am, Journal of Orthodontics, vol. 79, No. 2 (Feb. 1981), pp. 115-133.

Burstone (interview), "Dr. Charles J. Burstone on the Uses of the Computer in Orthodontic Practice (Part 1)," J. Clin. Orthod., 13(7):442-453 (Jul. 1979).

Burstone (interview), "Dr. Charles J. Burstone on the Uses of the Computer in Orthodontic Practice (Part 2)," J. Clin. Orthod., 13(8):539-551 (Aug. 1979).

Desimone. What if 3D printing was 100% faster? TEDtalk. Mar. 2015. http://www.ted.com/talks/joe_desimone_what_if_3d_printing_was_25x_faster.

Doyle, "Digital Dentistry," Computer Graphics World, pp. 50-52, 54 (Oct. 2000).

DuraClearTM product information, Allesee Orthodontic Appliances-Pro Lab, 1 page (1997).

Duret et al., "CAD/CAM Imaging in Dentistry," Curr. Opin. Dent., 1:150-154 (1991).

Duret et al, "CAD-CAM in Dentistry," J. Am. Dent. Assoc. 117:715-720 (Nov. 1988).

Duret, "The Dental CAD/CAM, General Description of the Project," Hennson International Product Brochure, 18 pages total, Jan. 1986.

Duret,"Vers Une Prosthese Informatisee," (English translation attached), Tonus, vol. 75, pp. 55-57 (Nov. 15, 1985).

Economides, "The Microcomputer in the Orthodontic Office," JCO, pp. 767-772 (Nov. 1979).

Elsasser, Some Observations on the History and Uses of the Kesling Positioner, Am. J. Orthod. (1950) 36:368-374.

(56) References Cited

OTHER PUBLICATIONS

English translation of Japanese Laid-Open Publication No. 63-11148 to inventor T. Ozukuri (Laid-Open on Jan. 18, 1998) pp. 1-7.
Felton et al., "A Computerized Analysis of the Shape and Stability of Mandibular Arch Form," Am. J. Orthod. Dentofacial Orthop., 92(6):478-483 (Dec. 1987).
Crooks, "CAD/CAM Comes to USC," USC Dentistry, pp. 14-17 (Spring 1990).
Cureton, Correcting Malaligned Mandibular Incisors with Removable Retainers, J. Clin. Orthod, vol. 30, No. 7 (1996) pp. 390-395.
Curry et al., "Integrated Three-Dimensional Craniofacial Mapping at the Craniofacial Research Instrumentation Laboratory/University of the Pacific," Semin. Orthod., 7(4):258-265 (Dec. 2001).
Cutting et a/., "Three-Dimensional Computer-Assisted Design of Craniofacial Surgical Procedures: Optimization and Interaction with Cephalometric and CT-Based Models," Plast. 77(6):877-885 (Jun. 1986).
DCS Dental AG, "The CAD/CAM 'DCS Titan System' for Production of Crowns/Bridges," DSC Production AG, pp. 1-7 (Jan. 1992.
Definition for gingiva. Dictionary.com p. 1-3. Retrieved from the internet Nov. 5, 2004< http://reference.com/search/search?q=gingiva>.
Defranco et al., "Three-Dimensional Large Displacement Analysis of Orthodontic Appliances," J. Biomechanics, 9:793-801 (1976).
Dental Institute University of Zurich Switzerland, Program for International Symposium JD on Computer Restorations: State of the Art of the CEREC-Method, May 1991, 2 pages total.
Dentrac Corporation, Dentrac document, pp. 4-13 (1992).
Dent-X posted on Sep. 24, 1998 at< http://www.dent-x.com/DentSim.htm>, 6 pages.
Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingampproduction/november011996/simulatingstressputonfa . . . >.
Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total).
Hipolite. Helios One 3D Printer—New Heliolithography Technology Could Eventually Replace SLA and FDM. Jul. 2, 2014. http://3dprint.com/7958/orange-maker-helio-one-3d/.
Hoffmann, et al., "Role of Cephalometry for Planning of Jaw Orthopedics and Jaw Surgery Procedures," (Article Summary in English, article in German), Informatbnen, pp. 375-396 (Mar. 1991).
Hojjatie et al., "Three-Dimensional Finite Element Analysis of Glass-Ceramic Dental Crowns," J. Biomech., 23(11):1157-1166 (1990).
Huckins, "CAD-CAM Generated Mandibular Model Prototype from MRI Data," AAOMS, p. 96 (1999).
Important Tip About Wearing the Red White & Blue Active Clear Retainer System, Allesee Orthodontic Appliances—Pro Lab, 1 page 1998).
"International search report with written opinion dated Nov. 30, 2016 for PCT/IB2016/000975".
JCO Interviews, Craig Andreiko , DDS, MS on the Elan and Orthos Systems, JCO, pp. 459-468 (Aug. 1994).
Friede et al., "Accuracy of Cephalometric Prediction in Orthognathic Surgery," Abstract of Papers, J. Dent. Res., 70:754-760 (1987).
Futterling et a/., "Automated Finite Element Modeling of a Human Mandible with Dental Implants," JS WSCG '98—Conference Program, retrieved from the Internet:<http://wscg.zcu.cz/wscg98/papers98/Strasser 98.pdf>, 8 pages.
Gao et al., "3-D element Generation for Multi-Connected Complex Dental and Mandibular Structure," Proc. Intl Workshop on Medical Imaging and Augmented Reality, pp. 267-271 (Jun. 12, 2001).

Gim-Alldent Deutschland, "Das DUX System: Die Technik," 2 pages total (2002).
Gottlieb et al., "JCO Interviews Dr. James A. McNamura, Jr., on the Frankel Appliance: Part 2: Clinical 1-1 Management, "J. Clin. Orthod., 16(6):390-407 (Jun. 1982).
Grayson, "New Methods for Three Dimensional Analysis of Craniofacial Deformity, Symposium: JW Computerized Facial Imaging in Oral and Maxiiofacial Surgery," AAOMS, 3 pages total, (Sep. 13, 1990).
Guess et al., "Computer Treatment Estimates in Orthodontics and Orthognathic Surgery," JCO, pp. 262-268 (Apr. 1989).
Halterman. A path to the future—continuous composite 3D printing. Nov. 12, 2014. http://www.3dprinterworld.com/article/path-future-continuous-composite-3d-printing.
Heaven et a/., "Computer-Based Image Analysis of Artificial Root Surface Caries, Abstracts of Papers," J. Dent. Res., 70:528 (Apr. 17-21, 1991).
Kochanek, "Interpolating Splines with Local Tension, Continuity and Bias Control," Computer Graphics, ri 18(3):33-41 (Jul. 1984).
KM Oral Surgery (1945) 31 :297-30.
Kunii et al., "Articulation Simulation for an Intelligent Dental Care System," Displays 15:181-188 (1994).
Kuroda et al., Three-Dimensional Dental Cast Analyzing System Using Laser Scanning, Am. J. Orthod. Dentofac. Orthop. (1996) 110:365-369.
Laurendeau, et al., "A Computer-Vision Technique for the Acquisition and Processing of 3-D Profiles of 7 KR Dental Imprints: An Application in Orthodontics," IEEE Transactions on Medical Imaging, 10(3):453-461 (Sep. 1991.
Leinfelder, et al., "A New Method for Generating Ceramic Restorations: a CAD-CAM System," J. Am. 1-1 Dent. Assoc., 118(6):703-707 (Jun. 1989).
Manetti, et al., "Computer-Aided Cefalometry and New Mechanics in Orthodontics," (Article Summary in English, article in German), Fortschr Kieferorthop. 44, 370-376 (Nr. 5), 1983.
McCann, "Inside the ADA," J. Amer. Dent. Assoc., 118:286-294 (Mar. 1989).
McNamara et al., "Invisible Retainers," J. Cfin. Orthod., pp. 570-578 (Aug. 1985).
McNamara et al., Orthodontic and Orthopedic Treatment in the Mixed Dentition, Needham Press, pp. 347-353 (Jan. 1993).
Moermann et al., "Computer Machined Adhesive Porcelain Inlays: Margin Adaptation after Fatigue Stress," IADR Abstract 339, J. Dent. Res., 66(a):763 (1987).
JCO Interviews, Dr. Homer W. Phillips on Computers in Orthodontic Practice, Part 2, JCO. 1997; 1983:819-831.
Jerrold, "The Problem, Electronic Data Transmission and the Law," AJO-DO, pp. 478-479 (Apr. 1988).
Jones et al., "An Assessment of the Fit of a Parabolic Curve to Pre- and Post-Treatment Dental Arches," Br. J. Orthod., 16:85-93 (1989).
JP Faber et al., "Computerized Interactive Orthodontic Treatment Planning," Am. J. Orthod., 73(1):36-46 (Jan. 1978).
Kamada et.al., Case Reports on Tooth Positioners Using LTV Vinyl Silicone Rubber, J. Nihon University School of Dentistry (1984) 26(1): 11-29.
Kamada et.al., Construction of Tooth Positioners with LTV Vinyl Silicone Rubber and Some Case KJ Reports, J. Nihon University School of Dentistry (1982) 24(1):1-27.
Kanazawa et al., "Three-Dimensional Measurements of the Occlusal Surfaces of Upper Molars in a Dutch Population," J. Dent Res., 63(11):1298-1301 (Nov. 1984).
Kesling, Coordinating the Predetermined Pattern and Tooth Positioner with Conventional Treatment, KN Am. J. Orthod. Oral Surg. (1946) 32:285-293.
Kesling et al., The Philosophy of the Tooth Positioning Appliance, American Journal of Orthodontics and Oral surgery. 1945; 31:297-304.
Kleeman et al., The Speed Positioner, J. Clin. Orthod. (1996) 30:673-680.
Yoshii, "Research on a New Orthodontic Appliance: The Dynamic Positioner (D.P.); III.—The General Concept of the D.P. Method and Its Therapeutic Effect, Part 2. Skeletal Reversed Occlusion Case Reports," Nippon Dental Review, 458:112-129 (Dec. 1980).

(56) References Cited

OTHER PUBLICATIONS

You May Be a Candidate for This Invisible No-Braces Treatment, Allesee Orthodontic Appliances-Pro Lab product information for patients, 2 pages (2002).
Ponitz, "Invisible Retainers," Am. J. Orthod., 59(3):266-272 (Mar. 1971).
Procera Research Projects, "Procera Research Projects 1993—Abstract Collection," pp. 3-7; 28 (1993).
Proffit et al., Contemporary Orthodontics, (Second Ed.), Chapter 15, Mosby Inc., pp. 470-533 (Oct. 1993.
Raintree Essix & Ars Materials, Inc., Raintree Essix, Technical Magazine Table of contents and Essix Appliances,< http:// www.essix.com/magazine/defaulthtml> Aug. 13, 1997.
Rapid prototyping. Protosys Technologies. 2005. http://www.protosystech.com/rapid-prototyping.htm. Accessed Jul. 1, 2015.
Redmond et al., "Clinical Implications of Digital Orthodontics," Am. J. Orthod. Dentofacial Orthop., 117(2):240-242 (2000).
Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).
Moles, "Correcting Mild Malalignments—As Easy As One, Two, Three," Aoa/Pro Corner, vol. 11, No. 1, 2 pages (2002).
Mormann et al., "Marginale Adaptation von adhasuven Porzellaninlays in vitro," Separatdruck aus: Schweiz. Mschr. Zahnmed. 95: 1118-1129, 1985.
Nahoum, "The Vacuum Formed Dental Contour Appliance," N. Y. State Dent. J., 30(9):385-390 (Nov. 1964).
Nash, "CEREC CAD/CAM Inlays: Aesthetics and Durability in a Single Appointment," Dent. Today, 9(8):20, 22-23 (Oct. 1990).
Nishiyama et al., "A New Construction of Tooth Repositioner by LTV Vinyl Silicone Rubber," J. Nihon Univ. Sch. Dent., 19(2):93-102 (1977).
Objet Geometries. Wikipedia. Last modified Jul. 17, 2014. https://en.wikipedia.org/wiki/Object_Geometries.
Orange Maker. High resolution 3D printing technology. 2015. http://www.orangemaker.com/. Accessed Jul. 1, 2015.
Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.
Pinkham, "Foolish Concept Propels Technology," Dentist, 3 pages total, Jan./Feb. 1989.
Pinkham, "Inventor's CAD/CAM May Transform Dentistry," Dentist, 3 pages total, Sep. 1990.
Sakuda et al., "Integrated Information-Processing System in Clinical Orthodontics: An Approach with Use of a Computer Network System," Am. J. Orthod. Dentofacial Orthop., 101(3): 210-220 (Mar. 1992).
Schellhas et al., "Three-Dimensional Computed Tomography in Maxillofacial Surgical Planning," Arch. Otolamp!. Head Neck Sur9., 114:438-442 (Apr. 1988).
Schroeder et al., Eds. The Visual Toolkit, Prentice Hall PTR, New Jersey (1998) Chapters 6, 8 & 9, (pp. 153-210,309-354, and 355-428, respectively.
Shilliday, (1971). Minimizing finishing problems with the mini-positioner, Am. J. Orthod. 59:596-599.
Siemens, "CEREC—Computer-Reconstruction," High Tech in der Zahnmedizin, 14 pages total (2004).
Sinclair, "The Readers' Corner," J. Clin. Orthod., 26(6):369-372 (Jun. 1992).
Sirona Dental Systems GmbH, CEREC 3D, Manuel utiiisateur, Version 2.0X (in French), 2003,114 pages total.
Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.
The Choice Is Clear: Red, White & Blue . . . The Simple, Affordable, No-Braces Treatment, Allesee HI Orthodontic Appliances—Pro Lab product information for doctors. http://ormco.com/aoa/appliancesservices/RWB/doctorhtml>, 5 pages (May 19, 2003).
Rekow, "CAD/CAM in Dentistry: A Historical Perspective and View of the Future," J. Can. Dent. Assoc., 58(4):283, 287-288 (Apr. 1992).
Rekow, "Computer-Aided Design and Manufacturing in Dentistry: A Review of the State of the Art," J. Prosthet. Dent., 58(4):512-516 (Oct. 1987).
Rekow, "Dental CAD-CAM Systems: What is the State of the Art?", J. Amer. Dent. Assoc., 122:43-48 1991.
Rekow et al., "CAD/CAM for Dental Restorations—Some of the Curious Challenges," IEEE Trans. Biomed. Eng., 38(4):314-318 (Apr. 1991).
Rekow et al., "Comparison of Three Data Acquisition Techniques for 3-D Tooth Surface Mapping," Annual International Conference of the IEEE Engineering in Medicine and Biology Society, 13(1):344-345 1991.
Rekow, "Feasibility of an Automated System for Production of Dental Restorations, Ph.D. Thesis," Univ. of Minnesota, 244 pages total, Nov. 1988.
Richmond et al., "The Development of a 3D Cast Analysis System," Br. J. Orthod., 13(1):53-54 (Jan. 1986).
Richmond et al., "The Development of the PAR Index (Peer Assessment Rating): Reliability and Validity," Eur. J. Orthod., 14:125-139 (1992).
Richmond, "Recording the Dental Cast in Three Dimensions," Am. J. Orthod. Dentofacial Orthop., 92(3):199-206 (Sep. 1987).
Rudge, "Dental Arch Analysis: Arch Form, a Review of the Literature," Eur. J. Orthod., 3(4):279-284 1981.
Van Der Linden, "A New Method to Determine Tooth Positions and Dental Arch Dimensions," J. Dent. Res., 51(4):1104 (Jul.-Aug. 1972).
Van Der Linden et al., "Three-Dimensional Analysis of Dental Casts by Means of the Optocom," J. Dent. Res., p. 1100 (Jul.-Aug. 1972).
Van Der Zel, "Ceramic-Fused-to-Metal Restorations with a New CAD/CAM System," Quintessence Int., 24(11):769-778 (1993.
Varady et al., "Reverse Engineering of Geometric Models—An Introduction," Computer-Aided Design, 29(4):255-268,1997.
Verstreken et al., "An Image-Guided Planning System for Endosseous Oral Implants," IEEE Trans. Med. Imaging, 17(5):842-852 (Oct. 1998).
Warunek et al., Physical and Mechanical Properties of Elastomers in Orthodonic Positioners, Am J. Orthod. Dentofac. Orthop, vol. 95, No. 5, (May 1989) pp. 399-400.
Warunek et.al., Clinical Use of Silicone Elastomer Applicances, JCO (1989) XXIII(10):694-700.
Wells, Application of the Positioner Appliance in Orthodontic Treatment, Am. J. Orthodont. (1970) 58:351-366.
Williams, "Dentistry and CAD/CAM: Another French Revolution," J. Dent. Practice Admin., pp. 2-5 (Jan./Mar. 1987).
Williams, "The Switzerland and Minnesota Developments in CAD/CAM," J. Dent. Practice Admin., pp. 50-55 (Apr./Jun. 1987).
The Choice is Clear: Red, White & Blue . . . The Simple, Affordable, No-Braces Treatment, Allesee HJ Orthodontic Appliances—Pro Lab product information for patients,< http://ormco.com/aoa/appliancesservices/RWB/patients.html>, 2 pages (May 19, 2003).
The Choice is Clear: Red, White & Blue . . . The Simple, Affordable, No-Braces Treatment, Allesee Orthodontic Appliances—Pro Lab product information, 6 pages (2003).
The Orange Maker Spins the Plate to Make Better 3D Prints. Newloop Tech and Gadgets. YouTube. Jul. 11, 2014. https://www.youtube.com/watch?v=MpzPWURWfZk.
The Red, White & Blue Way to Improve Your Smile! Allesee Orthodontic Appliances—Pro Lab product information for patients, 2 pages 1992.
Truax L., "Truax Clasp-Less(TM) Appliance System," Funct. Orthod., 9(5):22-4, 26-8 (Sep.-Oct. 1992).

(56) References Cited

OTHER PUBLICATIONS

Tru-Tain Orthodontic & Dental Supplies, Product Brochure, Rochester, Minnesota 55902, 16 pages total (1996).
U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050,342, filed Jun. 20, 1997, 41 pages total.
Yoshii, "Research on a New Orthodontic Appliance: The Dynamic Positioner (D.P.); III. The General Concept of the D.P. Method and Its Therapeutic Effect, Part 1, Dental and Functional Reversed Occlusion Case Reports," Nippon Dental Review, 457:146-164 (Nov. 1980).
Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.
WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.
Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).
Yamamoto et al., "Optical Measurement of Dental Cast Profile and Application to Analysis of Three-Dimensional Tooth Movement in Orthodontics," Front. Med. Biol. Eng., 1(2):119-130 (1988).
Yamamoto et al., "Three-Dimensional Measurement of Dental Cast Profiles and Its Applications to Orthodontics," Conf. Proc. IEEE Eng. Med. Biol. Soc., 12(5):2051-2053 (1990).
Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.
Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).
Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).

\* cited by examiner

DIRECT FABRICATION OF ALIGNERS FOR PALATE EXPANSION AND OTHER APPLICATIONS

CROSS-REFERENCE

This application claims the benefit of U.S. Provisional Application No. 62/189,271, filed Jul. 7, 2015, and U.S. Provisional Application No. 62/189,301, filed Jul. 7, 2015, the disclosures of each of which are incorporated herein by reference in their entirety.

The subject matter of the following patent applications is related to the present application: U.S. application Ser. No. 15/202,342, filed Jul. 5, 2016, entitled "MULTI-MATERIAL ALIGNERS", which claims the benefit of U.S. Provisional Application No. 62/189,259, filed Jul. 7, 2015 and U.S. Provisional Application No. 62/189,282, filed Jul. 7, 2015; U.S. application Ser. No. 15/202,472, filed Jul. 5, 2016, entitled "DIRECT FABRICATION OF ALIGNERS WITH INTERPROXIMAL FORCE COUPLING", which claims the benefit of U.S. Provisional Application No. 62/189,263, filed Jul. 7, 2015; U.S. application Ser. No. 15/202,452, filed Jul. 5, 2016, entitled "DIRECT FABRICATION OF ALIGNERS FOR ARCH EXPANSION", which claims the benefit of U.S. Provisional Application No. 62/189,271, filed Jul. 7, 2015, and U.S. Provisional Application No. 62/189,301, filed Jul. 7, 2015; U.S. application Ser. No. 15/202,348, filed Jul. 5, 2016, entitled "DIRECT FABRICATION OF ATTACHMENT TEMPLATES WITH ADHESIVE", which claimed the benefit of U.S. Provisional Application No. 62/189,259, filed Jul. 7, 2015, and U.S. Provisional Application No. 62/189,282, filed Jul. 7, 2015; U.S. application Ser. No. 15/202,254, filed Jul. 5, 2016, entitled "SYSTEMS, APPARATUSES AND METHODS FOR DENTAL APPLIANCES WITH INTEGRALLY FORMED FEATURES", which claims the benefit of U.S. Provisional Application No. 62/189,291, filed Jul. 7, 2015, U.S. Provisional Application No. 62/189,312, filed Jul. 7, 2015, and U.S. Provisional Application No. 62/189,317, filed Jul. 7, 2015; U.S. application Ser. No. 15/202,299, filed Jul. 5, 2016, entitled "DIRECT FABRICATION OF POWER ARMS", which claims the benefit of U.S. Provisional Application No. 62/189,291, filed Jul. 7, 2015, U.S. Provisional Application No. 62/189,312, filed Jul. 7, 2015, and U.S. Provisional Application No. 62/189,317, filed Jul. 7, 2015; U.S. application Ser. No. 15/202,187, filed Jul. 5, 2016, entitled "DIRECT FABRICATION OF ORTHODONTIC APPLIANCES WITH VARIABLE PROPERTIES", which claims the benefit of U.S. Provisional Application No. 62/189,291, filed Jul. 7, 2015, U.S. Provisional Application No. 62/189,312, filed Jul. 7, 2015, and U.S. Provisional Application No. 62/189,317, filed Jul. 7, 2015; U.S. application Ser. No. 15/202,139, filed Jul. 5, 2016, entitled "SYSTEMS, APPARATUSES AND METHODS FOR SUBSTANCE DELIVERY FROM DENTAL APPLIANCE", which claims the benefit of U.S. Provisional Application No. 62/189,303, filed Jul. 7, 2015; U.S. application Ser. No. 15/201,958, filed Jul. 5, 2016, entitled "DENTAL MATERIALS USING THERMOSET POLYMERS", which claims the benefit of U.S. Provisional Application No. 62/189,380, filed Jul. 7, 2015; and U.S. application Ser. No. 15/202,083, filed Jul. 5, 2016, entitled "DENTAL APPLIANCE HAVING ORNAMENTAL DESIGN", which claims the benefit of U.S. Provisional Application No. 62/189,318, filed Jul. 7, 2015, the entire disclosures of which are incorporated herein by reference.

BACKGROUND OF THE INVENTION

Prior methods and apparatus of expanding a patient's palate can be less than ideal in at least some instances. Prior palate expanders can be somewhat uncomfortable to wear. Work in relation to embodiments suggests that the fit of prior palate expanders to the patient can be less than ideal, and that this less than ideal fit can result in discomfort and decreased compliance with treatment. Also, prior methods and apparatus for fabricating palate expanders can be somewhat more time consuming and cost more than would be ideal, such that fewer people can benefit from the use of palate expanders. Furthermore, prior palate expanders require inconvenient adjustment on a daily or weekly basis by patients.

Additionally, some patients may have teeth arranged in a less than ideal manner, such that expansion of the arch with movement of the teeth can be helpful. Prior methods and apparatus for expanding a patient's arch can be less than ideal in at least some respects. Work in relation to embodiments suggests that the fit of prior arch expanders to the patient can be less than ideal, and that this less than ideal fit can result in discomfort and decreased compliance with treatment. Also, prior methods and apparatus for fabricating arch expanders can be somewhat more time consuming and cost more than would be ideal, such that fewer people can benefit from the use of arch expanders.

In light of the above there is a need for an improved, patient specific palate expanders and arch expanders having a better fit with the mouth of the patient, and designed to meet the patient's specific needs, which can be readily manufactured.

SUMMARY

In a first aspect, the methods and apparatus disclosed herein provide improved palate expanders having improved fit with the mouth of the patient. In many embodiments, the palate expander is customized to the dentitia and palate of the patient. The oral cavity of the patient can be scanned to determine the size and shape of at least the teeth of the upper arch and palate. The scans can provide three dimensional profile data of the upper teeth and palate, and this data can be used to determine the shape profile of the palate expander. The palate expander can be direct manufactured in accordance with the shape profile. The palate expander comprises a teeth-engaging portion and a force generating portion such as a resilient structure or a force generating portion. One or more extensions can extend between the teeth engaging portion and the force generating portion to couple the force generating portion of the teeth engaging portion. The teeth engaging portion may comprise a transparent shell having a plurality of tooth receiving cavities sized and shaped to receive a plurality of teeth of the patient. The force generating portion is configured to provide outward forces to the teeth to expand the palate. The force generating portion is sized and shaped to provide a gap between the palate and the force generating portion when the teeth engagement portion has been placed on and engages the teeth. The teeth engagement portion, the force generating portion and the extension portion can have three dimensional shape profiles determined in response to the three dimensional profile data of the mouth of the patient in order to customize the fit to the mouth. The force generating structure can be configured to provide a predetermined amount of force to the teeth on opposing sides of the upper arch in response to the three dimensional shape profile data. The force generating structure can be sized and shaped and configured with directly fabricated material to provide a customized amount of force to the mouth in response to the three dimensional profile data of the mouth.

The palate expander can be directly fabricated in order to fit the upper arch and palate and provide improved strength, accuracy, which can result in improved accuracy of the forces to the teeth, resulting in improved performance and comfort. Also, the palate expander can be accurately shaped to inhibit contact of the force generating portion with the palate. The three dimensional shape profile of the palate expander and can be determined in response to the three dimensional profile data. The direct manufacturing may comprise a continuous crosslinking process in which the force generating portion and the teeth engaging portion comprise crosslinked polymers and the force generating portion and the teeth engaging portion are connected together with cross-linking. This cross linking of these structures provides further improved accuracy of the forces to the teeth. The force generating portion and the teeth engaging portions may comprise similar polymers.

Alternatively the force generating portion and the teeth engaging portion may comprise different polymers.

The force generating portion can be configured in many ways. The force generating portion may comprise resilient structure such as a spring fabricated with direct manufacturing. The resilient structure can be configured in many ways and may comprise one or more of a coil, leaf springs, a chevron pattern, or bendable extensions. Alternatively or in combination, the force generating portion may comprise a hydratable polymer that swells when placed in the mouth and hydrated. The hydratable polymer may comprise a stiff polymer with sufficient rigidity to urge the teeth on opposing sides of the arch away from each other. The force generating portion may comprise a crosslinked polymer having less crosslinking than the tooth engagement portion, for example. The extensions, when included, may comprise more crosslinking than the force generating portion, for example. In many embodiments, the teeth engaging portion, the force generating portion and the extension portion comprise similar polymer material. The similar polymer material may have lesser amounts of cross-linking to provide the force generating portion. Varying the cross-linking as the palate expander is formed can allow the same prepolymer material to be used for the teeth engaging portions, the force generating portion and the extension portion. Using similar prepolymer material and polymer material for the teeth engaging portion, the force generating portion and the extension portion may have the advantage of increased strength and predictability. It is also contemplated, however, that different materials can be used to directly fabricate the palate expander.

In many embodiments, an appliance to expand a palate of a patient comprises a teeth engagement portion or component and a force generation portion or component. The teeth engaging component comprises a plurality of teeth engagement structures. The force generating component comprises a plurality of engagement structures to engage corresponding structures of the teeth engagement component in order to increase a size of the palate.

In many embodiments, an appliance to expand a palate of a patient comprises a teeth engaging component and a sintered metal force generating component. The teeth engaging component comprises a plurality of teeth engagement structures. The sintered metal force generating component comprises a plurality of engagement structures to engage corresponding structures of the teeth engagement component with force in order to increase a size of the palate.

The materials and structures as disclosed herein can be combined in many ways. The appliance may comprise sintered material such as a sintered metal and a sintered plastic material, for example, and combinations thereof.

The palate expander can be combined with orthodontic treatment. The palate expander may comprise a plurality of teeth receiving cavities sized and shaped to move the received teeth along a treatment profile. The palate expander may comprise one of a plurality of palate expanders comprising dental appliances having teeth receiving cavities sized and shaped to move teeth along an orthodontic treatment. The plurality of palate expanders can be applied in series and configured to expand the palate along a palate treatment plan with the teeth as the teeth are moved along a teeth treatment plan.

In a second aspect, the methods and apparatus disclosed herein provide improved arch expanders having improved fit with the mouth of the patient. In many embodiments, the arch expander is customized to the dentitia and arch of the patient. The oral cavity of the patient can be scanned to determine the size and shape of the teeth. The scans can provide three dimensional profile data of the teeth, and this data can be used to determine the shape profile of the arch expander. The arch expander can be direct manufactured in accordance with the shape profile. The arch expander may comprise a teeth retention portion to hold the appliance in place and a force generation portion to direct teeth movement to a desired position. The teeth retention portion may comprise a plurality of teeth engagement structures such as teeth receiving cavities or a plurality of extensions sized and shaped to extend at least partially around the teeth, for example around the teeth. The plurality of extension can extend into interproximal spaces of the teeth, and may comprise a soft material for patient comfort. The teeth retention portion may comprise a soft material, such as an elastic material. The force generating portion may comprise one or more of a stiff material or an expandable material, for example. The force generating portion may comprise a stiff material to engage the teeth and expand the arch. Alternatively or in combination, the force generating portion may comprise one or more of a compressible material, a resilient compressible structure, or a hydratable material to apply force to the teeth. The rigid material can extend between the force generating portion and the teeth to apply forces to the teeth expand the arch.

While the arch expander can be configured in many ways, the force generating structure can be located between a mesial component and a distal component in order to urge the teeth apart in mesial opposing mesial and distal directions. The expander may comprise adjacent stiff segments extending in mesial and distal directions, with the force generating structure located therebetween.

The arch expander may comprise retention structures with a soft material over the occlusal surface or no material over the occlusal surface to encourage tooth movement to a location suitable for engagement with an opposing tooth of an opposing arch.

The arch expander can be directly fabricated in order to fit the teeth and provide improved strength, accuracy, which can result in improved accuracy of the forces to the teeth, resulting in improved performance and comfort. The three dimensional shape profile of the arch expander can be determined in response to the three dimensional profile data.

The direct manufacturing may comprise a continuous crosslinking process in which the force generating portion and the teeth engaging portion comprise crosslinked polymers and the force generating portion and the teeth engaging portion are connected together with cross-linking. This cross linking of these structures provides further improved accuracy of the forces to the teeth. The force generating portion and the teeth engaging portions may comprise similar polymers. Alternatively the force generating portion and the teeth engaging portion may comprise different polymers. The teeth engaging portion may comprise a rigid material having structures sized and shaped to extend into the interproximal spaces of the teeth to improve engagement. Engagement of the teeth in the interproximal spaces permits application of forces closer to the center of rotation of the tooth in order to decrease tipping of the tooth.

Although many of the components disclosed herein can be fabricated together, in many embodiments components can be directly fabricated separately and provided with structures to allow coupling post fabrication. An appliance to expand an arch of a patient comprises a teeth engagement component and a force generating component. The teeth engagement component comprises a plurality of teeth engagement structures. The force generating component comprises a plurality of engagement structures to engage corresponding structures of the teeth engagement component to increase a size of the arch.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present disclosure will be obtained by reference to the following detailed description that sets forth illustrative embodiments, in which the principles of the invention are utilized, and the accompanying drawings of which:

DETAILED DESCRIPTION

Figure 1A:
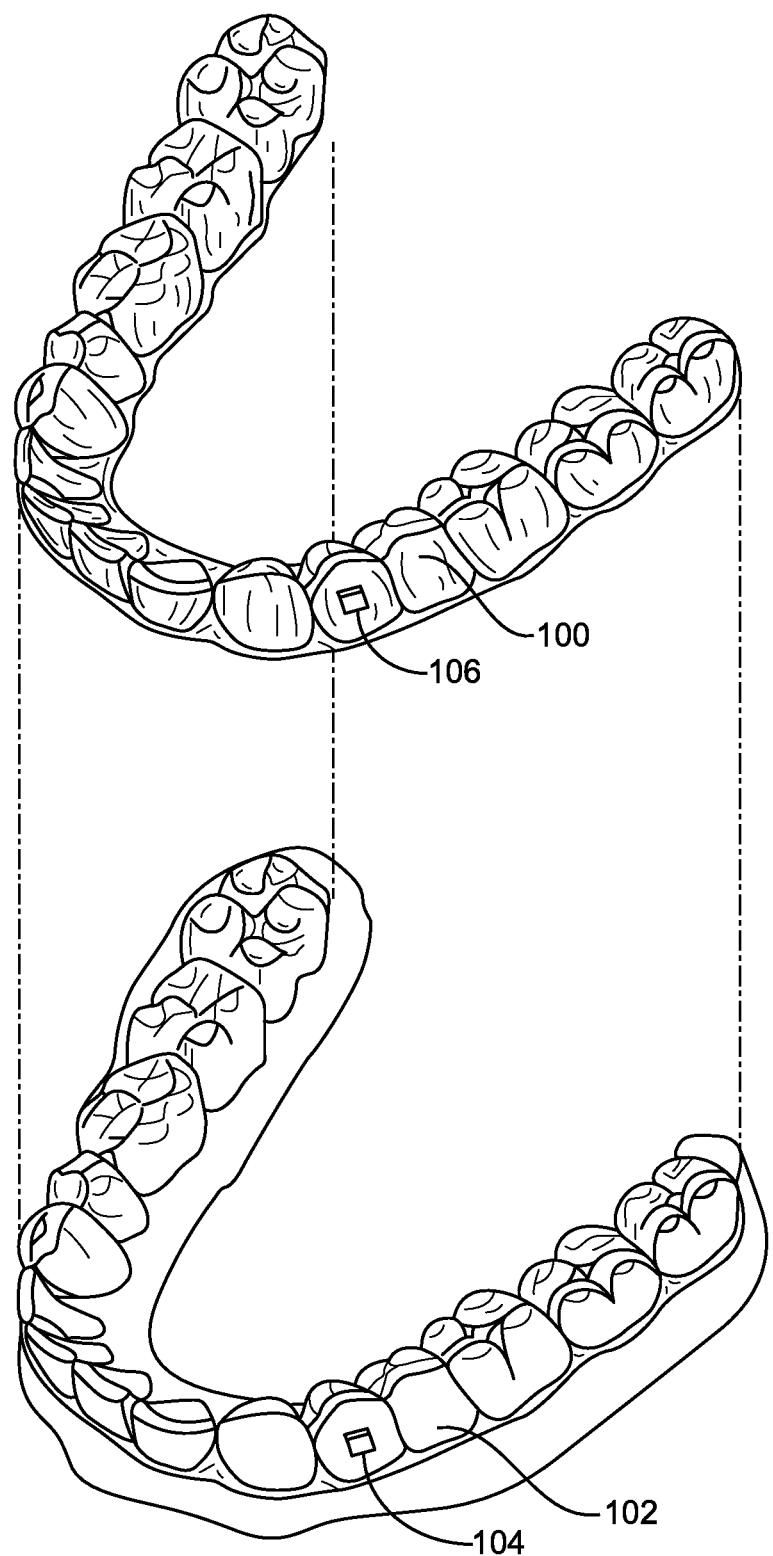
FIG. 1A illustrates a tooth repositioning appliance, in accordance with embodiments.

The entire disclosure of U.S. application Ser. No. 62/052,893, filed on Sep. 19, 2014, entitled "Arch Adjustment Appliance" is incorporated herein by reference and suitable for combination in accordance with embodiments disclosed herein.

In many embodiments, a directly fabricated orthodontic appliance for expanding a palate of a patient is provided. The appliance comprises a teeth engagement portion comprising a plurality of teeth engagement structures and a force generating portion coupled to the teeth engagement portion. The force generating portion comprises a hydratable polymer configured to expand when contacting saliva of the patient.

In some embodiments, the force generating portion is shaped to apply a palate-expanding force to the lateral sides of the palate of the patient when worn. In some embodiments, the force generating portion is configured to apply a palate-expanding force to the teeth engagement portion when worn, thereby applying a palate expanding force to the teeth of the patient. In some embodiments, the force generating portion is shaped to provide a gap between the top of the force generating portion and the palate when worn. In some cases, the teeth engagement portion and the force generating portion can comprise similar polymers with different amounts of crosslinking, the force generating portion comprising less crosslinking than the teeth engagement portion.

In many embodiments, a directly fabricated orthodontic appliance to expand a palate of a patient is provided. The appliance comprises a teeth engagement portion comprising a plurality of teeth engagement structures and a directly fabricated resilient structure coupled to the teeth engagement portion. In some cases, the resilient structure comprises one or more of a spring, a leaf spring, a coil spring, or an elastic structure.

In many embodiments, a directly fabricated appliance is provided for expanding a palate of a patient. The appliance comprises a teeth engagement component comprising a plurality of teeth receiving structures and a plurality of expander-engaging structures. The appliance further comprises an expander component comprising a plurality of engagement structures. The engagement structures of the expander component engage corresponding expander-engaging structures of the teeth engagement component. The engagement between the expander component and the teeth engagement component applies a force to increase a size of the palate when worn by the patient. In some cases, the respective engagement structures are reversibly couplable, such that the expander portion is removable from the appliance. In some embodiments, the appliance comprises a sintered expander or a sintered teeth engagement component. In some embodiments, the appliance comprises both a sintered expander and a sintered teeth engagement component, and each of the teeth engagement component and the expander component comprise a respective sintered material independently selected from sintered metal, sintered plastic, or a combination thereof.

In many embodiments, an appliance to expand a palate of a patient is provided comprising a teeth engagement component comprising a plurality of teeth receiving structures and an expander component coupled to the teeth engagement component. The expander component comprises a shape-memory material that changes from a first configuration to a second configuration in response to a change in temperature. In some cases, the appliance is configured to apply a greater palate expanding force in the first configuration than in the second configuration. In some cases, the shape-memory material takes on the first configuration at about room temperature and takes on the second configuration at about human body temperature.

In various embodiments, the appliances described herein can be shaped to be manually removable by the patient. In some embodiments, the teeth engagement portions of the appliances described herein can comprise a flattened occlusal surface for one or more molar-receiving structures. In various embodiments, the appliances described herein can be shaped to engage a temporary anchorage device in the palate of the patient to apply a palate expanding force when worn. In various embodiments, the appliances described herein can be configured to apply a tooth moving force to one or more anterior teeth of the upper arch while expanding the palate. In various embodiments, the appliances described herein can be configured to provide a palatal expansion selected from the group consisting of a slow palatal expansion and a rapid palatal expansion.

In various embodiments, the force generating portion of the appliances described herein is configured to have a target palatal displacement, and to apply a palatal expansion force to expand the palate to the target palatal displacement. In some cases, the target palatal displacement is adjustable.

In various embodiments, a plurality of the appliances described herein are provided. The plurality of appliances are configured to expand the palate when worn sequentially in accordance with a predetermined palate expansion plan.

In many embodiments, a method of fabricating an orthodontic appliance is provided. Scan data of an upper arch and a palate of a patient is received, and an amount of force to expand the palate is determined in response to the scan data. A shape profile of the appliance to engage teeth of the patient is determined and one or more of a force-generating or a resilient structure is selected to provide the force. Direct fabrication instructions are output to manufacture the appliance with the teeth engaging structure and the force generating or resilient structure.

In some cases, determining the shape profile includes determining a shape profile to inhibit contact with the top of the palate when worn. In some cases, the shape profile comprises an appliance shape to engage the lateral sides of the palate of the patient, and the amount of force comprises a first amount of force applied directly to the palate and a second amount of force applied to the teeth of the patient. In some cases, the force can comprise a force applied to a temporary anchorage device.

In some embodiments, the resilient structure comprises one or more of a spring, a leaf spring, a coil spring, or an elastic structure. In some embodiments, the force generating portion comprises one or more of a sintered plastic or a sintered metal comprising a material and size and shape profile arranged to increase a size of the palate and the teeth engaging portion comprises one or more of a sintered plastic or a sintered metal comprising a material and size and shape profile arranged to increase a size of the palate. In some embodiments, the method further comprises outputting direct fabrication instructions to manufacture a plurality of directly fabricated appliances configured to expand the palate in accordance with a predetermined palate expansion plan. In some cases, the plurality of directly fabricated appliances are further configured to move the teeth in accordance with a predetermined teeth movement treatment plan. In some cases, the plurality of directly fabricated appliances comprises a plurality of appliances configured to be placed on the teeth in series in accordance with a plurality of stages of a treatment plan.

In some embodiments, determining an amount of force comprises selecting a rate of palatal expansion based and determining a force to produce the selected rate of palatal expansion.

In some embodiments, the method further comprises directly manufacturing the appliance according to the direct fabrication instructions.

In some embodiments, the direct fabrication instructions include instructions to manufacture the appliance using an additive manufacturing process. In some cases, the additive manufacturing process comprises one or more of vat photopolymerization, material jetting, binder jetting, material extrusion, powder bed fusion, sheet lamination, or directed energy deposition. In some embodiments, the direct fabrication instructions include instructions to manufacture the appliance using a subtractive manufacturing process.

In various embodiments, the scan data can include data of a temporary anchorage device in the palate of the patient and the shape profile comprises an engagement structure to engage the temporary anchorage device to apply a palate expanding force when the appliance is worn.

In many embodiments, an apparatus to expand an arch of a patient is provided. The apparatus comprises a force generating portion to expand the arch of the teeth, a flexible retention portion to hold the force generating portion on the teeth, and a stiff retention portion coupled to the flexible retention portion. The stiff retention portion is positioned adjacent to a first plurality of teeth receiving structures of the flexible retention portion to receive a first plurality of teeth. The stiff retention portion resists movement of the first plurality of teeth while allowing movement of a second plurality of teeth when the apparatus is worn.

In some embodiments, the force generating portion, the flexible retention portion, and the stiff retention portion have been directly fabricated together. In some embodiments, the force generating portion comprises a stiff material. In some embodiments, the force generating portion comprises one or more of a compressible material or a resilient compressible structure to generate force to the teeth when placed. In some embodiments, the stiff retention portion comprises one or more ribs or thickened portions. In some embodiments, the force generating portion spans the space between the bicuspid or molar teeth. In some embodiments, the apparatus comprises a plurality of materials.

In some embodiments, the force generating portion comprises one or more of a compressible material, a hydratable material, or a resilient compressible structure to generate force to the teeth when worn. In some embodiments, the flexible retention portion comprises a plurality of teeth receiving structures, the plurality of teeth receiving structures comprising one or more of a plurality of teeth receiving cavities or a plurality of teeth receiving extensions shaped to extend at least partially around received teeth.

In some embodiments, the force generating portion comprises adjacent stiff segments separated in a mesial-distal direction with an expansion force generating portion extending therebetween. In some embodiments, the adjacent stiff segments comprise extensions sized to extend into interproximal portions to engage the teeth, and soft retention structures are affixed to the stiff segments and sized and shaped to extend around the teeth and into interproximal portions to engage the teeth and retain one or more stiff segments against the teeth.

In various embodiments, the apparatus described herein comprise one or more of a thermoplastic polymer, a thermoset polymer, a polymer ceramic composite, a carbon fiber composite, or a combination thereof.

In some embodiments, the apparatus is further configured to apply a tooth moving force to one or more anterior teeth of the arch while expanding the arch.

In many embodiments, a method of fabricating an appliance to expand an arch of a patient is provided. Scan data of teeth of an arch of the patient is received and a shape profile of the appliance to engage the teeth and expand the arch is determined. The appliance comprises a force generating portion to expand the arch of the teeth, a flexible retention portion to hold the force generating portion on the teeth, and a stiff retention portion coupled to the flexible retention portion. The stiff retention portion is positioned adjacent to a first plurality of teeth receiving structures of the flexible retention portion to receive a first plurality of teeth, to resist movement of the first plurality of teeth while allowing movement of a second plurality of teeth when the apparatus is worn. Direct fabrication instructions are output to manufacture the appliance with a direct fabrication apparatus.

In some embodiments, the method further comprises determining an amount of force to expand the arch in response to the scan data and determining a shape of the force generating portion to provide the force to the teeth.

In some embodiments, the force generating portion is stiffer than the flexible retention portion. In some cases, the force generating portion comprises adjacent stiff segments separated in a mesial-distal direction with an expansion force generating portion extending therebetween. In some cases, the appliance is configured to expand the arch with increasing separation of the adjacent stiff segments in a mesial-distal direction, and the adjacent stiff segments comprise extensions sized to extend into interproximal portions to engage the teeth. In some cases, the appliance further comprises soft retention structures affixed to the stiff segments and sized and shaped to extend around the teeth and into interproximal portions to engage the teeth and retain one or more stiff segments against the teeth.

In some embodiments, the method further comprises directly manufacturing the appliance according to the direct fabrication instructions. In some embodiments, the direct fabrication instructions include instructions to manufacture the appliance using an additive manufacturing process. In some cases, the additive manufacturing process comprises one or more of vat photopolymerization, material jetting, binder jetting, material extrusion, powder bed fusion, sheet lamination, or directed energy deposition. In some embodiments, the direct fabrication instructions include instructions to manufacture the appliance using a subtractive manufacturing process.

In many embodiments, an appliance to expand an arch of a patient is provided. The appliance comprises a teeth engagement component comprising a plurality of teeth engagement structures and a force generating component coupled to the teeth engagement component. The teeth engagement component comprises a plurality of structures disposed on the lingual side of the teeth engagement component, and the force generating component comprises a plurality of engagement structures to engage the structures of the teeth engagement component to apply an arch expanding force.

In some embodiments, the force generating component is a sintered metal or sintered plastic force generating component comprising a plurality of engagement structures to engage corresponding structures of the teeth engagement component with force in order to increase a size of the arch. In some embodiments, the teeth engagement component is a sintered metal or sintered plastic teeth engagement component.

As used herein the terms "rigidity" and "stiffness" are used interchangeably, as are the corresponding terms "rigid" and "stiff."

As used herein the term "and/or" is used as a functional word to indicate that two words or expressions are to be taken together or individually. For example, A and/or B encompasses A alone, B alone, and A and B together.

As used herein a "plurality of teeth" encompasses two or more teeth.

In many embodiments, one or more posterior teeth comprises one or more of a molar, a premolar or a canine, and one or more anterior teeth comprising one or more of a central incisor, a lateral incisor, a cuspid, a first bicuspid or a second bicuspid.

The embodiments disclosed herein can be used to couple groups of one or more teeth to each other. The groups of one or more teeth may comprise a first group of one or more anterior teeth and a second group of one or more posterior teeth. The first group of teeth can be coupled to the second group of teeth with the polymeric shell appliances as disclosed herein.

The embodiments disclosed herein are well suited for moving one or more teeth of the first group of one or more teeth or moving one or more of the second group of one or more teeth, and combinations thereof.

The embodiments disclosed herein are well suited for combination with one or known commercially available tooth moving components such as attachments and polymeric shell appliances. In many embodiments, the appliance and one or more attachments are configured to move one or more teeth along a tooth movement vector comprising six degrees of freedom, in which three degrees of freedom are rotational and three degrees of freedom are translation.

The present disclosure provides orthodontic systems and related methods for designing and providing improved or more effective tooth moving systems for eliciting a desired tooth movement and/or repositioning teeth into a desired arrangement.

Although reference is made to an appliance comprising a polymeric shell appliance, the embodiments disclosed herein are well suited for use with many appliances that receive teeth, for example appliances without one or more of polymers or shells. The appliance can be fabricated with one or more of many materials such as metal, glass, reinforced fibers, carbon fiber, composites, reinforced composites, aluminum, biological materials, and combinations thereof for example. In some cases, the reinforced composites can comprise a polymer matrix reinforced with ceramic or metallic particles, for example. The appliance can be shaped in many ways, such as with thermoforming or direct fabrication as described herein, for example. Alternatively or in combination, the appliance can be fabricated with machining such as an appliance fabricated from a block of material with computer numeric control machining.

Turning now to the drawings, in which like numbers designate like elements in the various figures, FIG. 1A illustrates an exemplary tooth repositioning appliance or aligner 100 that can be worn by a patient in order to achieve an incremental repositioning of individual teeth 102 in the jaw. The appliance can include a shell (e.g., a continuous polymeric shell or a segmented shell) having teeth-receiving cavities that receive and resiliently reposition the teeth. An appliance or portion(s) thereof may be indirectly fabricated using a physical model of teeth. For example, an appliance (e.g., polymeric appliance) can be formed using a physical model of teeth and a sheet of suitable layers of polymeric material. In some embodiments, a physical appliance is directly fabricated, e.g., using rapid prototyping fabrication techniques, from a digital model of an appliance. An appliance can fit over all teeth present in an upper or lower jaw, or less than all of the teeth. The appliance can be designed specifically to accommodate the teeth of the patient (e.g., the topography of the tooth-receiving cavities matches the topography of the patient's teeth), and may be fabricated based on positive or negative models of the patient's teeth generated by impression, scanning, and the like. Alternatively, the appliance can be a generic appliance configured to receive the teeth, but not necessarily shaped to match the topography of the patient's teeth. In some cases, only certain teeth received by an appliance will be repositioned by the appliance while other teeth can provide a base or anchor region for holding the appliance in place as it applies force against the tooth or teeth targeted for repositioning. In some cases, some, most, or even all of the teeth will be repositioned at some point during treatment. Teeth that are moved can also serve as a base or anchor for holding the appliance as it is worn by the patient. Typically, no wires or other means will be provided for holding an appliance in place over the teeth. In some cases, however, it may be desirable or necessary to provide individual attachments or other anchoring elements 104 on teeth 102 with corresponding receptacles or apertures 106 in the appliance 100 so that the appliance can apply a selected force on the tooth. Exemplary appliances, including those utilized in the Invisalign® System, are described in numerous patents and patent applications assigned to Align Technology, Inc. including, for example, in U.S. Pat. Nos. 6,450,807, and 5,975,893, as well as on the company's website, which is accessible on the World Wide Web (see, e.g., the url "invisalign.com"). Examples of tooth-mounted attachments suitable for use with orthodontic appliances are also described in patents and patent applications assigned to Align Technology, Inc., including, for example, U.S. Pat. Nos. 6,309,215 and 6,830,450.

Figure 1B:
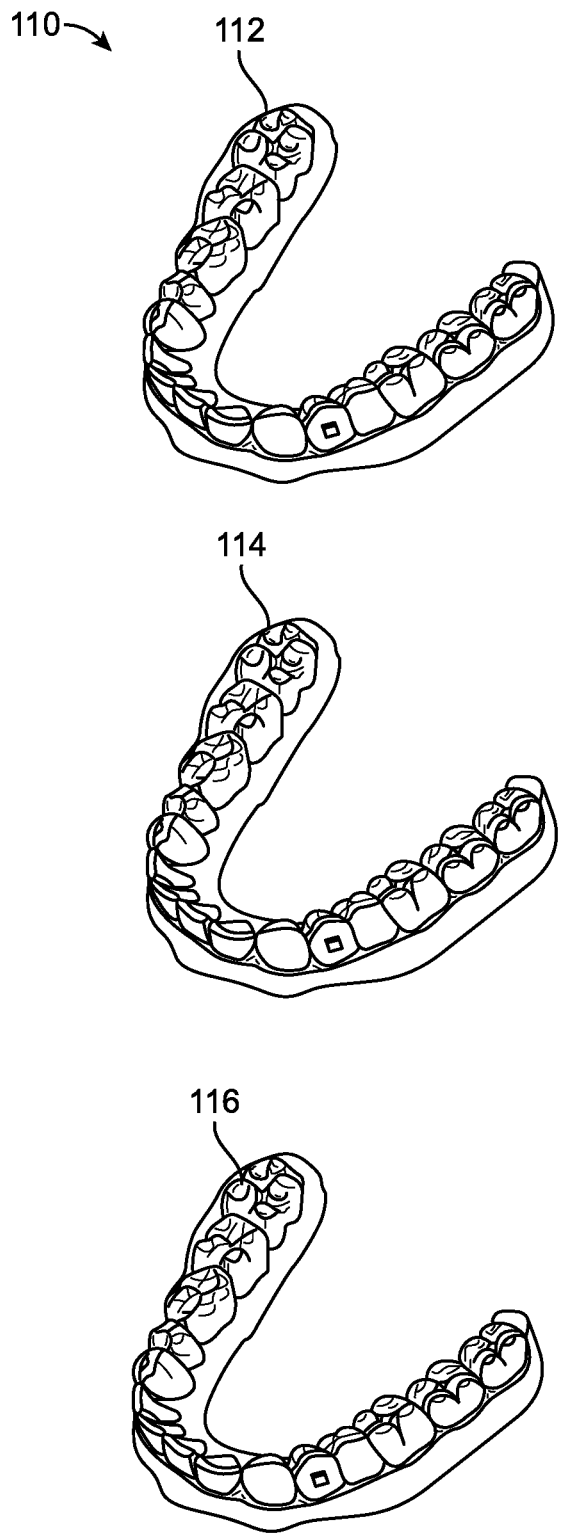
FIG. 1B illustrates a tooth repositioning system, in accordance with embodiments.

FIG. 1B illustrates a tooth repositioning system 110 including a plurality of appliances 112, 114, 116. Any of the appliances described herein can be designed and/or provided as part of a set of a plurality of appliances used in a tooth repositioning system. Each appliance may be configured so a tooth-receiving cavity has a geometry corresponding to an intermediate or final tooth arrangement intended for the appliance. The patient's teeth can be progressively repositioned from an initial tooth arrangement to a target tooth arrangement by placing a series of incremental position adjustment appliances over the patient's teeth. For example, the tooth repositioning system 110 can include a first appliance 112 corresponding to an initial tooth arrangement, one or more intermediate appliances 114 corresponding to one or more intermediate arrangements, and a final appliance 116 corresponding to a target arrangement. A target tooth arrangement can be a planned final tooth arrangement selected for the patient's teeth at the end of all planned orthodontic treatment. Alternatively, a target arrangement can be one of some intermediate arrangements for the patient's teeth during the course of orthodontic treatment, which may include various different treatment scenarios, including, but not limited to, instances where surgery is recommended, where interproximal reduction (IPR) is appropriate, where a progress check is scheduled, where anchor placement is best, where palatal expansion is desirable, where restorative dentistry is involved (e.g., inlays, onlays, crowns, bridges, implants, veneers, and the like), etc. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages.

Figure 1C:
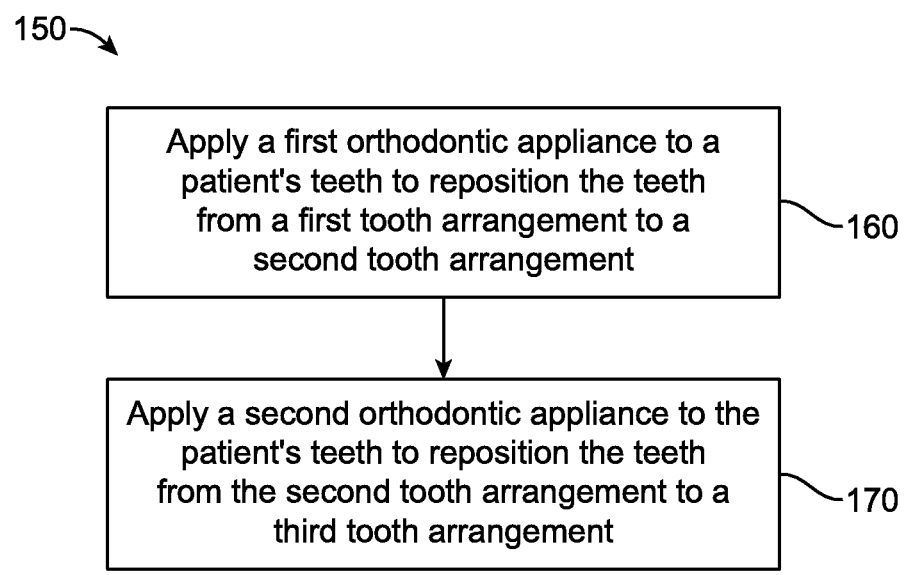
FIG. 1C illustrates a method of orthodontic treatment using a plurality of appliances, in accordance with embodiments.

FIG. 1C illustrates a method 150 of orthodontic treatment using a plurality of appliances, in accordance with embodiments. The method 150 can be practiced using any of the appliances or appliance sets described herein. In step 160, a first orthodontic appliance is applied to a patient's teeth in order to reposition the teeth from a first tooth arrangement to a second tooth arrangement. In step 170, a second orthodontic appliance is applied to the patient's teeth in order to reposition the teeth from the second tooth arrangement to a third tooth arrangement. The method 150 can be repeated as necessary using any suitable number and combination of sequential appliances in order to incrementally reposition the patient's teeth from an initial arrangement to a target arrangement. The appliances can be generated all at the same stage or in sets or batches (e.g., at the beginning of a stage of the treatment), or the appliances can be fabricated one at a time, and the patient can wear each appliance until the pressure of each appliance on the teeth can no longer be felt or until the maximum amount of expressed tooth movement for that given stage has been achieved. A plurality of different appliances (e.g., a set) can be designed and even fabricated prior to the patient wearing any appliance of the plurality. After wearing an appliance for an appropriate period of time, the patient can replace the current appliance with the next appliance in the series until no more appliances remain. The appliances are generally not affixed to the teeth and the patient may place and replace the appliances at any time during the procedure (e.g., patient-removable appliances). The final appliance or several appliances in the series may have a geometry or geometries selected to overcorrect the tooth arrangement. For instance, one or more appliances may have a geometry that would (if fully achieved) move individual teeth beyond the tooth arrangement that has been selected as the "final." Such over-correction may be desirable in order to offset potential relapse after the repositioning method has been terminated (e.g., permit movement of individual teeth back toward their pre-corrected positions). Over-correction may also be beneficial to speed the rate of correction (e.g., an appliance with a geometry that is positioned beyond a desired intermediate or final position may shift the individual teeth toward the position at a greater rate). In such cases, the use of an appliance can be terminated before the teeth reach the positions defined by the appliance. Furthermore, over-correction may be deliberately applied in order to compensate for any inaccuracies or limitations of the appliance.

The various embodiments of the orthodontic appliances presented herein can be fabricated in a wide variety of ways. In some embodiments, the orthodontic appliances herein (or portions thereof) can be produced using direct fabrication, such as additive manufacturing techniques (also referred to herein as "3D printing) or subtractive manufacturing techniques (e.g., milling). In some embodiments, direct fabrication involves forming an object (e.g., an orthodontic appliance or a portion thereof) without using a physical template (e.g., mold, mask etc.) to define the object geometry. Additive manufacturing techniques can be categorized as follows: (1) vat photopolymerization (e.g., stereolithography), in which an object is constructed layer by layer from a vat of liquid photopolymer resin; (2) material jetting, in which material is jetted onto a build platform using either a continuous or drop on demand (DOD) approach; (3) binder jetting, in which alternating layers of a build material (e.g., a powder-based material) and a binding material (e.g., a liquid binder) are deposited by a print head; (4) fused deposition modeling (FDM), in which material is drawn though a nozzle, heated, and deposited layer by layer; (5) powder bed fusion, including but not limited to direct metal laser sintering (DMLS), electron beam melting (EBM), selective heat sintering (SHS), selective laser melting (SLM), and selective laser sintering (SLS); (6) sheet lamination, including but not limited to laminated object manufacturing (LOM) and ultrasonic additive manufacturing (UAM); and (7) directed energy deposition, including but not limited to laser engineering net shaping, directed light fabrication, direct metal deposition, and 3D laser cladding. For example, stereolithography can be used to directly fabricate one or more of the appliances herein. In some embodiments, stereolithography involves selective polymerization of a photosensitive resin (e.g., a photopolymer) according to a desired cross-sectional shape using light (e.g., ultraviolet light). The object geometry can be built up in a layer-by-layer fashion by sequentially polymerizing a plurality of object cross-sections. As another example, the appliances herein can be directly fabricated using selective laser sintering. In some embodiments, selective laser sintering involves using a laser beam to selectively melt and fuse a layer of powdered material according to a desired cross-sectional shape in order to build up the object geometry. As yet another example, the appliances herein can be directly fabricated by fused deposition modeling. In some embodiments, fused deposition modeling involves melting and selectively depositing a thin filament of thermoplastic polymer in a layer-by-layer manner in order to form an object. In yet another example, material jetting can be used to directly fabricate the appliances herein. In some embodiments, material jetting involves jetting or extruding one or more materials onto a build surface in order to form successive layers of the object geometry.

Alternatively or in combination, some embodiments of the appliances herein (or portions thereof) can be produced using indirect fabrication techniques, such as by thermoforming over a positive or negative mold. Indirect fabrication of an orthodontic appliance can involve producing a positive or negative mold of the patient's dentition in a target arrangement (e.g., by rapid prototyping, milling, etc.) and thermoforming one or more sheets of material over the mold in order to generate an appliance shell.

In some embodiments, the direct fabrication methods provided herein build up the object geometry in a layer-by-layer fashion, with successive layers being formed in discrete build steps. Alternatively or in combination, direct fabrication methods that allow for continuous build-up of an object geometry can be used, referred to herein as "continuous direct fabrication." Various types of continuous direct fabrication methods can be used. As an example, in some embodiments, the appliances herein are fabricated using "continuous liquid interphase printing," in which an object is continuously built up from a reservoir of photopolymerizable resin by forming a gradient of partially cured resin between the building surface of the object and a polymerization-inhibited "dead zone." In some embodiments, a semipermeable membrane is used to control transport of a photopolymerization inhibitor (e.g., oxygen) into the dead zone in order to form the polymerization gradient. Continuous liquid interphase printing can achieve fabrication speeds about 25 times to about 100 times faster than other direct fabrication methods, and speeds about 1000 times faster can be achieved with the incorporation of cooling systems. Continuous liquid interphase printing is described in U.S. Patent Publication Nos. 2015/0097315, 2015/0097316, and 2015/0102532, the disclosures of each of which are incorporated herein by reference in their entirety.

As another example, a continuous direct fabrication method can achieve continuous build-up of an object geometry by continuous movement of the build platform (e.g., along the vertical or Z-direction) during the irradiation phase, such that the hardening depth of the irradiated photopolymer is controlled by the movement speed. Accordingly, continuous polymerization of material on the build surface can be achieved. Such methods are described in U.S. Pat. No. 7,892,474, the disclosure of which is incorporated herein by reference in its entirety.

In another example, a continuous direct fabrication method can involve extruding a composite material composed of a curable liquid material surrounding a solid strand. The composite material can be extruded along a continuous three-dimensional path in order to form the object. Such methods are described in U.S. Patent Publication No. 2014/0061974, the disclosure of which is incorporated herein by reference in its entirety.

In yet another example, a continuous direct fabrication method utilizes a "heliolithography" approach in which the liquid photopolymer is cured with focused radiation while the build platform is continuously rotated and raised. Accordingly, the object geometry can be continuously built up along a spiral build path. Such methods are described in U.S. Patent Publication No. 2014/0265034, the disclosure of which is incorporated herein by reference in its entirety.

The direct fabrication approaches provided herein are compatible with a wide variety of materials, including but not limited to one or more of the following: a polyester, a co-polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, a polytrimethylene terephthalate, a styrenic block copolymer (SBC), a silicone rubber, an elastomeric alloy, a thermoplastic elastomer (TPE), a thermoplastic vulcanizate (TPV) elastomer, a polyurethane elastomer, a block copolymer elastomer, a polyolefin blend elastomer, a thermoplastic co-polyester elastomer, a thermoplastic polyamide elastomer, a thermoset material, or combinations thereof. The materials used for direct fabrication can be provided in an uncured form (e.g., as a liquid, resin, powder, etc.) and can be cured (e.g., by photopolymerization, light curing, gas curing, laser curing, crosslinking, etc.) in order to form an orthodontic appliance or a portion thereof. The properties of the material before curing may differ from the properties of the material after curing. Once cured, the materials herein can exhibit sufficient strength, stiffness, durability, biocompatibility, etc. for use in an orthodontic appliance. The post-curing properties of the materials used can be selected according to the desired properties for the corresponding portions of the appliance.

In some embodiments, relatively rigid portions of the orthodontic appliance can be formed via direct fabrication using one or more of the following materials: a polyester, a co-polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, and/or a polytrimethylene terephthalate.

In some embodiments, relatively elastic portions of the orthodontic appliance can be formed via direct fabrication using one or more of the following materials: a styrenic block copolymer (SBC), a silicone rubber, an elastomeric alloy, a thermoplastic elastomer (TPE), a thermoplastic vulcanizate (TPV) elastomer, a polyurethane elastomer, a block copolymer elastomer, a polyolefin blend elastomer, a thermoplastic co-polyester elastomer, and/or a thermoplastic polyamide elastomer.

Machine parameters can include curing parameters. For digital light processing (DLP)-based curing systems, curing parameters can include power, curing time, and/or grayscale of the full image. For laser-based curing systems, curing parameters can include power, speed, beam size, beam shape and/or power distribution of the beam. For printing systems, curing parameters can include material drop size, viscosity, and/or curing power. These machine parameters can be monitored and adjusted on a regular basis (e.g., some parameters at every 1-x layers and some parameters after each build) as part of the process control on the fabrication machine. Process control can be achieved by including a sensor on the machine that measures power and other beam parameters every layer or every few seconds and automatically adjusts them with a feedback loop. For DLP machines, gray scale can be measured and calibrated before, during, and/or at the end of each build, and/or at predetermined time intervals (e.g., every $n^{th}$ build, once per hour, once per day, once per week, etc.), depending on the stability of the system. In addition, material properties and/or photo-characteristics can be provided to the fabrication machine, and a machine process control module can use these parameters to adjust machine parameters (e.g., power, time, gray scale, etc.) to compensate for variability in material properties. By implementing process controls for the fabrication machine, reduced variability in appliance accuracy and residual stress can be achieved.

Optionally, the direct fabrication methods described herein allow for fabrication of an appliance including multiple materials, referred to herein as "multi-material direct fabrication." In some embodiments, a multi-material direct fabrication method involves concurrently forming an object from multiple materials in a single manufacturing step. For instance, a multi-tip extrusion apparatus can be used to selectively dispense multiple types of materials from distinct material supply sources in order to fabricate an object from a plurality of different materials. Such methods are described in U.S. Pat. No. 6,749,414, the disclosure of which is incorporated herein by reference in its entirety. Alternatively or in combination, a multi-material direct fabrication method can involve forming an object from multiple materials in a plurality of sequential manufacturing steps. For instance, a first portion of the object can be formed from a first material in accordance with any of the direct fabrication methods herein, then a second portion of the object can be formed from a second material in accordance with methods herein, and so on, until the entirety of the object has been formed.

Direct fabrication can provide various advantages compared to other manufacturing approaches. For instance, in contrast to indirect fabrication, direct fabrication permits production of an orthodontic appliance without utilizing any molds or templates for shaping the appliance, thus reducing the number of manufacturing steps involved and improving the resolution and accuracy of the final appliance geometry. Additionally, direct fabrication permits precise control over the three-dimensional geometry of the appliance, such as the appliance thickness. Complex structures and/or auxiliary components can be formed integrally as a single piece with the appliance shell in a single manufacturing step, rather than being added to the shell in a separate manufacturing step. In some embodiments, direct fabrication is used to produce appliance geometries that would be difficult to create using alternative manufacturing techniques, such as appliances with very small or fine features, complex geometric shapes, undercuts, interproximal structures, shells with variable thicknesses, and/or internal structures (e.g., for improving strength with reduced weight and material usage). For example, in some embodiments, the direct fabrication approaches herein permit fabrication of an orthodontic appliance with feature sizes of less than or equal to about 5 µm, or within a range from about 5 µm to about 50 µm, or within a range from about 20 µm to about 50 µm.

The direct fabrication techniques described herein can be used to produce appliances with substantially isotropic material properties, e.g., substantially the same or similar strengths along all directions. In some embodiments, the direct fabrication approaches herein permit production of an orthodontic appliance with a strength that varies by no more than about 25%, about 20%, about 15%, about 10%, about 5%, about 1%, or about 0.5% along all directions. Additionally, the direct fabrication approaches herein can be used to produce orthodontic appliances at a faster speed compared to other manufacturing techniques. In some embodiments, the direct fabrication approaches herein allow for production of an orthodontic appliance in a time interval less than or equal to about 1 hour, about 30 minutes, about 25 minutes, about 20 minutes, about 15 minutes, about 10 minutes, about 5 minutes, about 4 minutes, about 3 minutes, about 2 minutes, about 1 minutes, or about 30 seconds. Such manufacturing speeds allow for rapid "chair-side" production of customized appliances, e.g., during a routine appointment or checkup.

In some embodiments, the direct fabrication methods described herein implement process controls for various machine parameters of a direct fabrication system or device in order to ensure that the resultant appliances are fabricated with a high degree of precision. Such precision can be beneficial for ensuring accurate delivery of a desired force system to the teeth in order to effectively elicit tooth movements. Process controls can be implemented to account for process variability arising from multiple sources, such as the material properties, machine parameters, environmental variables, and/or post-processing parameters.

Material properties may vary depending on the properties of raw materials, purity of raw materials, and/or process variables during mixing of the raw materials. In many embodiments, resins or other materials for direct fabrication should be manufactured with tight process control to ensure little variability in photo-characteristics, material properties (e.g., viscosity, surface tension), physical properties (e.g., modulus, strength, elongation) and/or thermal properties (e.g., glass transition temperature, heat deflection temperature). Process control for a material manufacturing process can be achieved with screening of raw materials for physical properties and/or control of temperature, humidity, and/or other process parameters during the mixing process. By implementing process controls for the material manufacturing procedure, reduced variability of process parameters and more uniform material properties for each batch of material can be achieved. Residual variability in material properties can be compensated with process control on the machine, as discussed further herein.

Machine parameters can include curing parameters. For digital light processing (DLP)-based curing systems, curing parameters can include power, curing time, and/or grayscale of the full image. For laser-based curing systems, curing parameters can include power, speed, beam size, beam shape and/or power distribution of the beam. For printing systems, curing parameters can include material drop size, viscosity, and/or curing power. These machine parameters can be monitored and adjusted on a regular basis (e.g., some parameters at every 1-x layers and some parameters after each build) as part of the process control on the fabrication machine. Process control can be achieved by including a sensor on the machine that measures power and other beam parameters every layer or every few seconds and automatically adjusts them with a feedback loop. For DLP machines, gray scale can be measured and calibrated at the end of each build. In addition, material properties and/or photo-characteristics can be provided to the fabrication machine, and a machine process control module can use these parameters to adjust machine parameters (e.g., power, time, gray scale, etc.) to compensate for variability in material properties. By implementing process controls for the fabrication machine, reduced variability in appliance accuracy and residual stress can be achieved.

In many embodiments, environmental variables (e.g., temperature, humidity, Sunlight or exposure to other energy/curing source) are maintained in a tight range to reduce variable in appliance thickness and/or other properties. Optionally, machine parameters can be adjusted to compensate for environmental variables.

In many embodiments, post-processing of appliances includes cleaning, post-curing, and/or support removal processes. Relevant post-processing parameters can include purity of cleaning agent, cleaning pressure and/or temperature, cleaning time, post-curing energy and/or time, and/or consistency of support removal process. These parameters can be measured and adjusted as part of a process control scheme. In addition, appliance physical properties can be varied by modifying the post-processing parameters. Adjusting post-processing machine parameters can provide another way to compensate for variability in material properties and/or machine properties.

The configuration of the orthodontic appliances herein can be determined according to a treatment plan for a patient, e.g., a treatment plan involving successive administration of a plurality of appliances for incrementally repositioning teeth. Computer-based treatment planning and/or appliance manufacturing methods can be used in order to facilitate the design and fabrication of appliances. For instance, one or more of the appliance components described herein can be digitally designed and fabricated with the aid of computer-controlled manufacturing devices (e.g., computer numerical control (CNC) milling, computer-controlled rapid prototyping such as 3D printing, etc.). The computer-based methods presented herein can improve the accuracy, flexibility, and convenience of appliance fabrication.

Figure 2:
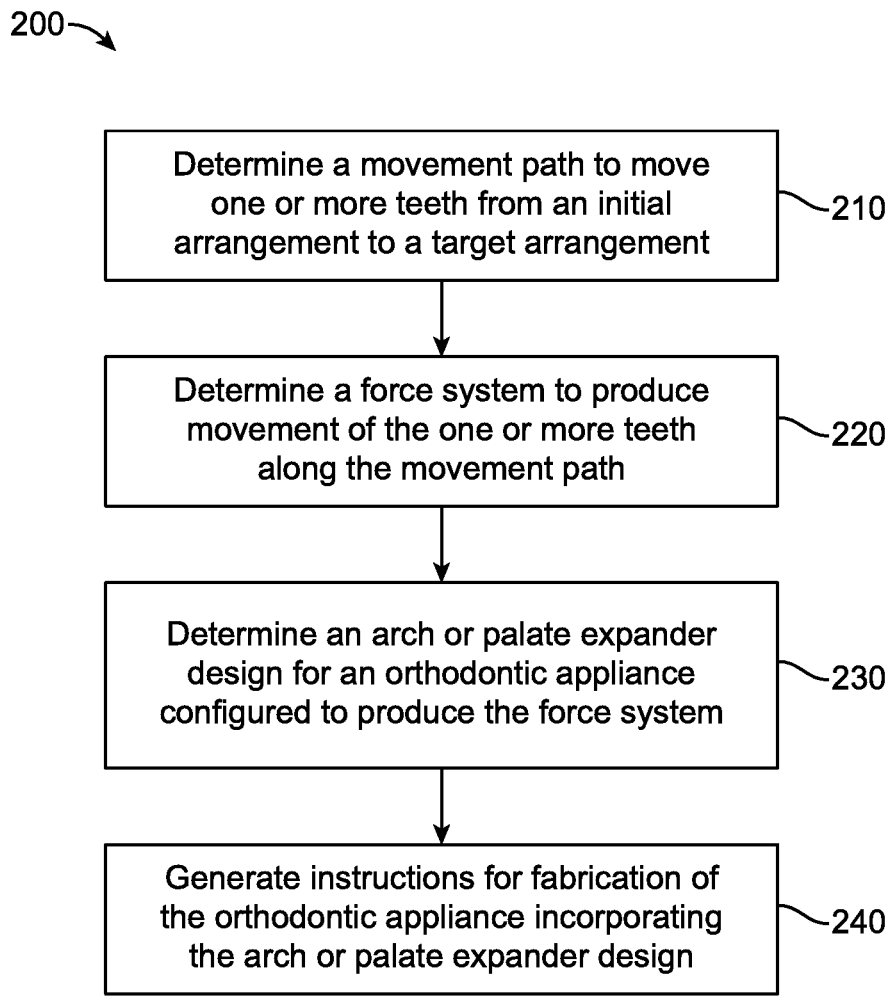
FIG. 2 illustrates a method for designing an orthodontic appliance, in accordance with embodiments.

FIG. 2 illustrates a method 200 for designing an orthodontic appliance to be produced by direct fabrication, in accordance with embodiments. The method 200 can be applied to any embodiment of the orthodontic appliances described herein. Some or all of the steps of the method 200 can be performed by any suitable data processing system or device, e.g., one or more processors configured with suitable instructions.

In step 210, a movement path to move one or more teeth from an initial arrangement to a target arrangement is determined. The initial arrangement can be determined from a mold or a scan of the patient's teeth or mouth tissue, e.g., using wax bites, direct contact scanning, x-ray imaging, tomographic imaging, sonographic imaging, and other techniques for obtaining information about the position and structure of the teeth, jaws, gums and other orthodontically relevant tissue. From the obtained data, a digital data set can be derived that represents the initial (e.g., pretreatment) arrangement of the patient's teeth and other tissues. Optionally, the initial digital data set is processed to segment the tissue constituents from each other. For example, data structures that digitally represent individual tooth crowns can be produced. Advantageously, digital models of entire teeth can be produced, including measured or extrapolated hidden surfaces and root structures, as well as surrounding bone and soft tissue.

The target arrangement of the teeth (e.g., a desired and intended end result of orthodontic treatment) can be received from a clinician in the form of a prescription, can be calculated from basic orthodontic principles, and/or can be extrapolated computationally from a clinical prescription. With a specification of the desired final positions of the teeth and a digital representation of the teeth themselves, the final position and surface geometry of each tooth can be specified to form a complete model of the tooth arrangement at the desired end of treatment.

Having both an initial position and a target position for each tooth, a movement path can be defined for the motion of each tooth. In some embodiments, the movement paths are configured to move the teeth in the quickest fashion with the least amount of round-tripping to bring the teeth from their initial positions to their desired target positions. The tooth paths can optionally be segmented, and the segments can be calculated so that each tooth's motion within a segment stays within threshold limits of linear and rotational translation. In this way, the end points of each path segment can constitute a clinically viable repositioning, and the aggregate of segment end points can constitute a clinically viable sequence of tooth positions, so that moving from one point to the next in the sequence does not result in a collision of teeth.

In step 220, a force system to produce movement of the one or more teeth along the movement path is determined. A force system can include one or more forces and/or one or more torques. Different force systems can result in different types of tooth movement, such as tipping, translation, rotation, extrusion, intrusion, root movement, etc. Biomechanical principles, modeling techniques, force calculation/measurement techniques, and the like, including knowledge and approaches commonly used in orthodontia, may be used to determine the appropriate force system to be applied to the tooth to accomplish the tooth movement. In determining the force system to be applied, sources may be considered including literature, force systems determined by experimentation or virtual modeling, computer-based modeling, clinical experience, minimization of unwanted forces, etc.

The determination of the force system can include constraints on the allowable forces, such as allowable directions and magnitudes, as well as desired motions to be brought about by the applied forces. For example, in fabricating palatal expanders, different movement strategies may be desired for different patients. For example, the amount of force needed to separate the palate can depend on the age of the patient, as very young patients may not have a fully-formed suture. Thus, in juvenile patients and others without fully-closed palatal sutures, palatal expansion can be accomplished with lower force magnitudes. Slower palatal movement can also aid in growing bone to fill the expanding suture. For other patients, a more rapid expansion may be desired, which can be achieved by applying larger forces. These requirements can be incorporated as needed to choose the structure and materials of appliances; for example, by choosing palatal expanders capable of applying large forces for rupturing the palatal suture and/or causing rapid expansion of the palate. Subsequent appliance stages can be designed to apply different amounts of force, such as first applying a large force to break the suture, and then applying smaller forces to keep the suture separated or gradually expand the palate and/or arch.

The determination of the force system can also include modeling of the facial structure of the patient, such as the skeletal structure of the jaw and palate. Scan data of the palate and arch, such as Xray data or 3D optical scanning data, for example, can be used to determine parameters of the skeletal and muscular system of the patient's mouth, so as to determine forces sufficient to provide a desired expansion of the palate and/or arch. In some embodiments, the thickness and/or density of the mid-palatal suture may be measured, or input by a treating professional. In other embodiments, the treating professional can select an appropriate treatment based on physiological characteristics of the patient. For example, the properties of the palate may also be estimated based on factors such as the patient's age—for example, young juvenile patients will typically require lower forces to expand the suture than older patients, as the suture has not yet fully formed.

In step 230, an arch or palate expander design for an orthodontic appliance configured to produce the force system is determined. Determination of the arch or palate expander design, appliance geometry, material composition, and/or properties can be performed using a treatment or force application simulation environment. A simulation environment can include, e.g., computer modeling systems, biomechanical systems or apparatus, and the like. Optionally, digital models of the appliance and/or teeth can be produced, such as finite element models. The finite element models can be created using computer program application software available from a variety of vendors. For creating solid geometry models, computer aided engineering (CAE) or computer aided design (CAD) programs can be used, such as the AutoCAD® software products available from Autodesk, Inc., of San Rafael, Calif. For creating finite element models and analyzing them, program products from a number of vendors can be used, including finite element analysis packages from ANSYS, Inc., of Canonsburg, Pa., and SIMULIA(Abaqus) software products from Dassault Systèmes of Waltham, Mass.

Optionally, one or more arch or palate expander designs can be selected for testing or force modeling. As noted above, a desired tooth movement, as well as a force system required or desired for eliciting the desired tooth movement, can be identified. Using the simulation environment, a candidate arch or palate expander design can be analyzed or modeled for determination of an actual force system resulting from use of the candidate appliance. One or more modifications can optionally be made to a candidate appliance, and force modeling can be further analyzed as described, e.g., in order to iteratively determine an appliance design that produces the desired force system.

In step 240, instructions for fabrication of the orthodontic appliance incorporating the arch or palate expander design are generated. The instructions can be configured to control a fabrication system or device in order to produce the orthodontic appliance with the specified arch or palate expander design. In some embodiments, the instructions are configured for manufacturing the orthodontic appliance using direct fabrication (e.g., stereolithography, selective laser sintering, fused deposition modeling, 3D printing, continuous direct fabrication, multi-material direct fabrication, etc.), in accordance with the various methods presented herein. In alternative embodiments, the instructions can be configured for indirect fabrication of the appliance, e.g., by thermoforming.

Method 200 may comprise additional steps: 1) The upper arch and palate of the patient is scanned intraorally to generate three dimensional data of the palate and upper arch; 2) The three dimensional shape profile of the appliance is determined to provide a gap and teeth engagement structures as described herein.

Although the above steps show a method 200 of designing an orthodontic appliance in accordance with some embodiments, a person of ordinary skill in the art will recognize some variations based on the teaching described herein. Some of the steps may comprise sub-steps. Some of the steps may be repeated as often as desired. One or more steps of the method 200 may be performed with any suitable fabrication system or device, such as the embodiments described herein. Some of the steps may be optional, and the order of the steps can be varied as desired.

Figure 3:
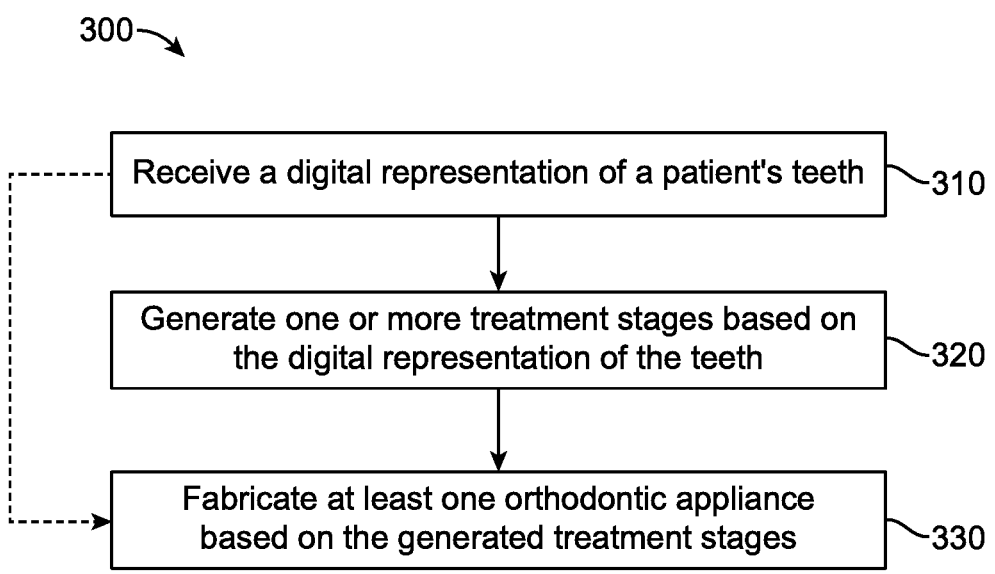
FIG. 3 illustrates a method for digitally planning an orthodontic treatment, in accordance with embodiments.

FIG. 3 illustrates a method 300 for digitally planning an orthodontic treatment and/or design or fabrication of an appliance, in accordance with embodiments. The method 300 can be applied to any of the treatment procedures described herein and can be performed by any suitable data processing system.

In step 310, a digital representation of a patient's teeth is received. The digital representation can include surface topography data for the patient's intraoral cavity (including teeth, gingival tissues, etc.). The surface topography data can be generated by directly scanning the intraoral cavity, a physical model (positive or negative) of the intraoral cavity, or an impression of the intraoral cavity, using a suitable scanning device (e.g., a handheld scanner, desktop scanner, etc.).

In step 320, one or more treatment stages are generated based on the digital representation of the teeth. The treatment stages can be incremental repositioning stages of an orthodontic treatment procedure designed to move one or more of the patient's teeth from an initial tooth arrangement to a target arrangement. For example, the treatment stages can be generated by determining the initial tooth arrangement indicated by the digital representation, determining a target tooth arrangement, and determining movement paths of one or more teeth in the initial arrangement necessary to achieve the target tooth arrangement. The movement path can be optimized based on minimizing the total distance moved, preventing collisions between teeth, avoiding tooth movements that are more difficult to achieve, or any other suitable criteria.

In step 330, at least one orthodontic appliance is fabricated based on the generated treatment stages. For example, a set of appliances can be fabricated, each shaped according a tooth arrangement specified by one of the treatment stages, such that the appliances can be sequentially worn by the patient to incrementally reposition the teeth from the initial arrangement to the target arrangement. The appliance set may include one or more of the orthodontic appliances described herein. The fabrication of the appliance may involve creating a digital model of the appliance to be used as input to a computer-controlled fabrication system. The appliance can be formed using direct fabrication methods, indirect fabrication methods, or combinations thereof, as desired.

In some instances, staging of various arrangements or treatment stages may not be necessary for design and/or fabrication of an appliance. As illustrated by the dashed line in FIG. 3, design and/or fabrication of an orthodontic appliance, and perhaps a particular orthodontic treatment, may include use of a representation of the patient's teeth (e.g., receive a digital representation of the patient's teeth 310), followed by design and/or fabrication of an orthodontic appliance based on a representation of the patient's teeth in the arrangement represented by the received representation.

Figure 4:
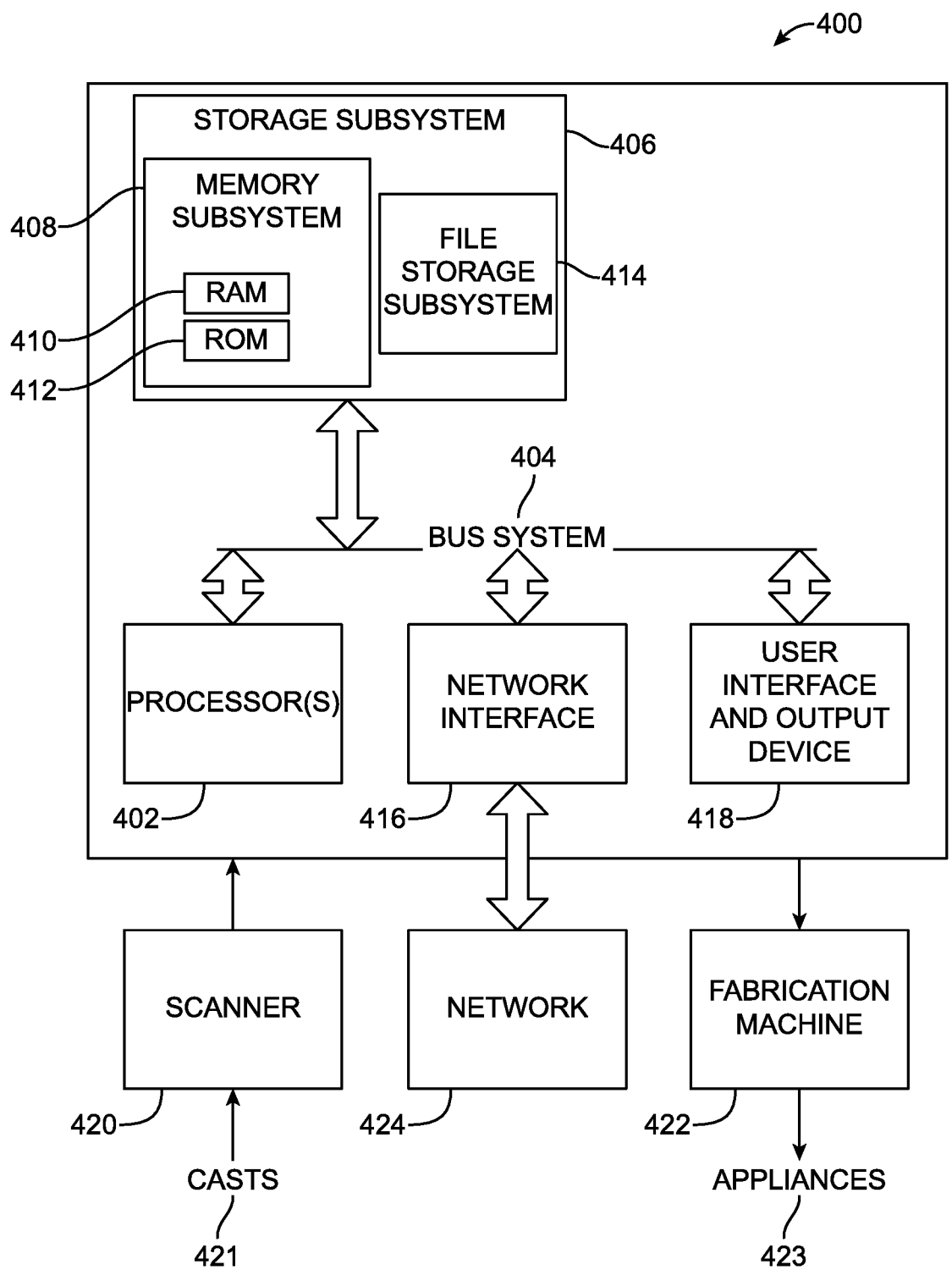
FIG. 4 is a simplified block diagram of a data processing system, in accordance with embodiments.

FIG. 4 is a simplified block diagram of a data processing system 400 that may be used in executing methods and processes described herein. The data processing system 400 typically includes at least one processor 402 that communicates with one or more peripheral devices via bus subsystem 404. These peripheral devices typically include a storage subsystem 406 (memory subsystem 408 and file storage subsystem 414), a set of user interface input and output devices 418, and an interface to outside networks 416. This interface is shown schematically as "Network Interface" block 416, and is coupled to corresponding interface devices in other data processing systems via communication network interface 424. Data processing system 400 can include, for example, one or more computers, such as a personal computer, workstation, mainframe, laptop, and the like.

The user interface input devices 418 are not limited to any particular device, and can typically include, for example, a keyboard, pointing device, mouse, scanner, interactive displays, touchpad, joysticks, etc. Similarly, various user interface output devices can be employed in a system of the invention, and can include, for example, one or more of a printer, display (e.g., visual, non-visual) system/subsystem, controller, projection device, audio output, and the like.

Storage subsystem 406 maintains the basic required programming, including computer readable media having instructions (e.g., operating instructions, etc.), and data constructs. The program modules discussed herein are typically stored in storage subsystem 406. Storage subsystem 406 typically includes memory subsystem 408 and file storage subsystem 414. Memory subsystem 408 typically includes a number of memories (e.g., RAM 410, ROM 412, etc.) including computer readable memory for storage of fixed instructions, instructions and data during program execution, basic input/output system, etc. File storage subsystem 414 provides persistent (non-volatile) storage for program and data files, and can include one or more removable or fixed drives or media, hard disk, floppy disk, CD-ROM, DVD, optical drives, and the like. One or more of the storage systems, drives, etc may be located at a remote location, such coupled via a server on a network or via the internet/World Wide Web. In this context, the term "bus subsystem" is used generically so as to include any mechanism for letting the various components and subsystems communicate with each other as intended and can include a variety of suitable components/systems that would be known or recognized as suitable for use therein. It will be recognized that various components of the system can be, but need not necessarily be at the same physical location, but could be connected via various local-area or wide-area network media, transmission systems, etc.

Scanner 420 includes any means for obtaining a digital representation (e.g., images, surface topography data, etc.) of a patient's teeth (e.g., by scanning physical models of the teeth such as casts 421, by scanning impressions taken of the teeth, or by directly scanning the intraoral cavity), which can be obtained either from the patient or from treating professional, such as an orthodontist, and includes means of providing the digital representation to data processing system 400 for further processing. Scanner 420 may be located at a location remote with respect to other components of the system and can communicate image data and/or information to data processing system 400, for example, via a network interface 424. Fabrication system 422 fabricates appliances 423 based on a treatment plan, including data set information received from data processing system 400. Fabrication machine 422 can, for example, be located at a remote location and receive data set information from data processing system 400 via network interface 424.

The data processing aspects of the methods described herein can be implemented in digital electronic circuitry, or in computer hardware, firmware, software, or suitable combinations thereof. Data processing apparatus can be implemented in a computer program product tangibly embodied in a machine-readable storage device for execution by a programmable processor. Data processing steps can be performed by a programmable processor executing program instructions to perform functions by operating on input data and generating output. The data processing aspects can be implemented in one or more computer programs that are executable on a programmable system, the system including one or more programmable processors operably coupled to a data storage system. Generally, a processor will receive instructions and data from a read-only memory and/or a random access memory. Storage devices suitable for tangibly embodying computer program instructions and data include all forms of nonvolatile memory, such as: semiconductor memory devices, such as EPROM, EEPROM, and flash memory devices; magnetic disks such as internal hard disks and removable disks; magneto-optical disks; and CD-ROM disks.

Palate Expanders

Figure 5:
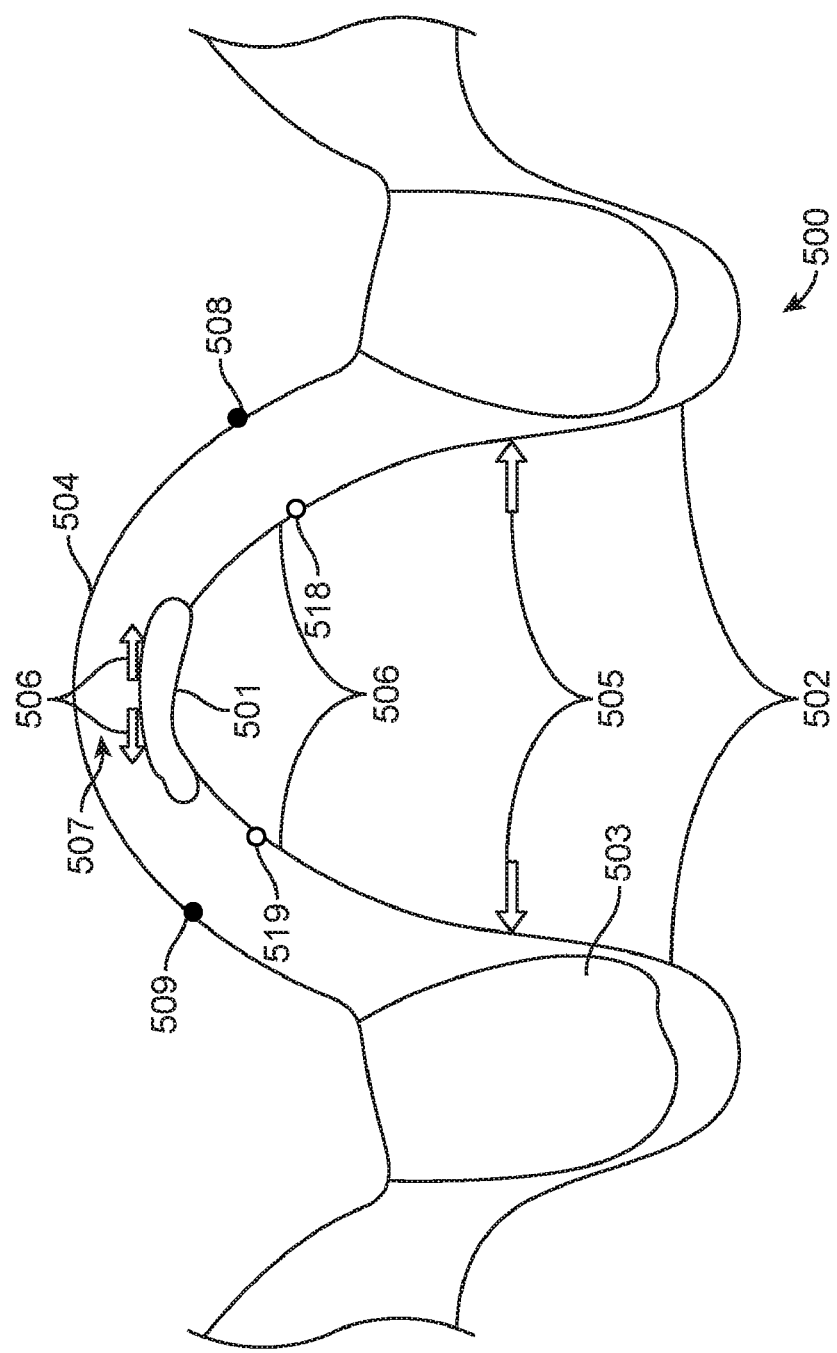
FIG. 5 illustrates an orthodontic appliance comprising a palatal expander portion within the mouth of a patient, in accordance with embodiments.

FIG. 5 illustrates an orthodontic appliance 500 comprising a palatal expander portion 501 within the mouth of a patient. The appliance 500 comprises a teeth engaging portion having a plurality of tooth-receiving cavities 502 configured to receive teeth. A gap 507 can extend between the upper portion of the palate and the upper portion of appliance 500 when placed in the mouth of the patient. The teeth engaging portion can be similar to commercially available tooth repositioning appliances comprising transparent shell portions to reposition teeth. The teeth engaging portion can be configured to resiliently reposition the patient's teeth 503. In particular, a palatal expander may apply force generating orthodontic forces 505 against groups of one or more teeth on opposite sides of a patient's mouth, in order to cause the patient's palate 504 to expand. These forces may be caused by an expansion 506 of the expander portion 501. An extension portion 506 can extend between the expander portion 501 and the teeth engaging portion comprising cavities 502 in order to couple the expander portion 501 with the teeth engaging portion. Among other outcomes, this expansion of palate 504 may coincide with an increase in distance between teeth 503 on opposite sides of the patient's mouth. Palate expansion typically requires stronger forces and larger-scale movements than those typically used for orthodontic movement of single teeth, presenting unique challenges in designing palate expanders. Among the challenges that must be overcome are the design of a palate expander capable of providing strong forces without damage as well as preventing or minimizing distortions, such as may cause uncomfortable upward pressure between the expander portion 501 and the palate 504.

In particular, the force 505 applied to the teeth 503 may tend to cause an undesired tipping movement, in which the teeth 503 are tilted outwards as a reaction to the applied force from the aligner. To reduce tipping, the extension portion 506 may be shaped to contact portions of the patient's palate, such at locations 508 and 509, so as to apply force to the palate directly in addition to the forces applied to the teeth 503. Optionally, an implantable device such as a temporary anchorage device (TAD) may be provided in the patient's palate, such as at locations 508 and 509. The TAD can be embedded into or attached to the bone of the patient's palate so as to transmit force directly from the appliance to the patient's palate. The appliance can be shaped with surface portions 518 and 519 configured to receive the TAD, such as a hook or socket for example. The locations of points 508 and 509 can be varied as needed to distribute appropriate force; for example, the locations can be selected by a treating professional or a computer model of the patient's palate and dentition. In some embodiments, the TADs are located on the roof of the palate on opposite sides of the suture, and the appliance is shaped to engage the TADs to apply a palate-expanding force. Multiple points of contact, including continuous contact surfaces, may also be used for direct palate contact and/or contact with a TAD. This allows the total palate-separating force to be distributed over multiple surfaces, decreasing the amount of force any particular surface must bear. For example, the force on the teeth 503 can comprise only a portion of the total palate expanding force, reducing the likelihood of inducing tipping movement.

An orthodontic appliance 500 comprising a palatal expander shaped to apply force both to the palate and to the teeth can be readily designed for fabrication using the methods disclosed herein. For example, in method 200, step 220, the force system can include forces applied to both teeth and palate areas to induce a palatal expansion. In step 230, a fabrication design for extension portion 506 can include material shaped to contact portions of the palate along the left and/or right arching parts of the palate, such as around areas 508 and 509 of the palate, for example. Contact to the top of the palate may be limited in the palate-expansion forces it can apply, while potentially causing discomfort to the patient. Accordingly, contact between the top of the palate and the appliance when worn is not required. Thus, while in some cases, the appliance can be shaped to contact to the top of the palate, the appliance can also be shaped to provide a gap 507. This gap need not inhibit contact between the lateral portions of the palate and the appliance, such that palatal expansion forces can be applied to the sides of the palate without requiring contact with the top of the palate. The appliance can be shaped such that contact areas 508 and 509 are spread out over a large area of the palate, applying more uniform pressure across the contact areas while applying less localized pressure to the palate when the appliance is worn.

Direct fabrication allows the use of a wide range of materials and structures, which may be combined in a variety of ways when designing appliance structures such as palate expanders In some cases, traditional structures used in palate expanders such as manually-adjusted screws may be directly fabricated as well as augmented with further structures as described herein. In some cases, traditional structures such as screws or springs may be used in the appliances disclosed herein without being directly fabricated. Alternatively, palate expanders may be fabricated without the need for manual adjustments, for example by incorporating, within the expander portion 501, rigid materials that expand when contacted with saliva, such as hydrophilic polymers, for example. Other materials with similar expansion properties, such as high rigidity and swelling capacity, may be selected to customize the expansion, as will be appreciated by a person of ordinary skill in the art. In some cases, expander portion 501 can comprise a thermoplastic or thermoset material, for example.

Figure 6:
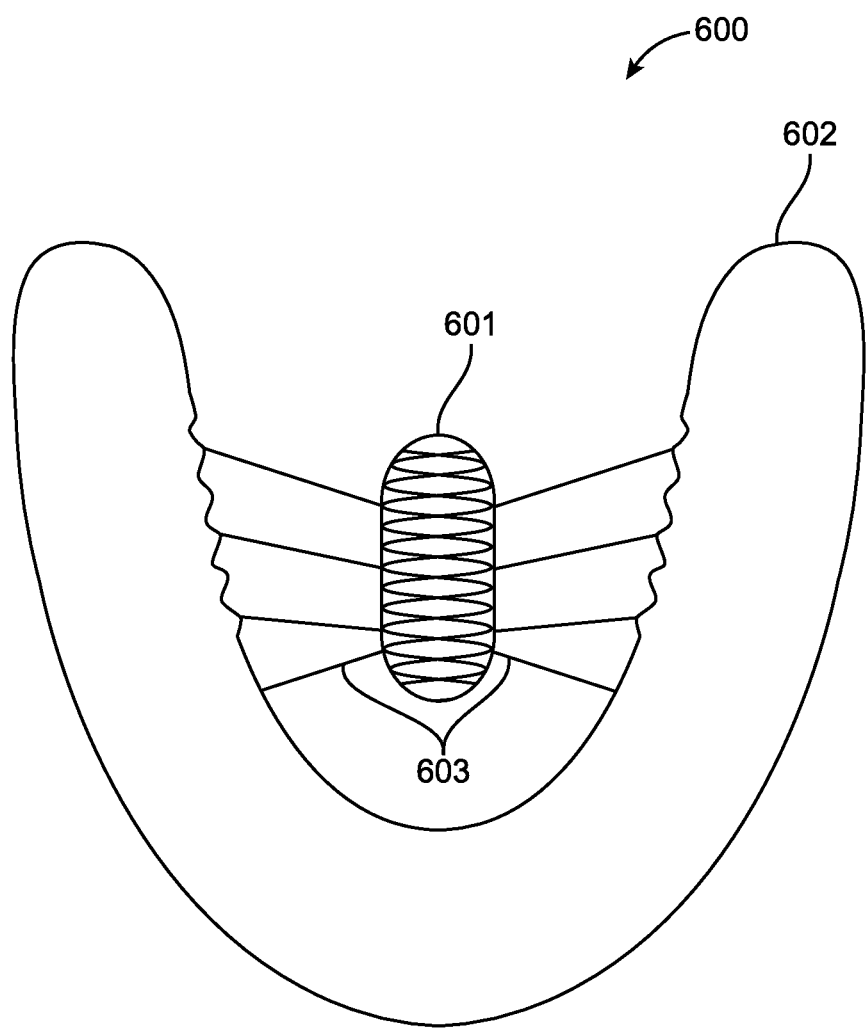
FIG. 6 illustrates a top view of an appliance comprising a palate expander portion, a shell, and an extension structure joining the two together, in accordance with embodiments.

FIG. 6 illustrates a top view of an appliance 600. Appliance 600 may comprise many of the features and structures of appliance 500, for example. Appliance 600 comprises a palate expander portion 601, a shell 602, and an extension structure 603 joining the two together. Expansion of palate expander 601 provides force generating forces on shell 602, transmitted by extension structure 603. When worn by a patient, this may cause an expansion of a patient's palate, as illustrated in corresponding appliance 500 in FIG. 5. In some embodiments, appliance 600 may be fabricated as a single structure, wherein palate expander 601, shell 602, and extension structure 603 may comprise different materials. In some embodiments, palate expander 601 may connect directly to shell 602, omitting extension structure 603. In some embodiments, palate expander 601 may comprise a plurality of materials, and additionally or alternatively, shell 602 and extension structure 603 may each also comprise one or more materials. The size, structure, and materials of palate expander 601, shell 602, and extension structure 603 may be varied to customize the force generating force produced. In further embodiments, palate expander 601, shell 602, and extension structure 603 may comprise the same material; for example, in some cases in which palate expander 601 comprises a fabricated spring or screw structure.

In some embodiments, palate expander 601 may comprise a material that expands upon contact with a patient's saliva, permitting it to spontaneously begin applying force after being placed in a patient's mouth. The amount of force applied will depend on variables that may be controlled during fabrication, such as the size of the palate expander 601 and choice of material from which it is fabricated. Generally, larger palate expanders may cause larger forces, and more force generating materials may likewise generating larger forces. The size of the palate expander may be varied during fabrication, for example by making it larger in a horizontal axis while making extension structure 603 correspondingly shorter in that axis. The expansiveness of the material comprising palate expander 601 may be varied in a variety of ways, such as by switching to a material of different expansiveness or by employing a plurality of materials that expand differently. For example, a palate expander made of composite material uniformly comprising equal amounts of force generating and non-force generating polymer will provide less force than a similar palate expander made entirely of the force generating polymer Similar effects can be generated using other non-polymer materials. In general, the force may be tuned as desired by varying the proportions of different polymers or other materials in this manner. In the case of polymers, material expansion can also be controlled by choosing polymers with different amounts of cross-linking, with more cross-linking leading to smaller amounts of expansion.

Another consideration when designing a palate expansion appliance is the avoidance of upward pressure on the patient's palate. If a palate expander expands too much in a vertical direction, it may put pressure on the patient's palate, which may prove uncomfortable. Horizontal expansion may also indirectly cause uncomfortable pressure in some cases, such as when it causes upward flexing of the appliance. The material properties of a fabricated palate expander may be designed so as to relieve this potential problem.

Figure 7:
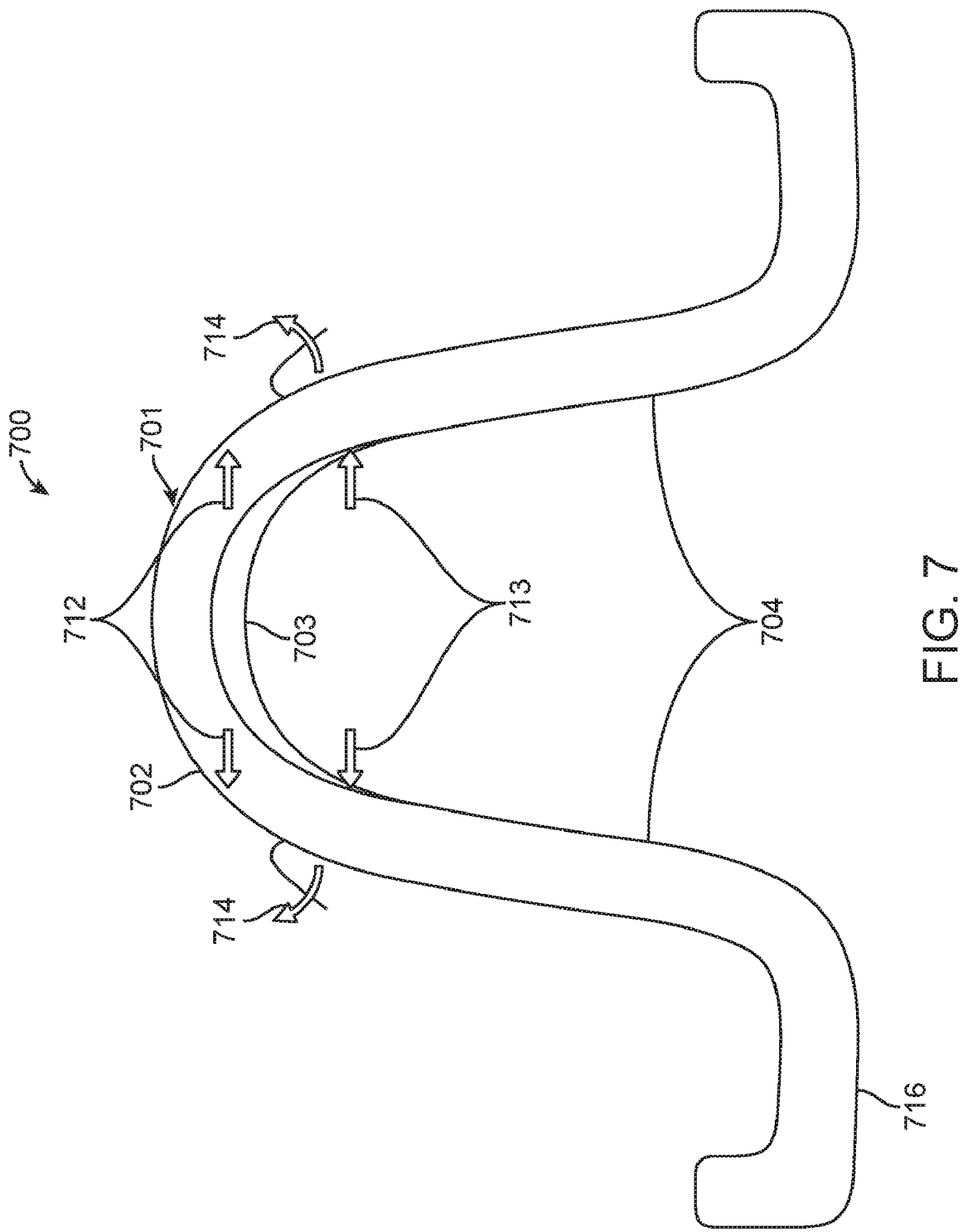
FIG. 7 illustrates an appliance which has been fabricated so as to avoid upwards pressure on a patient's palate, in accordance with embodiments.

FIG. 7 illustrates an appliance 700 which has been fabricated so as to inhibit contact with and avoid upwards pressure on a patient's palate, with a gap extending between the upper portion of the palate and the upper portion of the appliance as described herein. The palate expander appliance 700 comprises a palate expander 701 comprising a plurality of materials, arranged into a plurality of layers. As illustrated, the plurality of layers comprises an upper layer 702 that is configured to inhibit contact with the patient's palate and a lower layer 703 underneath. These two layers are both attached to appliance shell 704, wherein the connection may be direct or may comprise an extension structure as described herein. The materials of layers 702 and 703 are chosen to expand at different rates—for example, upper layer 702 may comprise a material with lower swelling capacity than the material of layer 703. This difference between materials may, for example, be controlled by fabricating the different layers from polymeric material with different amounts of cross-linking, thereby varying the swelling capacity. For example, materials with more cross-linking can have enhanced stiffness, and thereby resist swelling, whereas materials with less cross-linking can have reduced stiffness, thereby increasing swelling. The effect of this difference is illustrated by forces 712 and 713, wherein forces 713 are greater in magnitude than forces 712. These different magnitudes of force cause a bending of the appliance 714 that can relieve upwards pressure that might otherwise push on the top of the palate of the patient. The bending 714 can also be used to apply contact forces on the lateral sides of the palate, such that force on the roof of the mouth is diminished while force on the sides of the palate and on the teeth is increased, thereby providing a combined palate expansion force. The magnitude of palate contact force can be adjusted by selecting an appropriate shape and thickness of upper layer 702 near the contact points, as well as appropriately selecting lower layer 703 to provide the desired expansion movement. Further layered structures may be contemplated, comprising a plurality of layers of different swelling capacities. Alternatively or additionally, the layered structure may vary its swelling capacity continuously along axes, such as a vertical axis and/or a horizontal axis.

Further embodiments are shown in FIGS. 8A-E, which illustrate a few of the many optional palate expander structures which may be fabricated using direct fabrication techniques as described herein. The structures depicted in FIGS. 8A-E may be fabricated as part of an appliance further comprising tooth-receiving structures such as concavities. These embodiments show directly fabricated resilient structures configured to urge teeth on opposite sides of the arch away from each other. The tooth receiving engagement structures comprising concavities can be shaped to receive teeth on the lingual side closer to the gingival portion than the occlusal portion. The appliances may comprise interproximal engagement structures to extend at least partially into interproximal spaces of the patient's teeth to improve retention. In many embodiments, these appliances can be retained on the patient's teeth with a low profile configuration without extending to both sides of each of the teeth. These appliances can be configured to provide a gap as described herein.

Figure 8A:
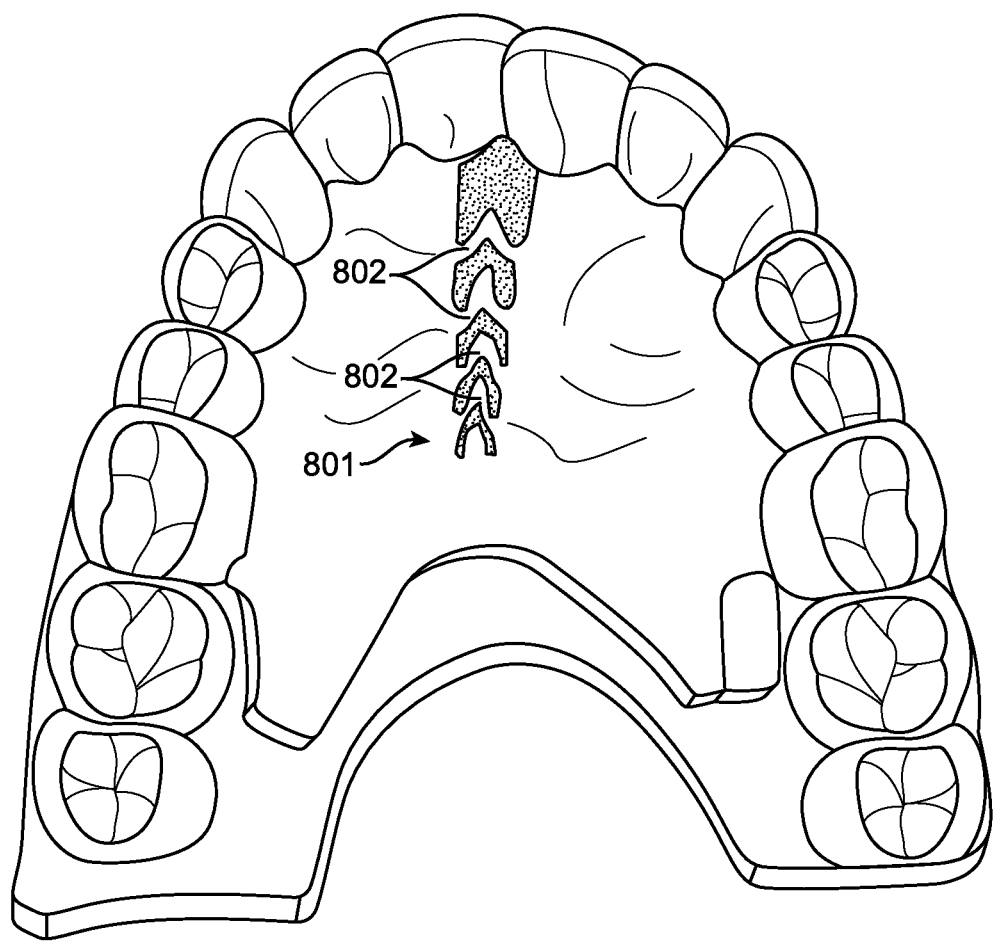
FIG. 8A illustrates an appliance with palatal expander comprising a fabricated spring structure, in accordance with embodiments.

FIG. 8A illustrates an appliance with palatal expander comprising a directly fabricated spring structure 801. The palatal expander is shown placed on the patient's teeth. The spring structure 801 comprises a plurality of compressible structures 802. When the appliance is inserted into a patient's mouth, the compressible structures 802 are compressed, storing elastic potential energy. This stored potential energy results in an outward force to induce a palate expansion.

Figure 8B:
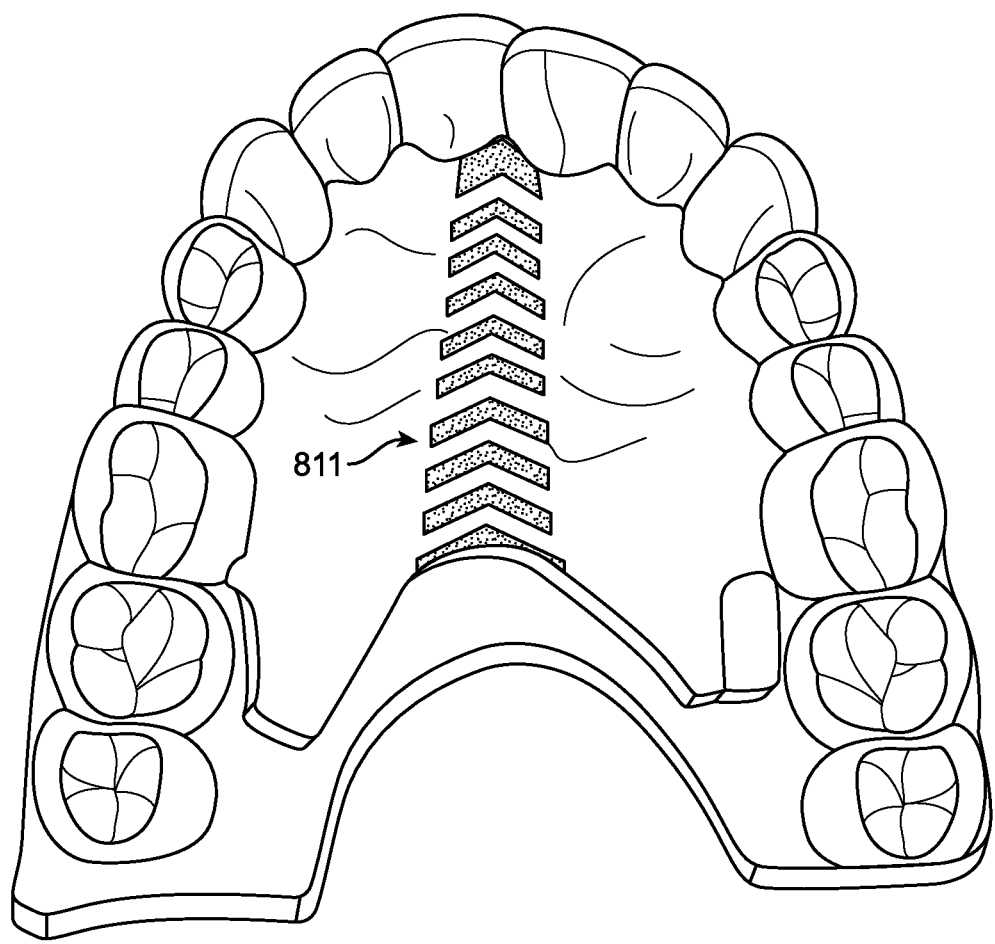
FIG. 8B illustrates an appliance with palatal expander comprising a fabricated echelon-patterned spring structure, in accordance with embodiments.

FIG. 8B illustrates an appliance with palatal expander comprising a directly fabricated echelon-patterned and/or chevron patterned spring structure 811. The palatal expander is shown placed on the patient's teeth. The echelon structures comprising echelon-patterned spring structure 811 may be directly fabricated out of compressible material that will bend when placed in the patient's mouth. This bending stores elastic potential energy that results in an outward force to induce a palate expansion.

Figure 8C:
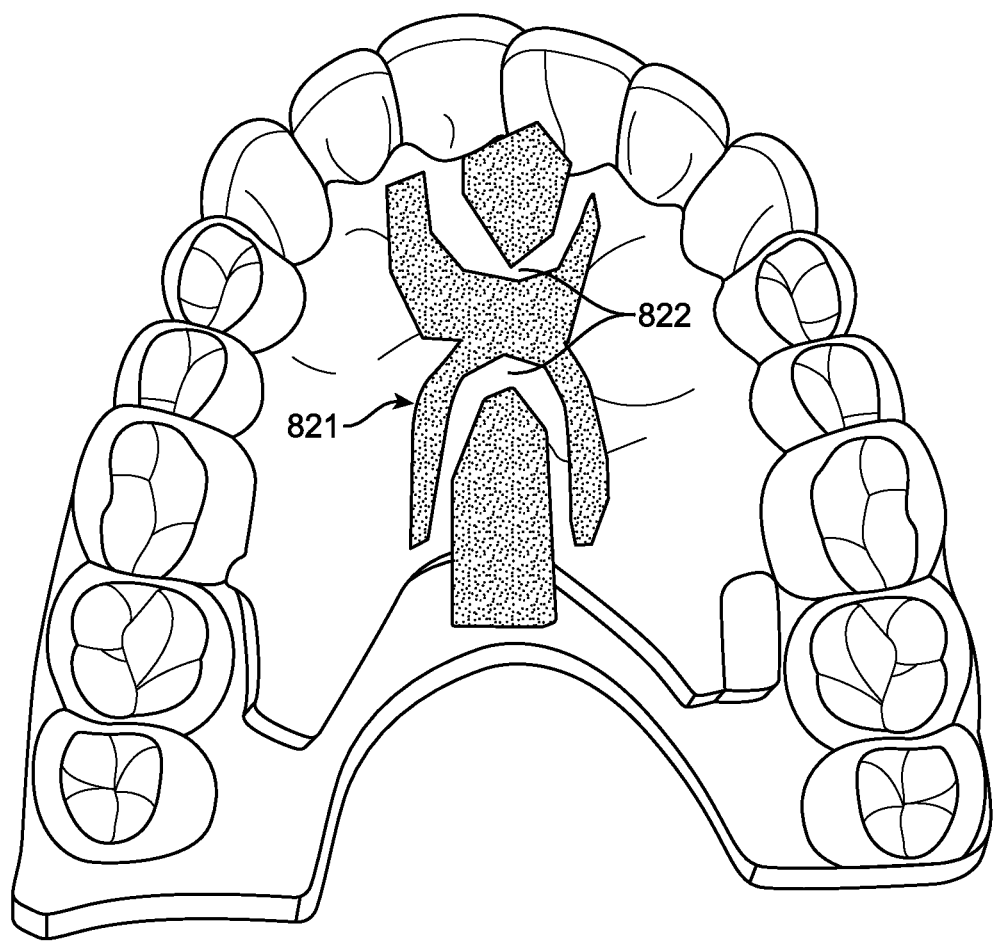
FIG. 8C illustrates an appliance with palatal expander comprising a fabricated structure comprising compressible curved portions, in accordance with embodiments.

FIG. 8C illustrates an appliance with palatal expander comprising a fabricated structure 821 comprising compressible curved portions 822. The palatal expander is shown placed on the patient's teeth. The curved structures 822 may be fabricated out of compressible material that will bend when placed in the patient's mouth. This bending stores elastic potential energy that results in an outward force to induce a palate expansion.

Figure 8D:
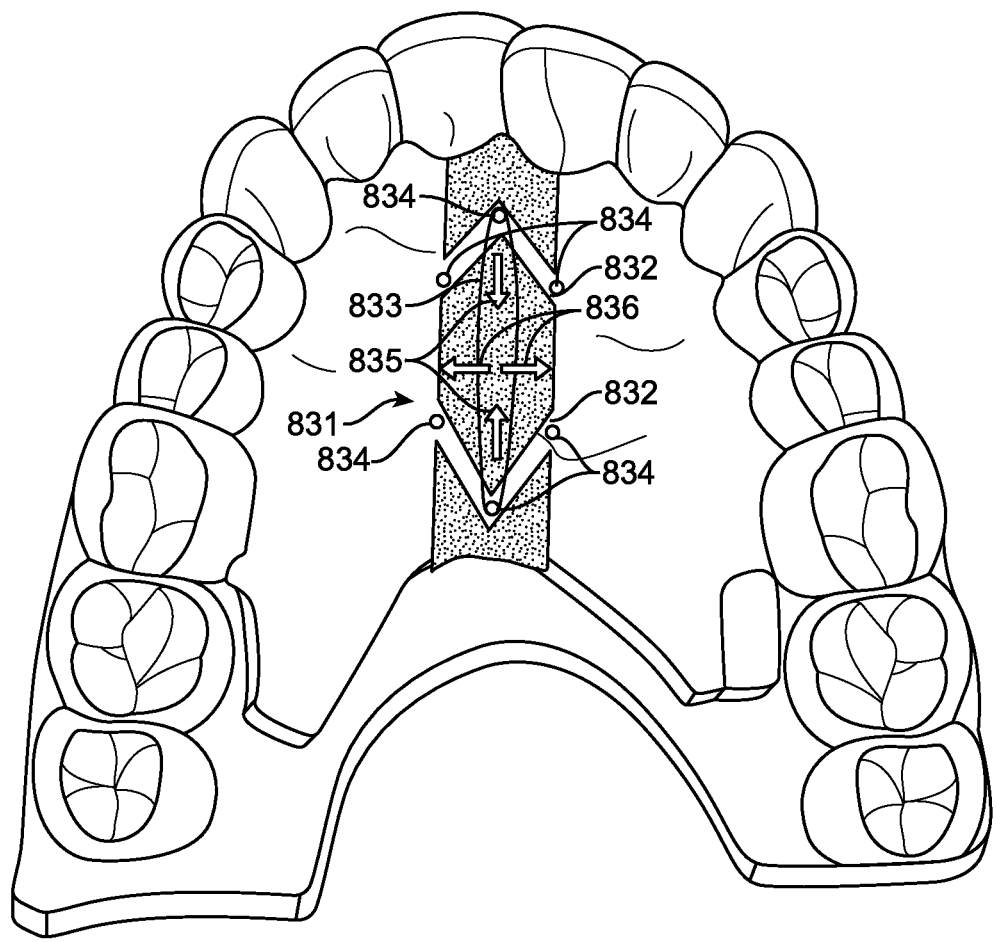
FIG. 8D illustrates an appliance with palatal expander comprising a fabricated jack structure comprising compressible hinged arms, in accordance with embodiments.

FIG. 8D illustrates an appliance with palatal expander comprising a fabricated jack structure 831 comprising compressible hinged arms 832. The palatal expander is shown placed on the patient's teeth. Opposite ends of hinged arms 832 are connected by an elastic band 833, applying an inward force 835 to opposite ends of the arms together. This inward force produces a motion as hinged arms rotate about hinges 834, which may be fabricated as part of structure 831. An outward force 836 results as the structure expands in the image's horizontal axis while compressing in the image's vertical axis. Force can be applied at the hinges, for example using a rubber band, to compress the jack structure and apply a palate-expanding force.

The force generating components disclosed herein can generate forces based on a target palatal displacement. For example, an amount of palatal expansion can be selected, and the force generating component can be fabricated such that an expansion force is generated when the appliance is worn, so long as the amount of palatal expansion is less than the target palatal displacement. Thus, an appliance can generate palatal expansion forces without causing excessive expansion. In some cases, the target palatal displacement can be adjustable; for example, adjustable screws, springs, bands, or other components can be adjusted to change the size of the palatal expander, thereby changing the target palatal displacement. An adjustable palatal expander can be used to generate a slow palatal expansion, for example.

Figure 8E:
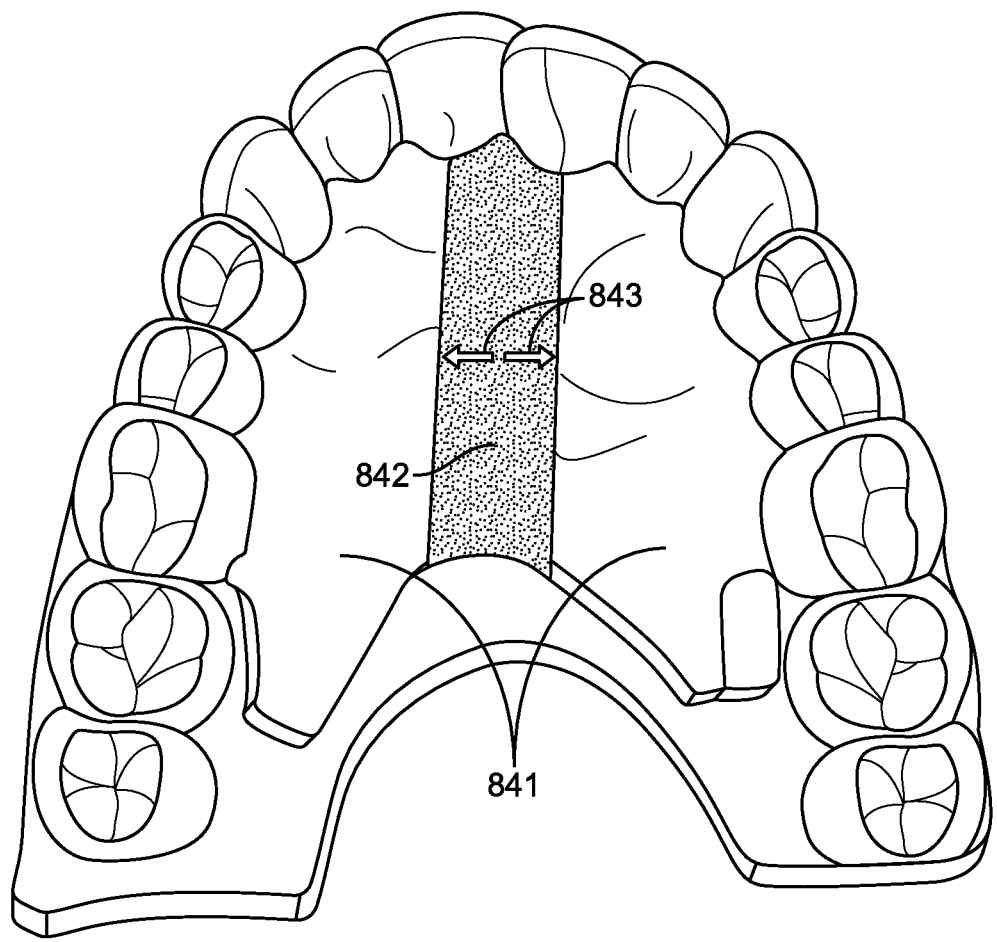
FIG. 8E illustrates an appliance with palatal expander comprising a material that expands upon contact with human saliva, in accordance with embodiments.

FIG. 8E illustrates an appliance with palatal expander comprising a material that expands upon contact with human saliva. The palatal expander is shown placed on the patient's teeth. Outer portions 841 of the appliance are comprises a rigid material that does not expand, while an inner portion such as central portion 842 comprises a rigid material with a high swelling capacity such that it expands within a patient's mouth as it absorbs water from a patient's saliva. The expansion causes outwards forces 843 that may be used to induce a palate expansion. As discussed above, in some embodiments, central portion 842 comprises a plurality of layers or a material with continuously varied swelling capacity. Alternatively or in combination, the inner portion such as central portion 842 comprises an elastic material capable of being compressed upon insertion to generate the force to the teeth to expand the palate.

Although specific resilient spring structures are shown, the material can be shaped with structures such as voids to provide flexibility and compressibility to the material, similar to closed cell foam and open cell foam to provide a compressible force generating structure. Alternatively or in combination a plurality of resilient structures as described can be formed on a small scale, for example no more than about 2 mm across, in order to provide the force generating portion. Furthermore, the forces produced by the appliances disclosed herein can be varied by changing the size, shape, mass, and elasticity of the materials used in the expanders, individually or in combination.

In some embodiments, aligners and palatal expanders may be directly fabricated as separate components to be fit together later for use. The palate expander comprises a force generating component as disclosed herein and the aligner comprises a teeth engagement structure as disclosed herein. The separate components may comprises corresponding engagement structures that allow the components to fit together and hold the aligner and palate expander together when placed in the mouth of the patient. The corresponding engagement structures can be configured in many ways and may comprise one or more of locking structures, a protrusion sized to extend into a receiving structure such as a recess, nested structures or locking structures. The aligner and plate expander may comprise corresponding shape profiles that allow the corresponding structures of the palate expander to aligner to fit together and be held in place. In some instances, the corresponding structures can be configured for the engagement structures to gently snap in place, for example. The user can be provided with a plurality of pieces to snap in place over the course of a treatment plan of palate expansion, for example.

Similarly, each of the palate expander and aligner can optionally be composed of multiple, separately fabricated parts. For example, an aligner can comprise a left and right portion to fit the left and right dental arches, or left, right, and center portions to fit respective left, right, and central teeth of an arch. These portions can be fabricated as a single unit that can be separated and reattached, or they can be fabricated separately for attachment thereafter. Similarly, the palate expander can be fabricated in one, two, three, or more separate parts that can be joined together, such as with the joining methods disclosed herein. In some cases, for example, each part, or certain parts, can be fabricated from different materials so as to possess different properties such as stiffness.

Figure 9A:
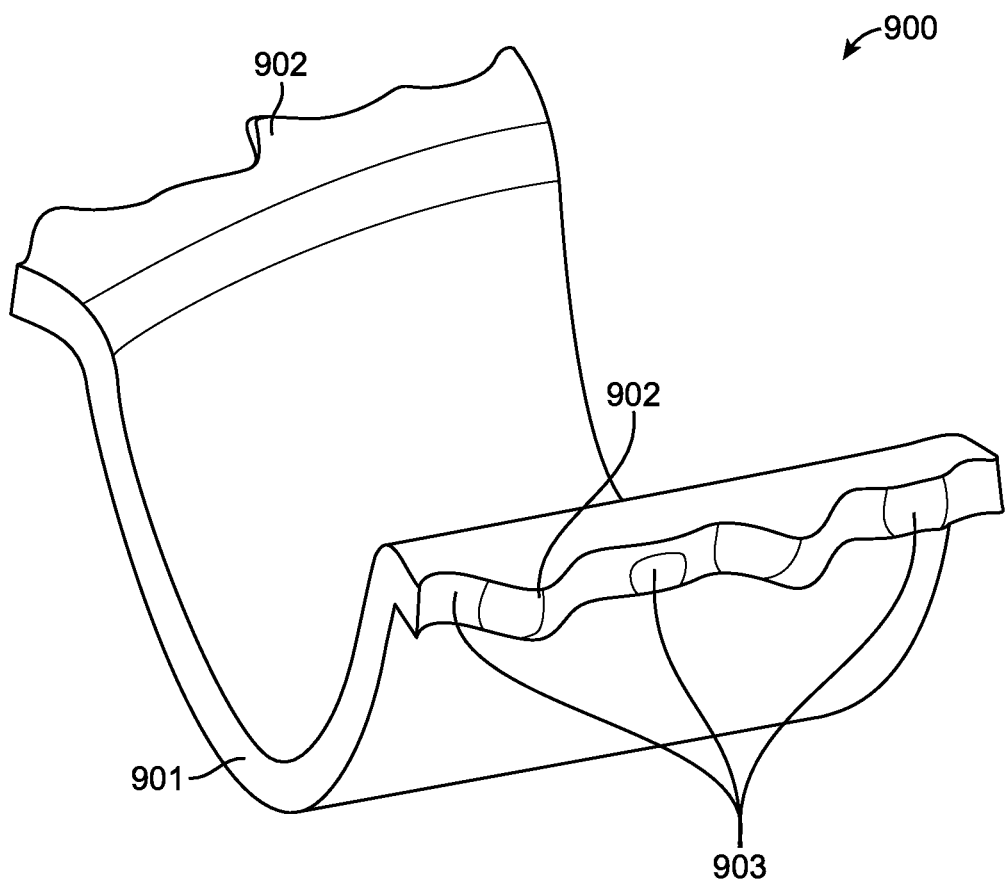
FIG. 9A illustrates a removable palatal expander fabricated to mate with an orthodontic appliance, in accordance with embodiments.

FIG. 9A illustrates a removable palatal expander 900 fabricated to mate with an orthodontic appliance. The palatal expander 900 comprises an arch component 901 fabricated from elastic material to fit the palate of a patient. The material may be fabricated to be larger than the patient's palatal region, so that it compresses when worn, permitting an outward force to be applied to a patient's teeth. The palatal expander 900 further comprises a ridged portion 902 on each side designed to conform to the surface of an orthodontic appliance. The rigid portion 902 may comprises protrusions sized and shaped to extend toward interproximal the space of the teeth when engaging corresponding structures of the teeth engaging appliance. In order to secure the palatal expander to an orthodontic appliance, indentations 903 may be located in the ridged portion 902 configured to mate with protrusions on the appliance.

Figure 9B:
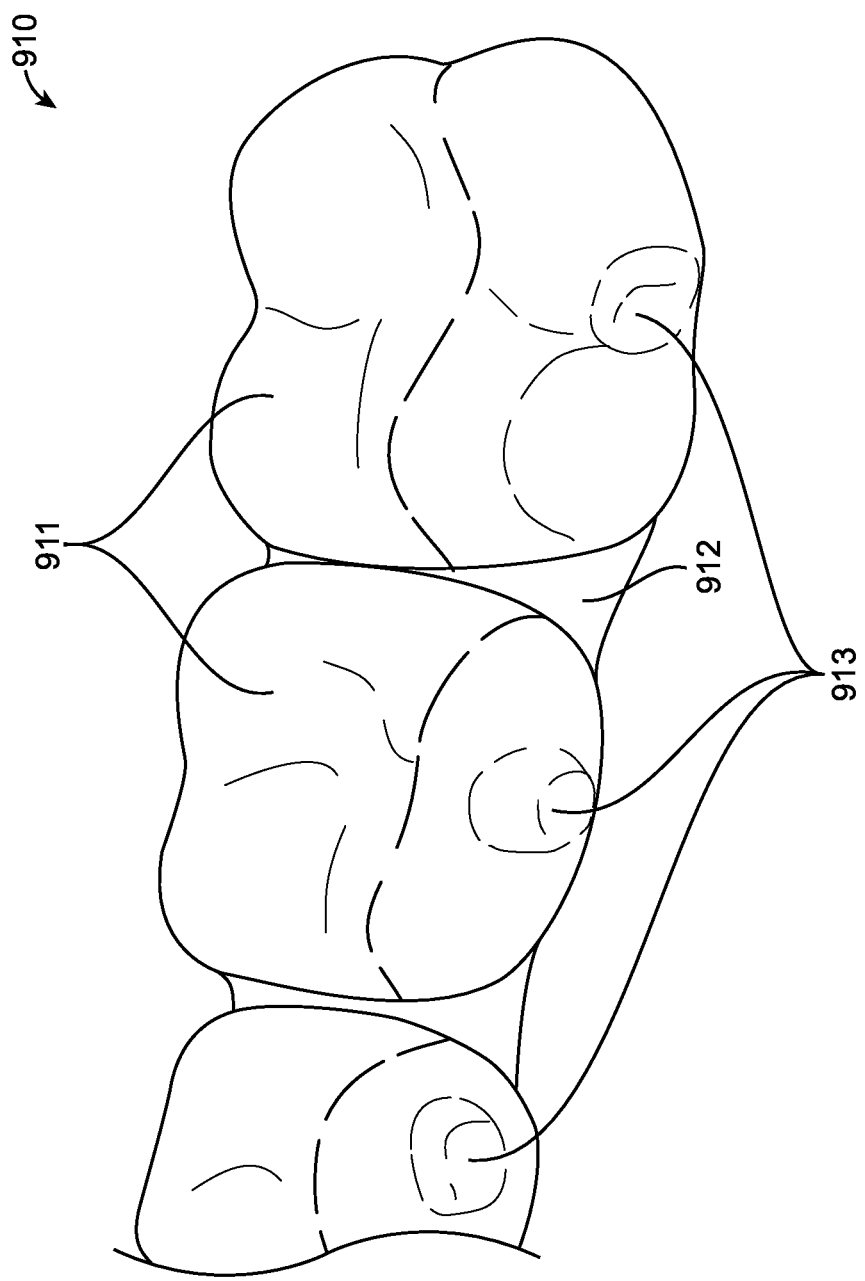
FIG. 9B illustrates part of an aligner designed to mate with a palatal expander, in accordance with embodiments.

FIG. 9B illustrates part of an aligner 910 designed to mate with a palatal expander as shown in FIG. 9A. The aligner 910 comprises a plurality of teeth engagement structures comprising a plurality of teeth receiving cavities 911 sized and shaped to engage the teeth for palate expansion. The aligner comprises plurality of tooth-receiving cavities 911, as well as a labial contour 912. The labial contour 912 matches the corresponding ridged portion 902 of the palatal expander. The teeth engaging aligner component further comprises protrusions 913 configured to engage, for example mate, with the corresponding indentations 903 of the palatal expander 900. The protrusions 913 can be located on a labial side of the teeth. The teeth engaging aligner component may comprise receiving structures shaped to receive the protrusions of the rigid portion 902 of the arch component 901. This arrangement allows the palatal expander 900 and the aligner 910 to hold together, for example to securely mate together. The aligner 910 can be configured to move teeth in accordance with a treatment plan as described herein. The arch component 901 can be configured to move the palate in accordance with a palate expansion plan.

Figure 9C:
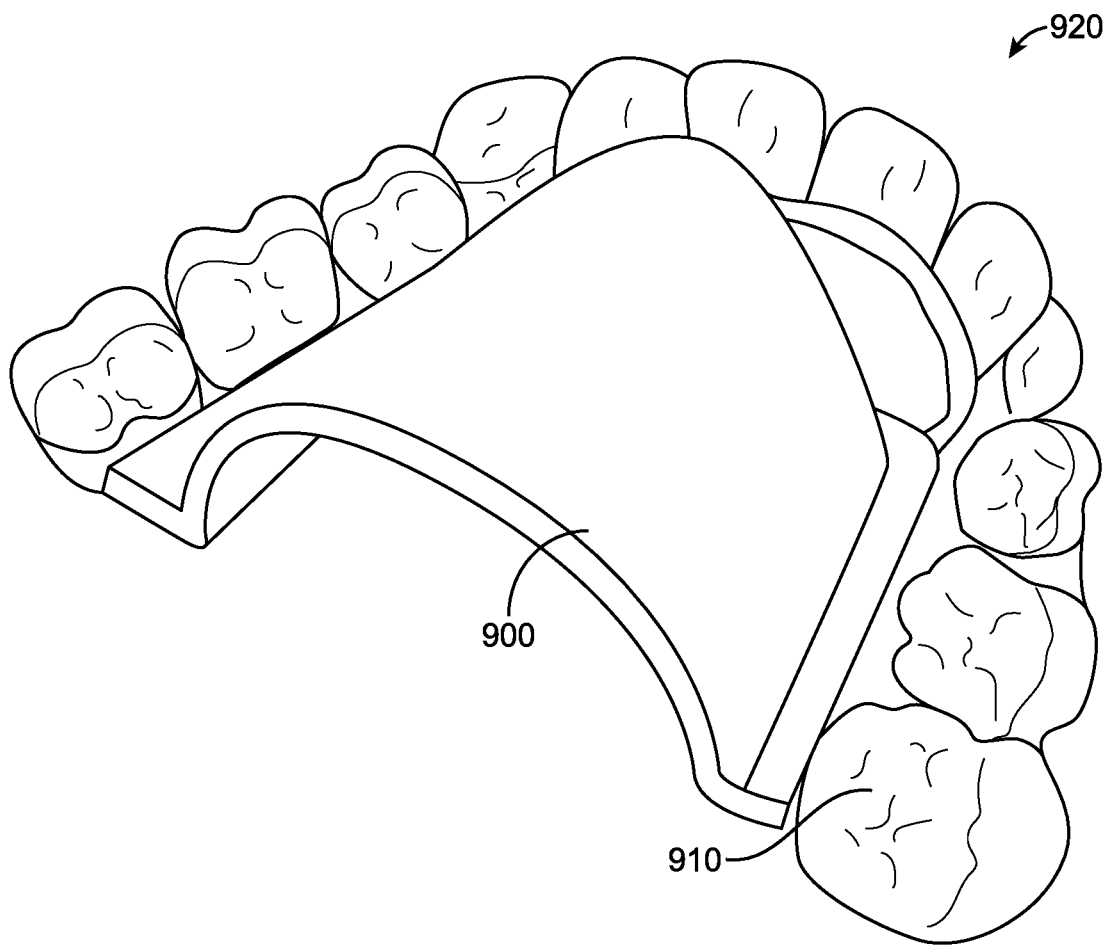
FIG. 9C illustrates a prototype orthodontic appliance comprising both a palatal expander and an aligner in accordance with embodiments, in accordance with embodiments.

The teeth engagement structures that couple to the teeth can be configured in many ways. Although an aligner is shown, other structures as described herein can be used to engage the teeth and couple to the palate expander in order to engage the teeth. In some cases, the occlusal surface above the teeth receiving cavities can be shaped to simulate the occlusal surfaces of teeth, as shown in FIG. 9C, showing a surface with varying height similar to that of ordinary tooth surfaces. Alternatively, portions of the occlusal surfaces of some or all teeth receiving cavities can be provided with a flatter surface 716 (see FIG. 7). By supplying upper and lower appliances with such flattened surfaces, the respective upper and lower arches can avoid engaging, allowing the arches to move more freely. For example, if the occlusal surfaces of appliances along the left and right molars of each arch are substantially flattened, the left and right arches can move more freely in lateral directions. Thus, for example, the expansion of the palate will be less inhibited by the engagement of the upper and lower arches, allowing less force to be needed.

FIG. 9C show a picture of a directly fabricated orthodontic appliance 920 comprising both a palatal expander 900 and an aligner 910. The palatal expander and aligner are made of different materials, with the palatal expander capable of flexing when worn to store elastic energy, thereby applying force to a patient's teeth. The palate expander component comprises an unloaded free standing configuration with the engagement structures such as protrusion having a separation distance on opposing sides of the expander sized larger than corresponding structures of opposing sides of the arch of the aligner.

Figure 9D:
FIG. 9D illustrates a 3D model of an appliance comprising a palatal expander and an aligner in accordance with embodiments.

A 3D computer model 930 of appliance 920, which may for example be generated when designing an orthodontic appliance according to methods 200 or 300, is illustrated in FIG. 9D. A person of ordinary skill in the art can use computer modeling and experimentation to determine the forces to the teeth appropriate for palate expansion, and determine the size, shape and material as described herein. The palate expander component can be sized to inhibit or avoid contact with part or all of the palate in response to an oral scan or dental impression to generate three dimensional profile data of the mouth as described herein. The palate expander component can be also be sized to selectively contact portions of the palate to apply palate-expanding forces, which may be distributed over parts of the left and right palatal arches of a patient so as to decrease load on the teeth of the patient. The amount of force applied by appliance 920 is affected by the ridges illustrated in the center of the arch. The ridges on the appliance increase the stiffness of the expander, which can be used to vary the expansion force applied. For example, adding thick ridges can produce a stiff arch that applies forces over a short range, whereas thinner or missing ridges can produce a more resilient shape that applies forces over a longer range.

Figure 10:
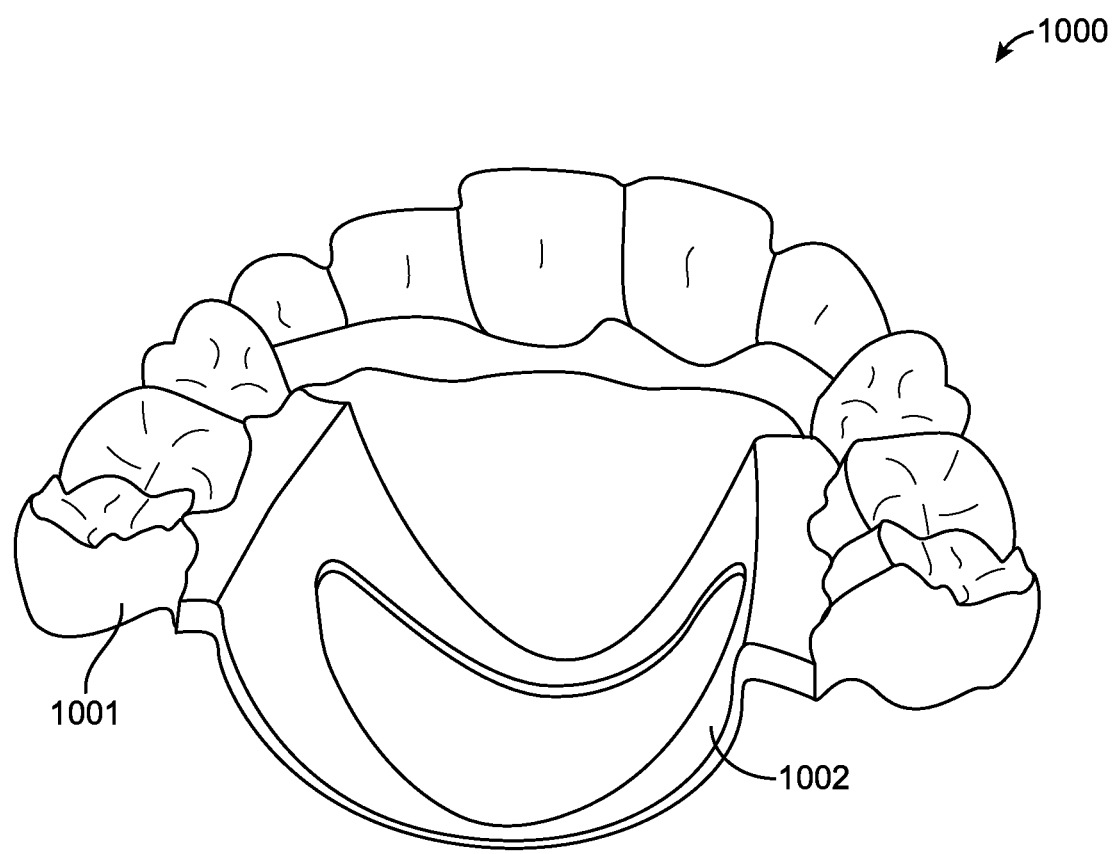
FIG. 10 shows an orthodontic appliance comprising a plastic aligner portion and a metallic palatal expander in accordance with embodiments.

FIG. 10 shows a design of an orthodontic appliance 1000 comprising a plastic aligner component 1001 and a metallic palatal expander 1002. The use of metal materials offer a number of advantages, such as greater applicable force, lack of stress relaxation, durability, corrosion resistance, and easy sterilization. Biocompatibility is also readily achieved, since the use of metallic material in orthodontics is already used in the dental industry, and the selection of appropriate metals will be apparent to one of ordinary skill in the art. Metallic aligners may be usefully fabricated using direct fabrication techniques such as Direct Metal Laser Sintering (DMLS), Electon-Beam Sintering, or Selective Laser Sintering, and in some cases may be fabricated directly along with a directly fabricated plastic aligner component. Similarly, multiple direct fabrication techniques may be used in combination, such as by fabricating separate parts using separate techniques, such that the parts can be assembled into an appliance. The force applied by orthodontic appliance 1000 can be readily controlled by the thickness and topology of the metallic expander 1002. For example, the metallic expander 1002 comprises an arch with a circular hole, such that the amount of metal is less than would be present in a solid metallic arch. The expanding force is correspondingly reduced. By varying the size or shape of the hole of expander 1002, the expanding force can be increased or decreased as needed; similarly, the thickness of the metal can be varied, with thinner metal arches applying less force. The shape and number of holes can also be varied to tune the force; for example, shapes such as those illustrated in FIGS. 8A-8D can be employed.

A further expander design can employ a shape-memory material such as a shape-memory alloy or a shape-memory polymer that responds to temperature by altering its shape. The appliance can be prepared such that the expander has a first shape at a cold temperature, such as room temperature, and a second shape at warm temperature, such as human body temperature. The first shape can be selected to fit in a patient's mouth without applying significant expanding forces, while the second shape can be selected to have a larger width than the first shape, such that at a warmer temperature, the expander applies an outwards force on the teeth to expand the palate and/or the arch of the patient. Accordingly, the appliance can be placed in the mouth at room temperature without applying excessive force, and then increase force continuously as the appliance heats to body temperature in the mouth.

Arch Expanders

The appliances disclosed herein, such as arch expanders for example, may have a stiff inner component and a soft outer component. The arch expander may comprise adjacent stiff portions extending in mesial distal directions with a gap extending therebetween. The gap may have a spring or other expansion device, e.g. polymer to urge opposing blocks of teeth against each other. Upon compression shown with arrows, the force generating structure of the gap can urge the adjacent sections apart to move the teeth. Embodiments can have soft material extending around circumference of teeth to provide placement. Exposed occlusal surface can provide improved inter digitation with tooth movement. This arch expander can also be used to align teeth.

The force generating structure can be built in and directly fabricated, for example as an expander with spring feature at the gap in stiff elongate portions to cause expansion. The distal teeth may comprise anchoring molars to facilitate movement of the anterior teeth on an opposite side of the gap comprising the expandable structure. The arch can be expanded with increasing separation of the elongate stiff segments having the gap extending therebetween.

Figure 11:
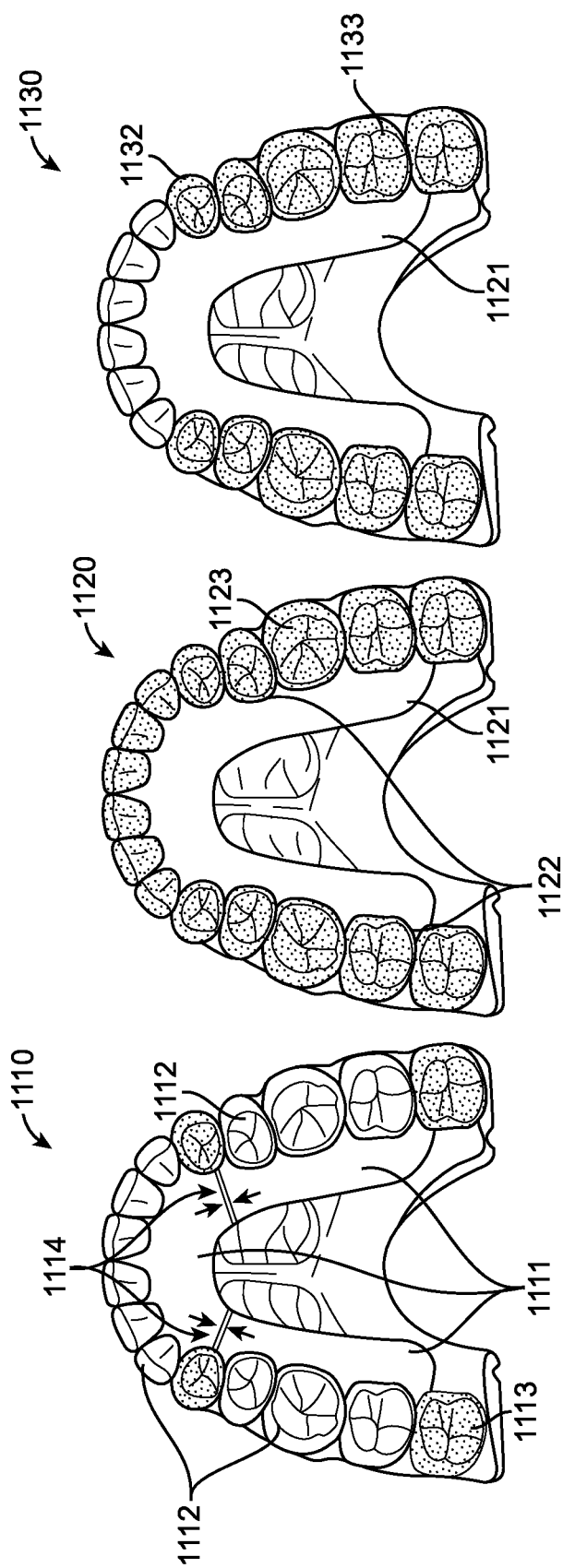
FIG. 11 illustrates a variety of different arch expander designs that may be incorporated into an orthodontic appliance in accordance with embodiments.

FIG. 11 illustrates a variety of different arch expander designs that may be incorporated into an orthodontic appliance, for example when designing an appliance in method 200. Arch expanders 1111, 1121, and 1131 are shown incorporated into orthodontic appliances 1110, 1120, and 1130 respectively. Appliances 1110, 1120, and 1130 each comprise tooth-receiving structures 1112, 1122, and 1132, respectively, such as cavities, designed to receive one or more of teeth 1113, 1123, and 1133, respectively. As illustrated, tooth-receiving structures 1112, 1122, and 1132 may comprise a soft material, including possibly a soft clear material. As illustrated, arch expanders 1111, 1121, and 1131 may comprise a rigid material, which typically need not be clear, but may optionally be clear as well. The tooth-receiving structures 1112, 1122, and 1132 serve to hold appliances 1110, 1120, and 1130 on teeth 1113, 1123, and 1133, respectively, allowing respective arch expanders 1111, 1121, and 1131 to apply tooth moving forces such as arch expanding forces.

Direct fabrication of the arch expander allows improved fit and can provide more accurate control of the forces to the teeth. The teeth engagement structures of the stiff portion can extend into interproximal spaces of the teeth to improve fit and force coupling, for example.

Typically, an arch expander will be used to expand a dental arch comprising a plurality of teeth, such as teeth 1113. This expansion may comprise a movement of a plurality of teeth in different directions; for example, teeth on opposite medial sides of the mouth may be moved apart. Alternatively or additionally, posterior and anterior teeth may be moved away from each other, so that the overall shape of the dental arch is changed. This type of movement may be useful, for example, in the reduction of tooth crowding, or for other suitable purposes.

To accomplish the expansion of a dental arch, significant arch expanding forces may be used between one or more groups of teeth, in order to push them in different directions. The rigid material of arch expanders 1111, 1121, and 1131 may be exploited to apply arch expanding forces. In some embodiments, an arch expander such as arch expander 1111 may be broken into different segments, separated by gaps 1114. As illustrated, forces may be applied between the separate segments, for example, using material inserted into the gaps 1114. In some embodiments, the gaps may be bridged by one or more screws, which may be rotated in one direction to drive the segments of arch expander 1111 apart, or in the other direction to pull the segments together. The screws may be fabricated as part of the appliance fabrication process, or installed separately using known machining techniques.

In some embodiments, springs may be installed to connect across the gaps 1114, to apply spring forces on arch expander 1111. Depending on the properties of the springs, such as spring elasticity, connection points of the springs to arch expander 1111, and spring rest length, the forces applied by the springs may be varied, optionally including forces tending to push segments apart and/or to pull them together, as desired. The springs may in some cases be fabricated separately and attached to the arch expander 1111 and in some cases may be fabricated along with the arch expander. A combination of springs fabricated separately and as part of the arch expander fabrication process may also be used, as desired. Additionally or alternatively, structures such as bars may connect one or more of the segments of arch expander 1111 to apply force. These bar structures may likewise be fabricated as part of the arch expander 1111 or attached separately.

In some embodiments, an arch expanding force may be exerted between segments by fabricating arch expander 1111 with gaps 1114 filled with a compressible material. By designing the compressible material in the gaps 1114 to have a longer rest length than the gaps would otherwise be when the appliance 1110 is worn, an arch expanding force may be applied as the compressed material in the gaps 1114 pushes outward on the segments of arch expander 1111.

In some embodiments, rigid material in gaps 1114 may be designed so that it changes its properties in response to being placed in a patient's mouth. For example, the material may expand in response to contact with the patient's saliva, such as may be the case in materials such as hydrophilic polymers, for example. Suitable materials for use in this manner may exhibit both high rigidity and swelling capacity. This expansion may be tailored by varying the properties of the material, including the amount of expansion per unit volume and the shape and size of the gaps 1114, as well as the fraction of the gaps in which the material is placed. For example, larger gaps 1114 filled with material with higher swelling capacity may provide more arch expanding force, because the amount of arch expansion force that may be caused by material filling the gaps 1114 grows in proportion to the size of the gaps, as well as to the fraction of the gaps (along the lingual-buccal and/or vertical directions) that has been filled.

A further use of material that expands in response to contact with a patient's saliva is to incorporate the material continuously throughout a solid arch expander. Arch expanders 1121 and 1131 may comprise the expandable material for example. This design of the arch expander allows for nearly arbitrary control over the forces applied to teeth 1123 or 1133. For example, if one or more particular teeth are to be singled out for greater applied force, additional expandable material may be added on one side of the one or more teeth, wherein the extra expansion of that material may apply a greater force to push the one or more teeth away from the material. The distribution of material may be chosen as desired to apply a wide range of customizable forces on teeth 1123 or 1133. This may be used, for example, to guide the teeth individually or in independent groups along a desired trajectory, while expanding the dental arch, for example. Further optional combination may be made with materials having different degrees or rigidity or of swelling capacity along different axes to enable further customization of available forces comprising a plurality of magnitudes and a plurality of directions on each of a plurality of teeth.

Because direct fabrication allows the use of a plurality of different materials in an appliance, the material of the tooth-receiving structures may be chosen independently of the material of the arch expander. Thus, for example, tooth-receiving structures may comprise soft and/or clear material whereas the arch expander may comprise hard and/or non-clear material. Furthermore, the tooth-receiving structures themselves may be made of more than one material, wherein a first and a second set of tooth-receiving structures comprise a first and a second material. For example, tooth-receiving structures configured to receive molars may be fabricated with a different material than those configured to receive incisors.

The tooth-receiving structures may also be designed to engage different teeth in many ways. For example, appliance 1110 comprises tooth-receiving structures 1112 that cover the occlusal surfaces of their respective teeth, whereas appliance 1120 comprises tooth-receiving structures 1122 that extend substantially around and may surround the outer portion of their respective teeth while leaving the occlusal surfaces uncovered. These two options may be combined: for example appliance 1130 comprises tooth-receiving structures 1132 of both types, each engaging a respective set of teeth. The tooth-receiving structures may be configured as needed to engage and anchor to their respective teeth, enabling tooth moving forces such as arch expanding forces to be applied, as by arch expanders 1111, 1121, and 1131.

The exposed occlusal surfaces of the teeth can encourage movement of the teeth to have better occlusion with opposing teeth on an opposite arch. Alternatively, the material on the occlusal surfaces can be sufficiently thin to urge the teeth into appropriate alignment with teeth on the opposing arch.

Figure 12:
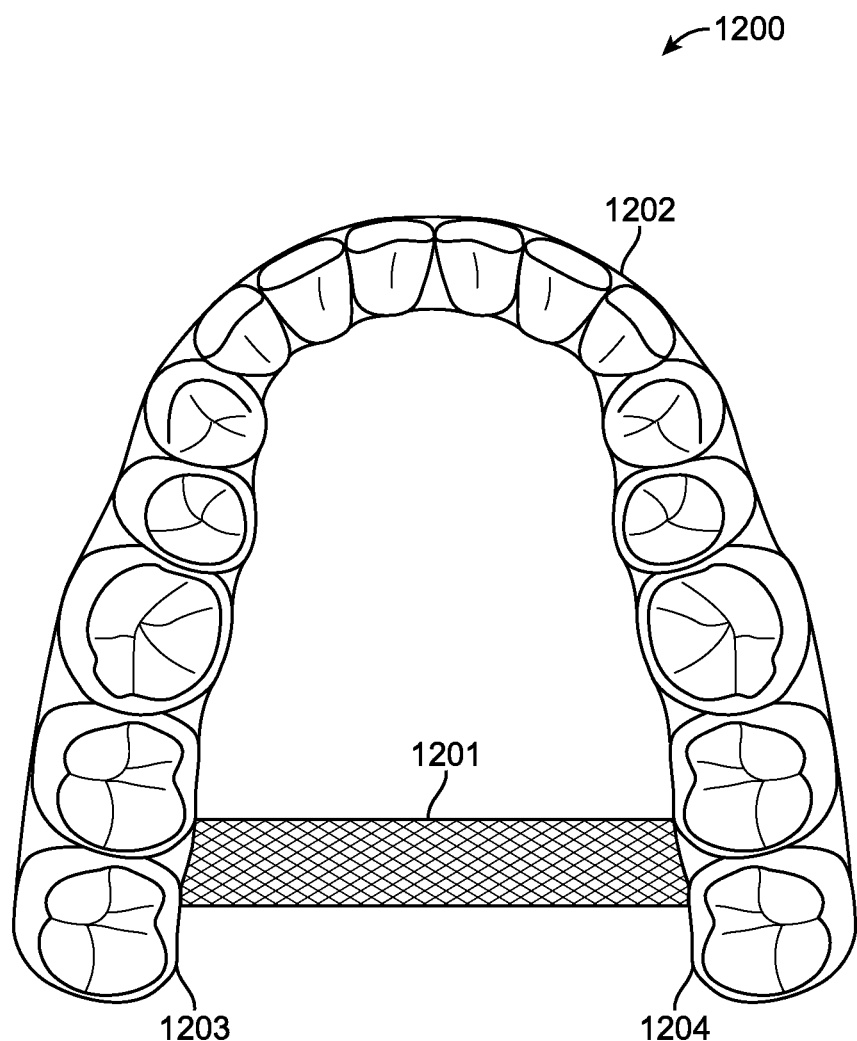
FIG. 12 illustrates a further embodiment in which an appliance may be fabricated with an arch expander comprising a connective portion to apply forces between distant teeth in accordance with embodiments.

FIG. 12 illustrates a further embodiment in which an appliance 1200 may be fabricated with an arch expander comprising a connective portion 1201 to apply forces between distant teeth. The appliance 1200 comprises a polymeric shell 1202 coupled to a connective portion 1201 at locations 1203 and 1204, each location being near one or more distant tooth-receiving structures. The connective portion 1201 allows the transmission of force between teeth at or near locations 1203 and 1204, for example, by applying elastic forces to cause an expansion or contraction of connective portion 1201. Connective portion 1201 may be designed to customize the forces it applies in various ways. Examples of design choices of connective portion 1201 include but are not limited to springs, bars, compressible polymer, or polymer that expands upon contacting saliva. Any of these nonexclusive options may be exercised by fabricating the corresponding structure directly, using fabrication techniques as disclosed herein. In the case of direct fabrication, the appliance 1200 may be fabricated as a whole, including polymeric shell 1202, connective portion 1201, and their joining points 1203 and 1204. Connective portion 1201 may be used on its own to supply an arch expansion force, or it may be combined with other arch expanders such as arch expanders 1111, 1121, or 1131, and any of these may additionally be combined with further orthodontic structures as will be apparent to one of ordinary skill in the art.

Figure 13:
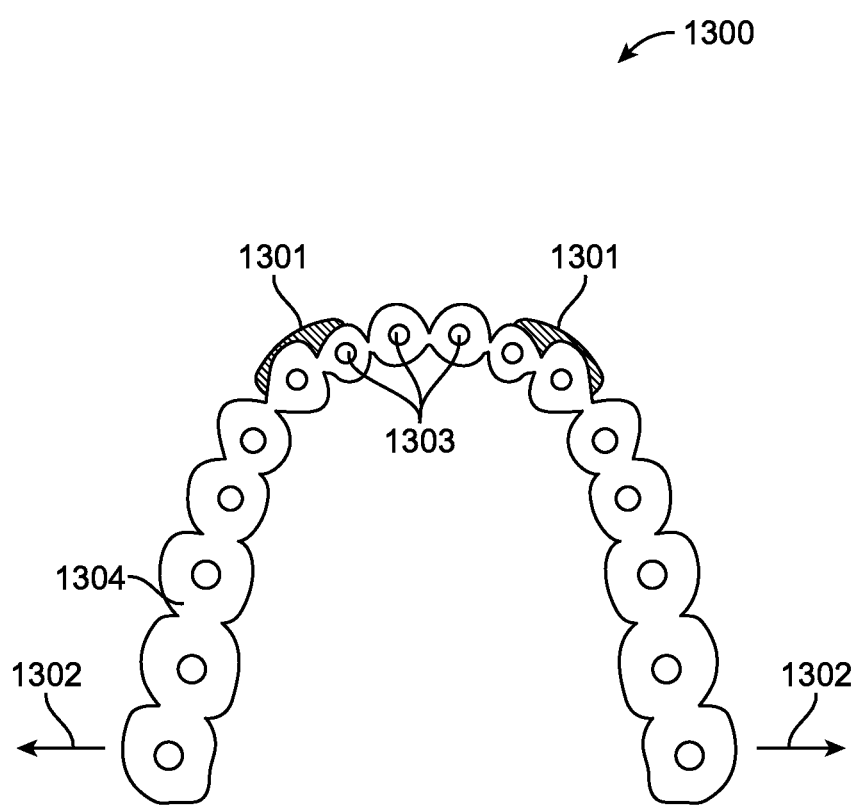
FIG. 13 illustrates an aligner design that may be used in conjunction with the connective portion illustrated in FIG. 12 to guide a tooth movement.

FIG. 13 illustrates an aligner design that may be used in conjunction with the connective portion illustrated in FIG. 12 to guide a tooth movement. The aligner 1300 comprises an orthodontic appliance with a plurality of tooth-receiving cavities 1303. The appliance comprises a force generating portion that applies an arch expanding force 1302. The force generating portion can be the connective portion illustrated in FIG. 12, for example; in alternative embodiments, the force generating portion can be one or the embodiments illustrated in FIG. 11, or in FIGS. 15-16, for example. The aligner comprises a flexible retention portion 1304 that allows movement of the received teeth of the arch in response to force from the force generating portion. The aligner further comprises a stiff retention portion 1301 that resists movements of the nearby teeth, thereby resisting movement of a first plurality of teeth while allowing movement of a second plurality of teeth. For example, the stiff retention portion 1304 can be arranged to inhibit a rotational force about a tooth, such as a canine tooth for example. The stiff retention portion can also resist linear translations, such that tooth moving forces can be distributed selectively across the teeth of the arch. The stiff retention portion reduces the tooth-moving force applied to nearby teeth, so that teeth not near the stiff retention portion experience relatively more force. This permits a controlled movement of portions of the dental arch; for example, the molars may be moved in an outwards direction of the arch expanding force 1302 while movement of the canines and incisors is reduced.

Figure 14A:
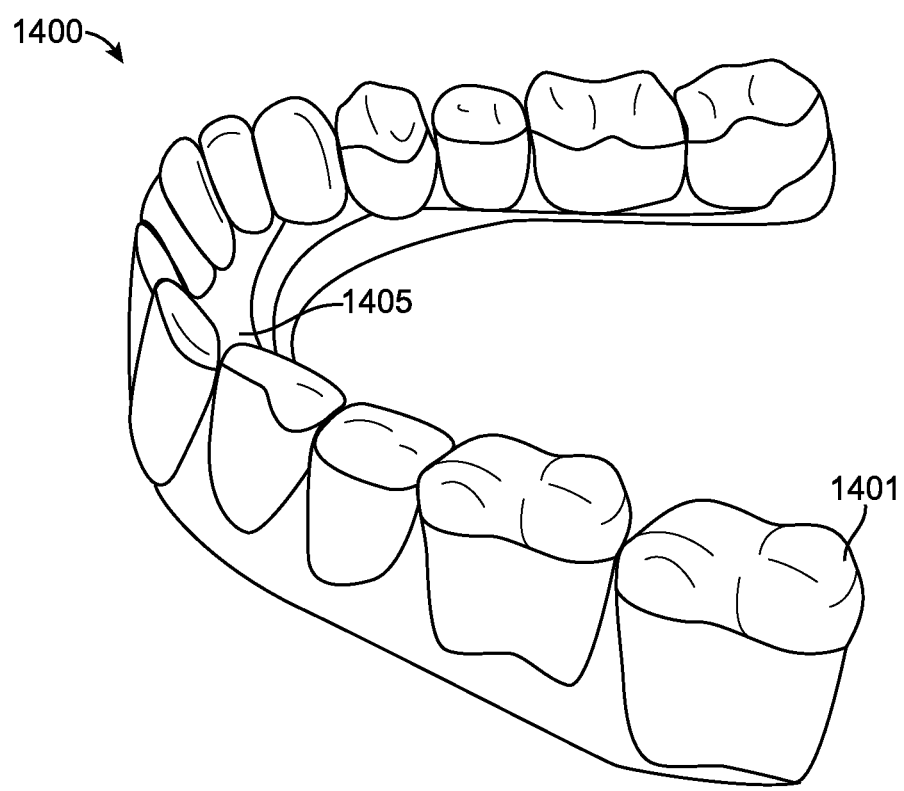
FIG. 14A illustrates an example of an appliance having an anterior tab arch element, according to embodiments.

FIG. 14A illustrates an example of an appliance having an anterior ridge arch element, according to embodiments. FIG. 14A provides an appliance 1400 having a shell 1401 with a ridge 1405 thereon to provide additional rigidity and/or palate expansion force. The anterior ridge 1405 is a small ridge on lingual side of the arch. It may be used to increase structural integrity of the appliance in the transverse direction between the two ends of the jaw. For example, the anterior ridge arch element can provide a stiff retention portion that resists movement of nearby teeth, while allowing movement of other teeth, or causing a first plurality of teeth to move as a unit by providing a stiff connection between the corresponding teeth receiving cavities. In some embodiments, the lingual ridge feature may run along one or more portions of or the entire span of the arch. The cross sectional geometry of the lingual ridge can be varied uniformly or non-uniformly along its length to provide additional rigidity and/or force to adjust the palate.

Figure 14B:
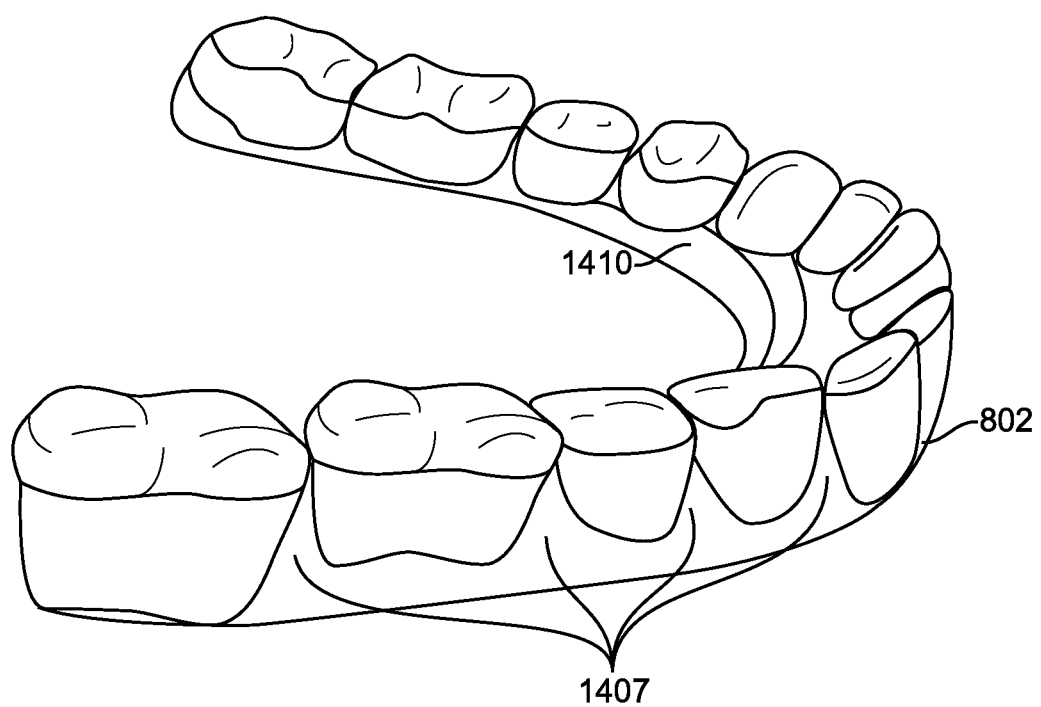
FIG. 14B illustrates an example of an appliance having a rib feature, according to embodiments.

FIG. 14B illustrates an example of an appliance having a rib feature, according to embodiments. FIG. 14B provides an appliance 1400 that has one or more rib features 1407 on the surface of the shell 1402. These features are areas that are thicker than other portions of the appliance body thickness and therefore provide additional rigidity and/or force. The rib portions can be used to provide a stiff retention portion to resist local tooth movement while allowing movement of other teeth received by a flexible retention portion, for example.

Additionally, the ribs are elongate shapes that can be oriented in different directions along the surface of the shell 1402. This enables them to provide forces in specialized directions to control the forces provided to the teeth from the appliance with precision. In the illustrated embodiment, of FIG. 14B, the ribs have been configured in a particular geometry to provide added rigidity to the posterior section of the dental appliance.

For example, in some embodiments, a rib feature can be positioned in the buccal and/or lingual sections between the cavities for the crowns to strengthen the appliance in the transverse direction, so individual teeth can be moved as a segment. In a mixed dentition case, if a primary tooth is lost during treatment, such an embodiment can help preserve the arch expansion force, since the posterior section is being expanded as a segment.

In some embodiments, teeth engaging structures and force generating components as described herein can be directly fabricated as separate components and sized and shaped to fit together for later use. The aligners and arch expanders may be directly fabricated as separate components to be fit together later for use, for example. The arch expander comprises a force generating connector component as disclosed herein and the aligner comprises a teeth engagement structure as disclosed herein. The separate components may comprises corresponding engagement structures that allow the components to fit together and hold the aligner and connector component together when placed in the mouth of the patient. The corresponding engagement structures can be configured in many ways and may comprise one or more of locking structures, a protrusion sized to extend into a receiving structure such as a recess, nested structures or locking structures. The aligner and removable connector component may comprise corresponding shape profiles that allow the corresponding structures of the arch expander to aligner to fit together and be held in place. In some instances, the corresponding structures can be configured for the engagement structures to gently click in place, for example. The user can be provided with a plurality of pieces to use over the course of a treatment plan of arch expansion, for example.

A person of ordinary skill in the art will recognize that the force generating connector components as shown in FIGS. 15A, 15B, 15C, 15D, and 16 can be sized for arch expansion in response appropriate forces for arch expansion and three dimensional shape profile data from a scan of an oral cavity of the mouth of the patient. The embodiments of FIGS. 15A, 15B, 15C, 15D, and 16 are well suited for combination with the embodiments of FIGS. 1, 2, 3, and 4, as well as FIGS. 11, 12, 13, 14A, and 14B—such as shown in FIG. 12, for example. A person of ordinary skill in the art will recognize that the connector components of FIGS. 15A, 15B, 15C, 15D, and 16 can be sized in many ways, as may be desired for orthodontic use.

Figure 15A:
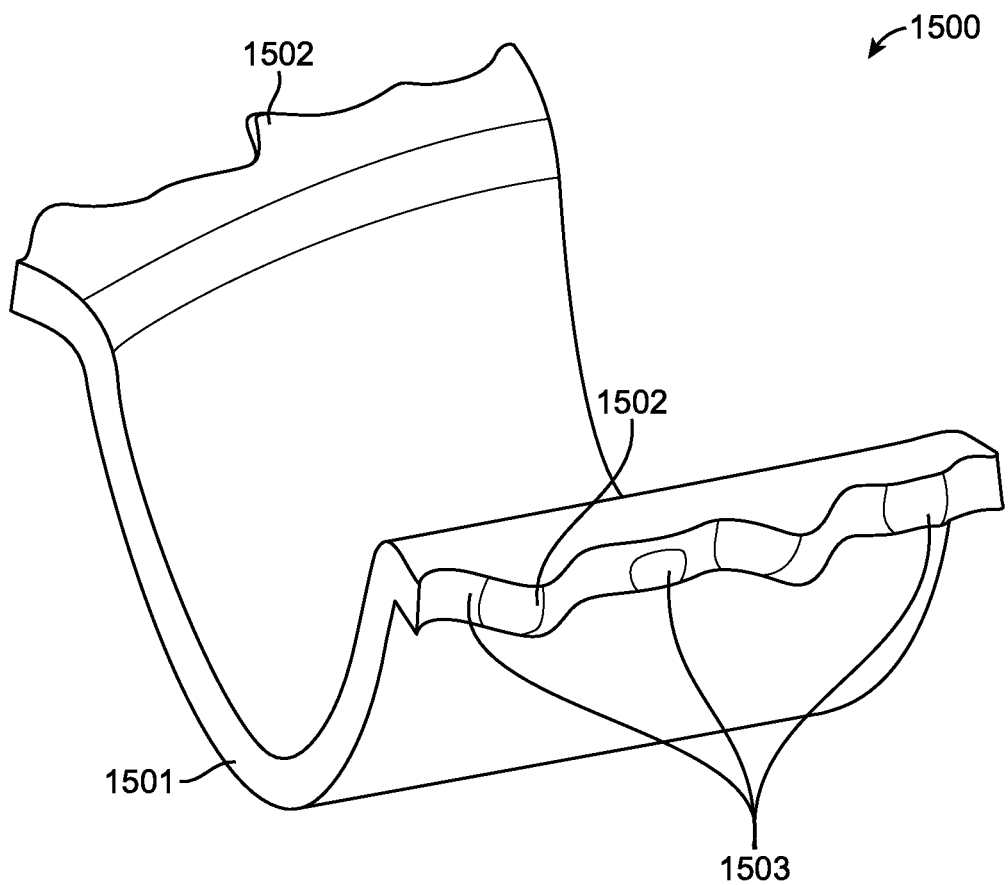
FIG. 15A illustrates an arch expander having a removable connector component fabricated to mate with an orthodontic appliance, in accordance with embodiments.

FIG. 15A illustrates a removable arch expander 1500 fabricated to mate with an orthodontic appliance. The arch expander 1500 comprises a connector component 1501 fabricated from elastic material to fit the palate of a patient. The material may be fabricated to be larger than the patient's arch region, so that it compresses when worn, permitting an outward force to be applied to a patient's teeth. The arch expander 1500 further comprises a ridged portion 1502 on each side designed to conform to the surface of an orthodontic appliance. The rigid portion 1502 may comprises protrusions sized and shaped to extend toward interproximal the space of the teeth when engaging corresponding structures of the teeth engaging appliance. In order to secure the force generating connector portion of the arch expander to an orthodontic appliance such as an aligner, indentations 1503 may be located in the ridged portion 1502 configured to mate with protrusions on the appliance.

Figure 15B:
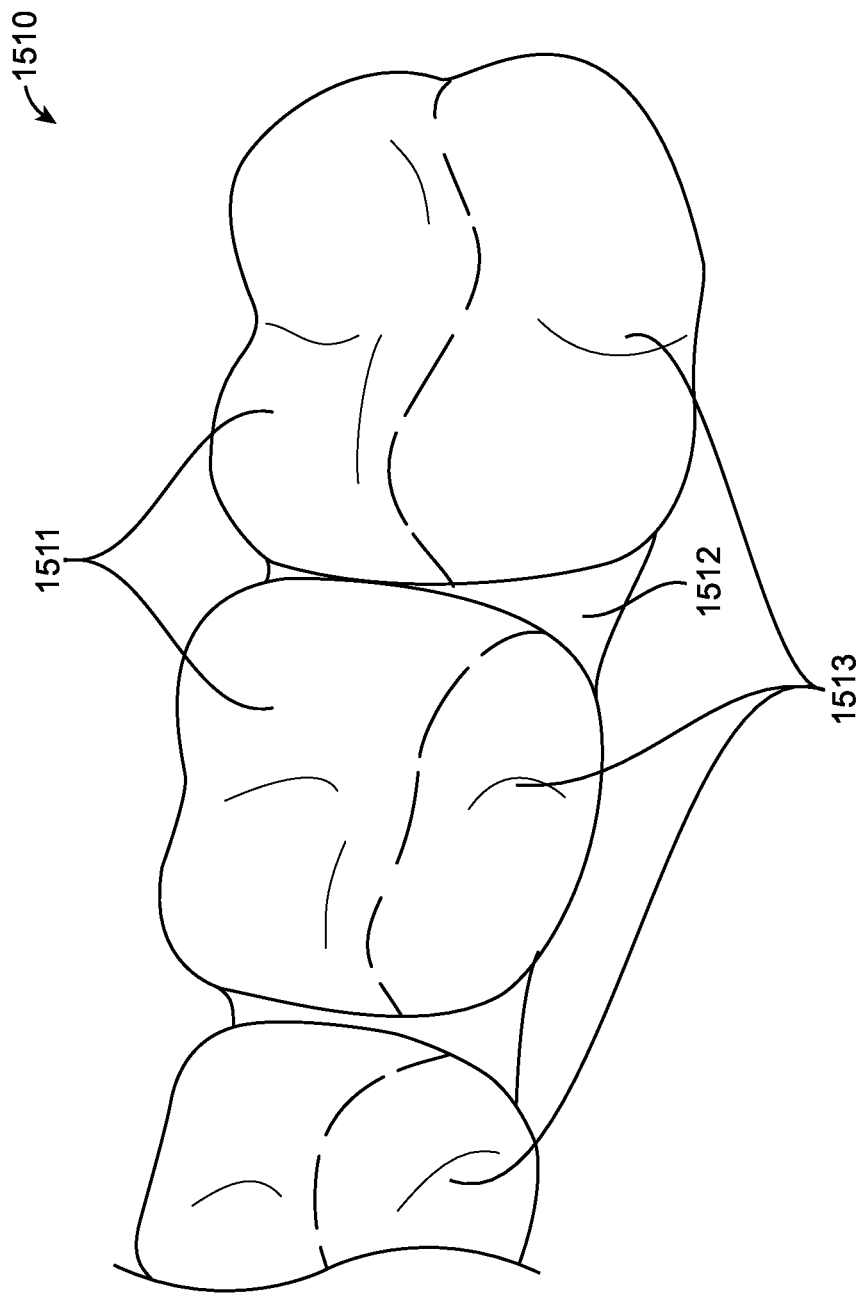
FIG. 15B illustrates part of an aligner designed to mate with a removable connector component, in accordance with embodiments.

FIG. 15B illustrates part of an aligner 1510 designed to mate with a connector component as shown in FIG. 15A. The aligner 1510 comprises a plurality of teeth engagement structures comprising a plurality of teeth receiving cavities 1511 sized and shaped to engage the teeth for arch expansion. The aligner comprises plurality of tooth-receiving cavities 1511, as well as a labial contour 1512. The labial contour 1512 matches the corresponding ridged portion 1502 of the connector component. The teeth engaging aligner component further comprises protrusions 1513 configured to engage, for example mate, with the corresponding indentations 1503 of the arch expander 1500. The protrusions 1513 can be located on a labial side of the teeth. The teeth engaging aligner component may comprise receiving structures shaped to receive the protrusions of the rigid portion 1502 of the connector component 1501. This arrangement allows the connector component 1501 and the aligner 1510 to hold together, for example to securely mate together. The aligner 1510 can be configured to move teeth in accordance with a treatment plan as described herein. The connector component 1501 can be configured to move the arch in accordance with an arch expansion plan.

The teeth engagement structures that couple to the teeth can be configured in many ways. Although an aligner is shown, other structures as described herein can be used to engage the teeth and couple to the connector component in order to engage the teeth.

Figure 15C:
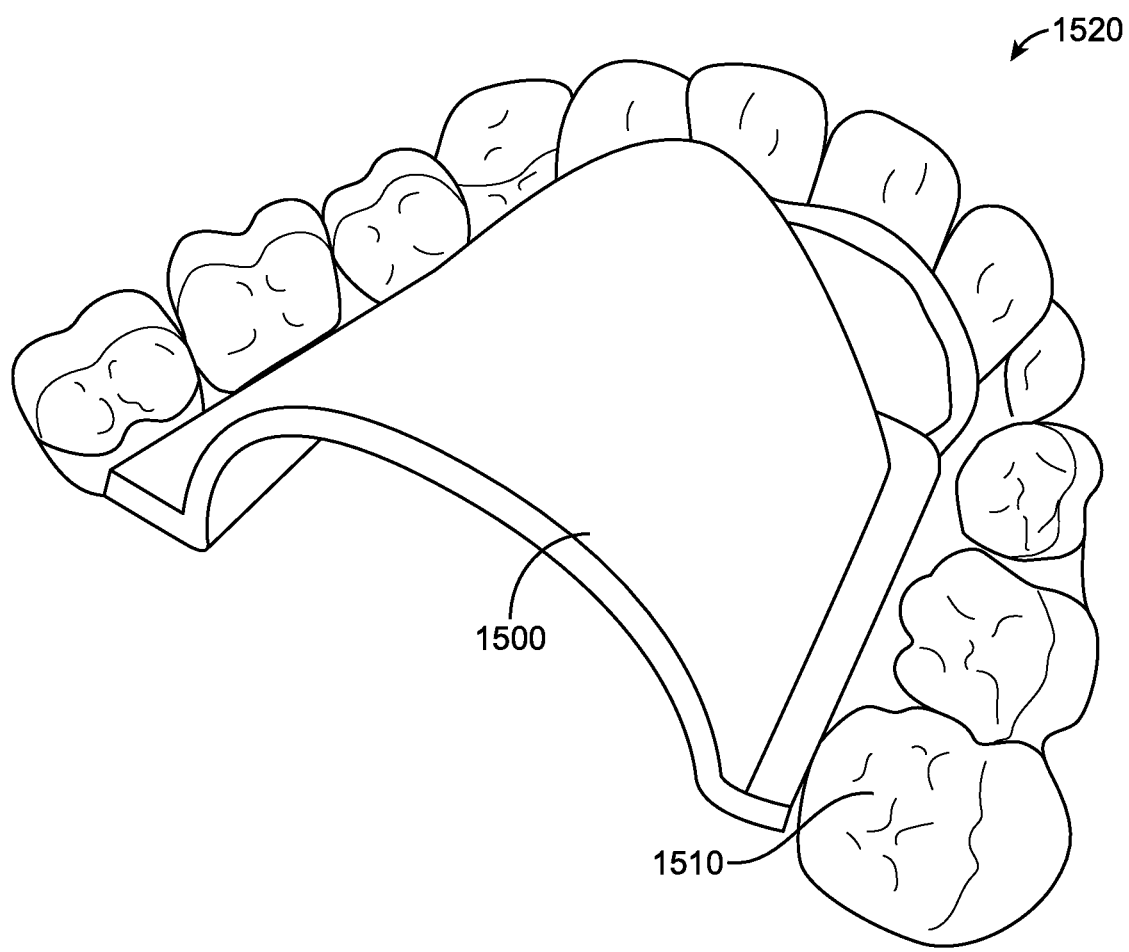
FIG. 15C illustrates a prototype orthodontic appliance comprising both a removable connector and an aligner in accordance with embodiments.

FIG. 15C show a picture of a directly fabricated orthodontic appliance 1520 comprising a palate expander that can be modified in accordance with the present disclosure for arch expansion. The connector component 1500 comprises mating structures as disclosed herein and is shown coupled to an aligner 1510. The connector component and aligner are made of different materials, with the connector component capable of flexing when worn to store elastic energy, thereby applying force to a patient's teeth. The connector component comprises an unloaded free standing configuration with the engagement structures such as protrusion having a separation distance on opposing sides of the connector component sized larger than corresponding structures of opposing sides of the arch of the aligner.

Figure 15D:
FIG. 15D illustrates a 3D model of an appliance comprising a removable connector component and an aligner in accordance with embodiments.

A 3D computer model 1530 of appliance 1520, which may for example be generated when designing an orthodontic appliance according to methods 200 or 300, is illustrated in FIG. 15D. A person of ordinary skill in the art can use computer modeling and experimentation to determine the forces to the teeth appropriate for arch expansion, and determine the size, shape and material of the connector component as described herein. The connector component can be sized to inhibit or avoid contact with the arch in response to an oral scan to generate three dimensional profile data of the mouth as described herein.

Figure 16:
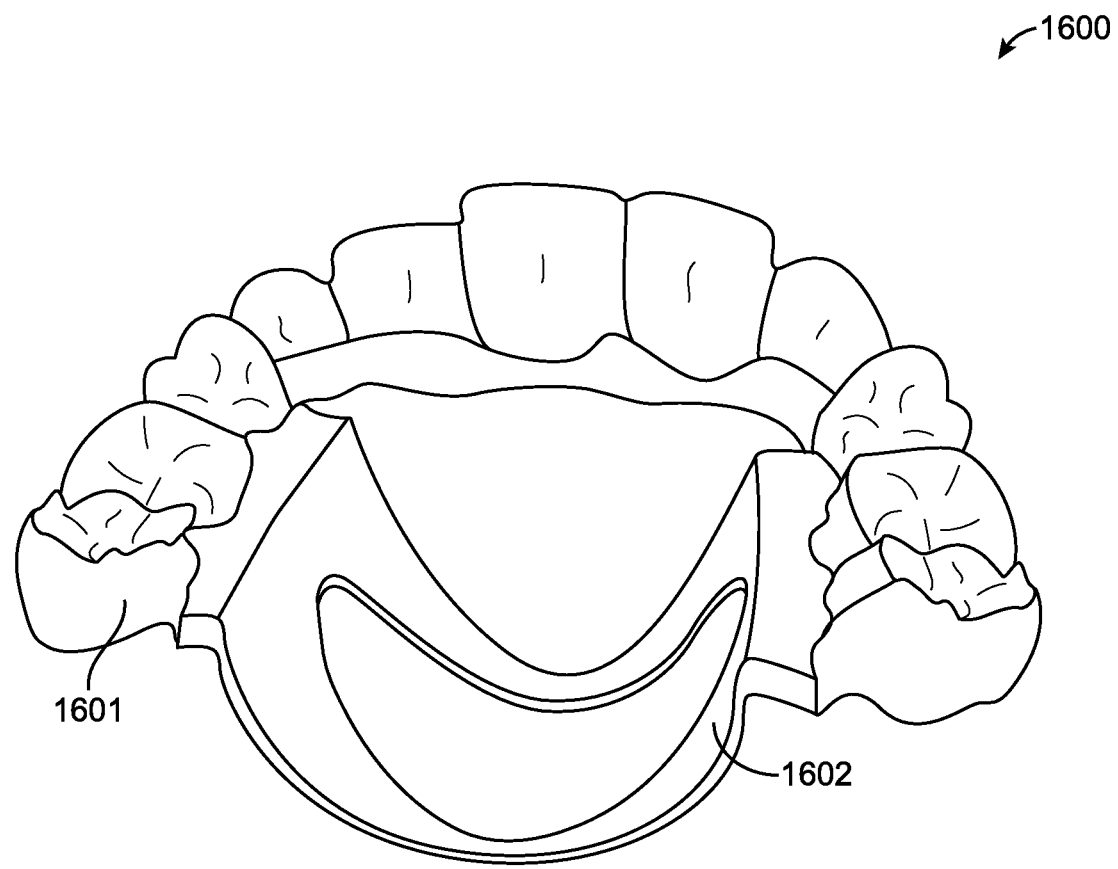
FIG. 16 shows an orthodontic appliance comprising a plastic aligner portion and a metallic connector component in accordance with embodiments.

FIG. 16 shows a design of an orthodontic appliance 1600 comprising a plastic aligner component 1601 and a metallic connector component 1602. The use of metal materials offers a number of advantages, such as greater applicable force, lack of stress relaxation, durability, corrosion resistance, and easy sterilization. Biocompatibility is also readily achieved, since the use of metallic material in orthodontics is already used in the dental industry, and the selection of appropriate metals will be apparent to one of ordinary skill in the art. Metallic aligners may be usefully fabricated using direct fabrication techniques such as Direct Metal Laser Sintering (DMLS), and in some cases may be fabricated directly along with a directly fabricated plastic aligner component.

Direct Laser Sintering (DLS) of plastic material may also be used to fabricate one or more of the components as disclosed herein. Moreover, other direct fabrication techniques may be used in addition to, or as an alternative to, laser sintering of plastic and/or metal. For example, stereolithography, selective laser sintering, fused deposition modeling, 3D printing, continuous direct fabrication, and/or multi-material direct fabrication may be employed for making part or all of the palate and arch expanders disclosed herein. Part or all of said palate and arch expanders may also be formed using indirect fabrication techniques, such as thermoforming, for example. In some cases, a first part of an appliance can be formed using a first manufacturing process, and thereafter combined with a second part of an appliance formed using a second manufacturing process. For arch or palate expanders comprising three or more parts, each part may be formed using a separate process, or some or all parts may be formed by the same process. A first part may also be fabricated by a first process, and thereafter a second part may be formed around or upon the first part—for example, by 3D printing one or more layers of material on a previously formed structure to generate a combined appliance comprising multiple parts and/or materials.

In some cases, it may also be desirable to incorporate electronic or mechanical components within an orthodontic appliance. Electronics may be used, for example, to measure such quantities as force applied, movement of teeth, physical properties within the mouth, or compliance by the patient in wearing the appliance. Mechanical elements may be used to vary force or movement of the appliance, for example, in response to measurements of force or movement by electronic sensors. To accommodate such electronics and mechanics, appliances may be fabricated with cavities into which appropriate devices may be inserted. In some cases, an appliance may be directly fabricated around an electronic or mechanical component, so that the component is contained within the appliance.

In many embodiments, it can be desirable to combine the arch expanders and palate expanders disclosed herein, to provide expansion of the palate in combination with expansion of one or both arches or other movement of the teeth. Expansion of the palate can cause movement of the teeth of the upper dental arch, which can change the shape of the upper arch as well as the alignment of the teeth of the upper and lower arches. Consequently, it can be desirable to rearrange one or both of the upper and lower arches to compensate. In some cases, a sequence of orthodontic appliances comprising arch and palate expanders is fabricated to provide sequential expansions of a patient's palate and arch. For example, a patient's palate can be expanded by a palate expander, and subsequently the lower arch can be expanded to align the upper and lower arches. In some cases, arch and palate expanders may be provided for simultaneous use, such as expansion of the palate and upper arch by a palate expander in combination with an expansion of the lower arch with an arch expander. A single appliance can also provide both tooth moving forces—such as arch expansion forces or other orthodontic forces (such as rearrangements of specific teeth)—and palate expansion forces. For example, expansion of an arch or palate may change the spacing or orientations of teeth in an arch, which can be corrected either simultaneously or subsequently with an appropriate orthodontic appliance, to close gaps or reorient teeth, for example. For example, palate expansion can cause the space between anterior teeth such as incisors to change, resulting in gaps or other tooth misalignments. A palate expander as disclosed herein can further comprise teeth receiving cavities configured to apply forces to direct teeth of the patient into a desired alignment as the palate expands. When designing the palate expander, the movement of teeth and of the palate can be modeled and the teeth receiving cavities of the appliance can be designed to account for the resultant expansion of the palate by applying forces to the patient's teeth in order to bring them into proper orthodontic alignment. Such combined forces can obviate or reduce the need for further orthodontic correction after palatal expansion.

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A dental appliance to expand a palate of a patient, the dental appliance comprising:
    a teeth engagement component comprising:
    a plurality of cavities configured to receive the teeth of the patient, including a molar cavity configured to receive a molar of the patient, wherein the molar cavity comprises a flattened occlusal surface;
    a plurality of expander-engaging structures, wherein the plurality of expander-engaging structures are located along interproximal regions of the plurality of cavities, and wherein the plurality of expander-engaging structures comprise a lingual contour between the cavities; and
    an expander component comprising:
    a plurality of engagement protrusions, wherein the plurality of engagement protrusions are sized and shaped to extend toward interproximal regions of the patient's teeth, and wherein the plurality of engagement protrusions are configured to bias against the plurality of expander-engaging structures at respective interproximal regions of the patient's teeth; and
    a resilient and compressible material to exert an expansion force to the palate when the dental appliance is worn by the patient.

2. The appliance of claim 1, wherein the dental appliance comprises a sintered expander or a sintered teeth engagement component.

3. The appliance of claim 1, wherein the dental appliance comprises both a sintered expander and a sintered teeth engagement component, and wherein each of the teeth engagement component and the expander component comprise a respective sintered material each independently selected from sintered metal, sintered plastic, or a combination thereof.

4. The appliance of claim 1, wherein the dental appliance is shaped to engage a temporary anchorage device in the palate of the patient to apply a palate expanding force when worn.

5. The appliance of claim 1, wherein the dental appliance is further configured to apply a tooth moving force to one or more anterior teeth of the upper arch while expanding the palate.

6. The appliance of claim 1, wherein the expander component is configured to have a target palatal displacement, and to apply the expansion force to expand the palate to the target palatal displacement.

* * * * *